United States Patent [19]
Shen et al.

[11] Patent Number: 6,060,473
[45] Date of Patent: *May 9, 2000

[54] 7-AZABICYCLO[2.2.1]-HEPTANE AND -HEPTENE DERIVATIVES AS CHOLINERGIC RECEPTOR LIGANDS

[75] Inventors: T. Y. Shen, Great Falls; W. Dean Harman, Earlysville; Dao Fei Huang, Charlottesville, all of Va.; Javier Gonzalez, Casselberry, Fla.

[73] Assignee: UCB S.A. - DTB, Brussels, Belgium

[*] Notice: This patent is subject to a terminal disclaimer.

[21] Appl. No.: 08/700,230

[22] Filed: Aug. 20, 1996

Related U.S. Application Data

[63] Continuation-in-part of application No. 08/041,445, Apr. 1, 1993, abandoned
[60] Provisional application No. 60/002,551, Aug. 21, 1995.

[51] Int. Cl.[7] .................... C07D 413/04; C07D 417/04; C07D 401/04; A61K 31/44
[52] U.S. Cl. .................. 514/253; 514/256; 514/339; 514/413; 546/276.7; 548/312.1; 548/452; 548/466; 544/333; 544/405
[58] Field of Search ............ 546/276.7; 548/312.1, 548/452, 466; 544/405, 333; 514/253, 256, 339, 413

[56] References Cited

U.S. PATENT DOCUMENTS

| | | | |
|---|---|---|---|
| 4,835,162 | 5/1989 | Abood | 514/305 |
| 4,910,193 | 3/1990 | Buchheit | 514/216 |
| 4,940,703 | 7/1990 | Baker et al. | 514/210 |
| 4,966,916 | 10/1990 | Abood | 514/534 |
| 4,992,436 | 2/1991 | Baker et al. | 514/215 |
| 5,104,989 | 4/1992 | Cottrell et al. | 546/112 |
| 5,106,853 | 4/1992 | Showell et al. | 514/299 |
| 5,124,460 | 6/1992 | Humphrey | 548/131 |
| 5,128,118 | 7/1992 | Carroll et al. | 424/1.85 |
| 5,219,860 | 6/1993 | Chambers et al. | 514/278 |
| 5,227,385 | 7/1993 | Caldwell et al. | 514/304 |
| 5,242,927 | 9/1993 | Baker et al. | 514/299 |
| 5,242,930 | 9/1993 | Baker et al. | 514/305 |
| 5,256,671 | 10/1993 | Ladduwahetty | 514/305 |
| 5,260,293 | 11/1993 | Baker et al. | 514/214 |
| 5,288,730 | 2/1994 | Baker et al. | 514/305 |
| 5,314,899 | 5/1994 | Daly et al. | 514/339 |
| 5,324,723 | 6/1994 | Baker et al. | 514/212 |
| 5,405,853 | 4/1995 | Baker et al. | 514/299 |
| 5,426,106 | 6/1995 | Kalagowski et al. | 514/233 |
| 5,432,177 | 7/1995 | Baker et al. | 514/253 |
| 5,444,074 | 8/1995 | Baker et al. | 514/326 |
| 5,451,588 | 9/1995 | Baker et al. | 514/323 |
| 5,459,270 | 10/1995 | Williams et al. | 546/152 |
| 5,461,063 | 10/1995 | Kelleher et al. | 514/312 |

FOREIGN PATENT DOCUMENTS

| | | |
|---|---|---|
| 6312989 | 11/1994 | Japan . |
| 7010878 | 1/1995 | Japan . |
| WO 93/18037 | 9/1993 | WIPO . |
| WO 94/04152 | 3/1994 | WIPO . |
| WO 94/07489 | 4/1994 | WIPO . |
| WO 94/22868 | 10/1994 | WIPO . |
| WO 95/07078 | 3/1995 | WIPO . |
| WO 96/06093 | 2/1996 | WIPO . |

OTHER PUBLICATIONS

Abstracts of Poster Presentations Nos. 1–97, "The Otto Loewi New Investigator Awards for 1995," *Life Sciences*, 56(11/12):1001–1050 (1995).

Adamus, et al., "Phase I Clinical Trials with WAL2014, A New Muscarinic Agonist for the Treatment of Alzheimer's Disease," *Life Sciences*, 56:(11/12):883–890 (1995) (Elsevier Sciences, Ltd., Editors).

Ainsworth, et al., "Alkyl–1,3,4–oxadiazoles," *J. Org. Chem.*, 31:3442–3444 (1966).

(List continued on next page.)

*Primary Examiner*—Alan L. Rotman
*Attorney, Agent, or Firm*—McDonnell, Boehnen, Hulbert & Berghoff

[57] ABSTRACT

7-Azabicyclo[2.2.1]-heptane and -heptene derivatives are disclosed that can be administered to a mammal, including a human, to treat disorders associated with a decrease or increase in cholinergic activity.

42 Claims, 9 Drawing Sheets

OTHER PUBLICATIONS

Altenbach, H.J., et al., "7–Azanorbornadiene," *Angew Chem. Int. Ed. Engl.*, 21(10):778 (1992).

Altenbach, H.J., et al., "Syntheses and Photoelectron Spectra of 7–Azanorbornadiene and Related Compounds. An Analysis with Fragment Orbitals," *Chem. Ber.* 124:791–801 (1991).

Badio and Daly, "Epibatidine, a Potent Analgetic and Nicotinic Agonist," *Mol. Pharmacol.*, 45:563–569 (1994).

Badio and Daly, "Epibatidine. A potent analgetic and nicotinic agonist," *FASEB Journal*, 8(4–5):A875 (1994).

Baker and Saunders, "Central Muscarinic Ligands and Receptors," *Ann. Rep. in Med. Chem.* Chapter 4, 24:31–39 (1989).

Bansal, et al., "Influence of Lewis acids on the Diels–Alder reaction. Part I. An improved synthesis of 7–azanorbornadiene, 3–azaquadricylaine, and azepine derivatives," *Can. J. Chem.*, 47:2391–2394 (1969).

Barber, and Gottschlich, "Opioid Agonists and Antagonists: An Evaluation of Their Peripheral Actions in Inflammation," *Medicinal Research Review*, 12(5):525–562 (1992).

Barnes, et al., "Tiotropium Bromide (Ba 679 BR), a Novel, Long–Acting Muscarinic Antagonist for the Treatment of Obstructive Airways Disease," *Life Sciences*, 56:(11/12):853–859 (1995) (Elsevier Science, Ltd., Editors).

Bhattacharya, S.N., et al., "Friedel–Crafts Sulphonylation of Bis(trimethylsilyl)acetylene: a Useful Route to Aryl Ethynyl Sulphones," *Organomet. Chem. Synth.*, 1:145–149 (1970).

Bittoun, "Recurrent aphthous ulcers and nicotine," *Med. J. Australia*, 154:471–472 (1991).

Bradley, "Frog Venom Cocktail Yields A One–Handed Painkiller," *Science* 261:1117 (1993).

Broka, C.A., "Total Synthesis of Epibatidine," *Tet. Lett.*, 34(20):3251–3254 (1993).

Burgen, "The Background of the Muscarinic System," *Life Sciences*, 56(11/12):801–806 (1995) (Elsevier Science, Ltd., Editors).

Burke, et al., "Construction of a Molecular Shape Analysis–Three–Dimensional Quantitative Stucture–Analysis Relationship for an Analog Series of Pyridobenzodiazepinone Inhibitors of Muscarinic 2 and 3 Receptors," *J. Med. Chem.*, 37:3775–3788 (1994).

Carroll, et al., "3–Aryl–2–(3'–substituted–1',2',4'–oxiadiazol–5'–yl)tropane Analogues of Cocaine: Affinities at the Cocaine Binding Site at the Dopamine, Serotonin, and Norepinephrine Transporters," *J. Med. Chem.*, 36:2886–2890 (1993).

Clayton and Regan, "A Total Synthesis of (+/-) Epibatidine," *Tetrahedron Letters*, 34(46):7493–7496 (1993).

Cooley, et al., "Effect of pCPA on Nicotine–Induced Analgesia," *Pharmacol. Biochem. Behav.*, 36:413–415 (1990).

Cordone, R., et al., "π–Heterocyclic Complexes of Pentaammineosmium(II) and the Metal–Induced Cycloaddition of Pyrrole and Maleic Anhydride," *J. Am. Chem. Soc.*, 111:5969–5970 (1989).

Corey, E.J., et al., "Stereocontrolled Total Synthesis of (+)– and (-)–epibatidine," *J. Org. Chem.*, 58:(21):5600–5602 (1983).

Corey, et al., "A Synthetic Method for Formyl–Ethynyl Conversion (RCHO->RC=CH or RC=CR')," *Tetrahedron Letters*, 36:3769–3772 (1972).

Daly, et al., "A New Class of Indolizidine Alkaloids from Poison Frog, *Dendrobates tricolor*. X–ray Analysis of 8–Hydroxy–8–methyl–6–(2'–methylhexylidene)–1–azabicyclo[4.3.0]nonane," *J. Am. Chem. Soc.*, 102:830–836 (1980).

Davis and Whitham, "Ethynyl p –Tolyl Sulphone as an Acetylene Equivalent in Diels–Alder Reactions," *J.C.S. Chem. Comm.*, pp. 639 (1980).

Devor and Isenberg, "Nicotine and Tourette's Syndrome," *Lancet*, 2:1046 (1989).

Donnini and Just, "Diels–Alder Reactions of Pyrroles as an Entry to Substituted 3–Oxatropanes and Tetrasubstituted Pyrrolidines," *Heterocycl. Chem.*, 14:1423–1425 (1977).

Drew, et al., "High–pressure Synthesis, Structures, and Conformational Properties of Some Derivatives of 7–Azabicyclo[2.2.1]heptane. X–Ray Determiniation of endo –10–Benzoyl–4–phenyl–4,10–diazatricyclo[5.2.1.0$^{2,6}$] dec–8–ene–3,5–dione and exo –10–Acetl–4–phenyl–4, 10–diazatricyclo[5.2.1.0$^{2,6}$]decane–3,5–dione," *J.C.S. Perkins Trans* I:1277–1284 (1985).

Dukat, M.; et al., "Epibatidine: A very high affinity nicotine–receptor ligand," *Medicinal Chem. Res.*, 4:131–139 (1994).

Duvoisin, "Cholinergic–Anticholinergic Antagonism in Parkinsonism," *Arch. Neurol.* 17:124–136 (1967).

Ehlert and Thomas, "Functional Role of $M_2$ Muscarinic Receptors in the Guinea Pig Ileum," *Life Sciences*, 56(11/12):965–971 (1995) (Elsevier Science, Ltd., Editors).

Ehringer and Hornykiewicz, "Verteilung Von Noradrenalin Und Dopamin (3–Hydroxytyramin) Im Gehirn Des Menschen Und Ihr Verhalten Bei Erkrankungen Des Extrapyramidalen Systems," *Klin. Wochenschr.*, 38:1236–1239 (1960).

Feriani, et al., "Cholinergic Agents Structurally Related to Furtrethonium. 2. Synthesis and Antimuscarinic Activity of a Series of N–[5–[(1'–Substituted–acetoxy)methyl]–2–furfuryl]dialkylamines," *J. Med. Chem.*, 37:4278–4287 (1994).

Fisher, et al., "Epibatidine, An Alkaloid From the Poison Frog *Epipedobates tricolor*, Is a Powerful Ganglionic Depolarizing Agent," *J. of Pharm. and Exp. Therap.* 270:702–707 (1994).

Fitjer, et al., "The Wittig Reaction using Potassium–Tert–Butoxide High Yield Methylenations of Sterically Hindered Ketones," *Synthetic Communications*, 15(10):855–864 (1985).

Fletcher, et al., "The Synthesis of (+) and (-) Epibatidine," *J. Chem. Soc. Chem. Comm.*, 1216–1218 (1993).

Fletcher, S., et al., "Total synthesis and determination of the absolute configuration of epibatidine," *J. Org. Chem.*, 59(7):1771–1778 (1994).

Flynn, et al., "Differential Alterations in Mscarinic Receptor Subtypes in Alzheimer's Disease: Implications for Cholinergic–Based Therapies," *Life Sciences*, 56(11/12):868–876 (1995) (Elsivier Science, Ltd., Editors).

Fraser and Lee, "Regulation of Muscarinic Receptor Expression of Changes in mRNA Stability," *Life Science*, 56(11/12):899–906 (1995) (Elsevier Sciences, Ltd., Editors).

Fraser, et al., "Synthesis of 7–azabicyclo[2.2.1]heptane, exo –2–chloro–7–azabicyclo[2.2.1]heptane, and derivatives," *Can. J. Chem.*, 48:2065–2074 (1970).

Gabel, N.W., "Diels–Alder Reactions of 1–Carbomethoxy–pyrroles and Dimethyl cetylenedicarboxylate," *J. Org. Chem.*, 27:301–303 (1962).

Garvey, et al., "Novel Isoxazoles which Interact with Brain Cholinergic Channel Receptors Have Intrinsic Cognitive Enhancing and Anxiolytic Activities," *J. Med. Chem.*, 37:1055–1059 (1994).

Garvey, et al., "Synthesis and in Vitro Characterization of Novel Amino Terminally Modified Oxotremorine Derivaties for Brain Muscarinic Receptors," *J. Med. Chem.*, 35:1550–1557 (1992).

Glassman and Covey, "Future Trends in the Pharmacological Treatment of Smoking Cessation" *Drugs*, 40(1):1–5 (1990).

Goldstein and Shen, "Dual Inhibitors of Platelet Activating Factor and 5–Lipoxygenase II. Novel 2,4–Diaryl–1,3–dithiolanes with Iron–Chelating Functionalities," *Med. Chem. Res.*, 2:451–456 (1992).

Goldstein and Shen, "Dual Inhibitors of Platelet Activating Factor and 5–Lipoxygenase I. 2,4–Diaryl–1,3–dithiolanes," *Med. Chem. Res.*, 2:443–450 (1992).

Gonzalez, J., et al., "Dearomatization of Analines via Complexation to Pentaammineosmium(II): A Novel [2+2+2] Michael–Ring–Closure Reaction of an $n^2$–Coordinated Analine," *Am. Chem. Soc. Mtg.*, 205th ACS National Meeting, Denver CO, Mar. 1993.

Gopalakrishnan and Sullivan, "Targeting Nicotinic Cholinergic Receptors," *Drug News & Perspectives*, 7(7):444–448 (1994).

Gourlay and McNeil, "Antismoking products," *Med. J. Australia*, 153:699–707 (1990).

Grunberg, et al., "Effects of nicotine on body weight and food consumption in rats," *Psychopharmocology*, 83:93–98 (1984).

Hacksell, et al., "Quinuclidin–2–ENE–Based Muscarinic Antagonists," *Life Sciences*, 56(11/12):831–836 (1995) (Elsevier Science, Ltd., Editors).

Hamilton, et al., "Molecular Analysis of the Regulation of Muscarinic Receptor Expression and Function," *Life Sciences*, 56:11/12):939–943 (1995) (Elsevier Science, Ltd., Editors).

Hersch and Levey, "Diverse Pre– and Post–Synaptic Expression of m1–m4 Muscarinic Receptor Proteins in Neurons and Afferents in the Rat Neostriatum," *Life Sciences*, 56(11/12):931–938 (1995) (Elsevier Science, Ltd., Editors).

Hille, et al., "Multiple G–Protein–Coupled Pathways Inhibit N–Type Ca Channels of Neurons," *Life Sciences*, 56(11/12):989–992 (1995) (Elsevier Science, Ltd., Editors).

Hirschberg, et al., "Kinetic and Biophysical Analysis of the m2 Muscarinic Receptor," *Life Sciences*, 56(11/12):907–913 (1995) (Elsevier Science, Ltd., Editors).

Hodges, L.M., et al., "$\eta^2$–Pyrrole Complexes as Synthons to Alkaloid Derivatives," *J. Org. Chem.*, 58:4 788–4790 (1993).

Hosey, et al., "Multiple Mechanisms Involving Protein Phosphorylation are Linked to Desensitization of Muscarinic Receptors," *Life Sciences*, 56(11/12):951–955 (1995) (Elsevier Science, Ltd., Editors).

Huang and Shen, "A Versatile Total Synthesis of Epibatidine and Analogs," *Tet. Let.*, 34:4477–4480 (1993).

Huang, D.F., et al., "A Versatile Total Synthesis of Epibatidine and Analogs," *Tetrahedron Letters*, 58:28 4477–4480 (1993).

Hulme, et al., "The Role of Charge Interactions in Muscarinic Agonist Binding, and Receptor–Response Coupling," *Life Sciences*, 56 (11/12):891–898 (1995) (Elsevier Science, Ltd., Editors).

Jacobi, et al. "Bis Heteroannulation. 2. Oxazole Alcohols from the Interaction of Lithiomethyl Isocyanide with Lactones. A Novel Synthesis of Evodone,", *J. Org. Chem.*, 46:2065–2069 (1981).

Jacobson, et al., "Molecular Probes for Muscarinic Receptors: Functionalized Congeners of Selective Muscarinic Antagonists," *Life Sciences*, 56(11/12):823–830 (1995) (Elsevier Science, Ltd., Editors).

Jaen, et al., "In Vitro and In Vivo Evaluation of the Subtype–Selective Muscarinic Agonist PD 151832," *Life Sciences*, 56(11/12):845–852 (1995) (Elsevier Science, Ltd., Editors).

Janson, et al., "Chronic nicotine treatment partly protects against the 1–methyl–4–phenyl–2,3,6–tetrahydropyridine–induced degeneration of nigrostriatal dopamine neurons in the black mouse," *Acta Physiol. Scand.*, 132:589–591 (1988).

Janson, et al., "GM1 ganglioside protects against the 1–methyl–4–phenyl–1,2,3,6–tetrahydropyridine–induced degeneration of nigrostriatal neurons in the black mouse," *Acta Physiol. Scand.*, 132:587–588 (1988).

Jarvik, "Beneficial effects of nicotine," *Br. J. of Addiction* 86:571–575 (1991).

Jenden, et al., "Summary and Closing Comments," *Life Sciences,* 56(11/12):993–1000 (1995) (Elsevier Science, Ltd., Editors).

Jick et al., "Cigarette Smoking and Ulcerative Colitis," *N. Engl. J. Med.*, 308(5):261–263 (1983).

Julia and Paris, "Syntheses A L'Aide De Sulfones $V^{(+)}$–Methode De Synthese Generale de Doubles Liaisons," *Tetrahedron Letters*, 49:4833–4836 (1973).

Jung and Rohloff, "Intramolecular Diels–Alder Chemistry of Pyrroles," J. *Chem. Soc., Chem. Comm.* pp. 630–632 (1984).

Kadaba, "Role of Protic and Dipolar Aprotic Solvents in Heterocyclic Synthesis via 1,3–Dipolar Cycloaddition Ractions," *Synthesis*, 71–84 (1973).

Kaye and Soreff, "The Psychiatrist's Role, Reponses, and Responsibilities When a Patient Commits Suicide," *Am. J. Psychiatry*, 148(6):739–743 (1991).

Kellar, "Epibatidine: Its Pharmacological Actions and Utility for Studying Neuronal Nicotinic Receptors," *Neurotransmissions*, XI(4):1–5 (1995).

Kilbinger, et al., "Prejunctional Muscarinic Receptors Regulating Neurotransmitter Release in Airways," *Life Sciences*, 56(11/12):981–987 (1995).

Kozikowsky and Li, "A Nitrile Oxide Based Entry to 2,3–Dihydropyran–4–ones. Synthesis of a Protected Version of "compactin Lactone" in Racemic and Optically Active Forms," *J. Org. Chem.*, 50:778–785 (1985).

Kotsuki, H., et al., "High–Pressure Reactions of Pyrroles with Dimethyl cetylenedicarboxylate," *Heterocyles*, 19:1915–1920 (1982).

Kricka and Vernon, "Nitrogen–Bridged Six–Membered Ring Systems: 7–Azabicyclo[2.2.1]hepta–2,5–dienes, Naphthalen–I,4–imines, and Anthracen–9,10–imines," *Adv. in Heterocycl. Chem.*, 16:87–121 (1974).

Krow, et al., "Homoepibatidines. syn–6– and syn –5(6–Chloro–3–pyridyl)isoquinuclidines. Potent Nicotinic Receptor Ligands," *Tetrahedron Letters* (In Press 1996).

Kuhar, M.J., et al. "3-β-(4-idophenyl-tropan-2-β-carboxylic acid methyl ester tartrate and Related Compounds as Cocaine Receptor-Binding Ligands," *Chem. Abst.*, 116(7):447 (1992) 55131n.

Lambrecht, et al., "The Design and Pharmacology of Novel Selective Muscarinic Agonists and Antagonists," *Life Sciences*, 56(11/12):815–822 (1995) (Elsevier Science, Ltd., Editors).

Larock and Johnson, "Palladium–catalysed Intermolecular Arylation and Alkenylation of Bicyclic Alkenes," *J. Chem. Soc. Chem. Comm.*, 1368–1370 (1989).

Lashner et al., "Testing Nicotine Gum for Ulcerative Colitis Patients," *Digest. Dis. Sci.*, 35(7):827–832 (1990).

Lee, J.W. and Oh, D.Y., "Conversion of B–Oxo Sulfones into Acetylenic Sulfones," *Synlett*, pp. 290 (1990).

Leroy, et al., "Synthesis of 3,4–Bis[trifluoromethyl]–1 H –pyrrole," *Synthesis*, 313–315 (1982).

Li, et al., "The Analgesic Effect of Epibatidine and Isomers," *Bioorg. and Med. Chem. Letters*, 3:2759–2764 (1993).

Lichtensteiger, et al., "A Quantitative Correlation Between Single Unit Activity and Fluorescence Intensity of Dopamine Neurones in Zona Compacta of Substantia Nigra, as Demonstrated Under the Influence of Nicotine and Physostigmine," *Brain Res.*, 117:85–103 (1976).

Linde, et al., "Straightford Synthesis of 1,2,3–Tricarbonyl Systems," *J. Org. Chem.*, 56:2534–2538 (1991).

McPherson, et al., "Resolution and in Vitro and Initial In Vivo Evaluation of Isomers of Iodine–125–Labeled 1–Azabicyclo[2.2.2]oct–3–yl a–Hydroxy–a–(1–iodo–1–propen–3–yl)–a–phenylacetate: A High–Affinity Ligand for the Muscarinic Receptor," *J. Med. Chem.*, 38:3908–3917 (1995).

Melchiorre, et al., "The Design of Novel Methoctramine–Related Tetraamines as Muscarinic Receptor Subtype Selective Antagonists," *Life Sciences*, 56(11/12):837–844 (1995) (Elsevier Science, Ltd., Editors).

Moll, *Brit Med. J.*, 1: 1079 (1926).

Moss et al., "Nicotine and Cannabinoids as Adjuncts to Neuroleptics in the Treatment of Tourette Syndrome and Other Motor Disorders," *Life Sciences*, 44:1521–1525(1989).

Myers, W.H., et al., "Tautomerizations, Protonations, and Electrophilic Additions of $n^2$–Coordinated Pyrroles," *J. Am. Chem. Soc.*, 114(14):5684–5692 (1992).

Numa et al. "Molecular Structure of the Nicotinic Acetylcholine Receptor," *Cold Spring Harbor Symp. Quant. Biol.*, 48:57–69 (1983).

Onali and Olianas, "Bimodal Regulation of cyclic Amp by Muscarinic Receptors Involvement of Multiple G Proteins and Different Forms of Adenylyl Cyclase," *Life Sciences*, 56(11/12):973–980 (1995) (Elsevier Science, Ltd., Editors).

Orlek, et al., "Design and Synthesis of Novel Muscarinic Agonists Containing the 1,2,4–Triazine Ring as an Ester Bioisostere," *Bioorgan.& Med. Chem. Letters*, 4(12):1411–1414 (1994).

Peralta, "Dual Modulation of a Potassium Channel by the M1 Muscarinic and B2–Adrenergic Receptors," *Life Sciences*, 56(11/12):957–964 (1995).

Qian, C.; et al., "Epibatidine is a nicotinic analgesic," *European J. Pharmacology*, 250(3):R–13–14 (1993).

Qian, et al., "Acetylcholine Muscarinic Receptor Regulations of the RAS/RAF/Map Kinase Pathway," *Life Sciences*, 56(11/12):945–949 (1995).

Qian, et al., "Effects of Epibatidine on Body Weight in Mice," *Med. Chem. Res.*, 4:493–501 (1994).

Reavill, "Action of nicotine on dopamine pathways and implications for Parkinson's disease," *Nicotine Psychopharmacology*, (Wonnacott, et al., Editors, Oxford University Press, 9:307–340 (1990).

Rhodes and Thomas, "Nicotine Treatment in Ulcerative Colitis," *Drugs*, 49(2):157–160 (1995).

Russell, et al., "Theoretical Background and Clinical Use of Nicotine Chewing Gum," *National Institute on Drug Abuse Research Monograph Series* 110–130 (1985).

Sahley et al., "Antinociceptive Effects of Central and Systemic Administration of Nicotine in the Rat, " *Psychopharmacology*, 65:279–283 (1979).

Sakamoto, T., et al., "A Facile Synthesis of Ethynyl–Substiuted Six–Membered N –Heteroaromatic Compounds," *Synthesis*, pp. 312, (1983).

Sanberg et al., "Nicotine potentiates the effects of haloperidol in animals and in patients with Tourette syndrome," *Biomedicine and Pharmacotherapy*, 43:19–23 (1989).

Sauerberg, et al., "Muscarinic Agonists as Analgesics. Antinociceptive Activity Versus $M_1$ Activity:SAR of Alkylthio–TZTP's and Related 1,2,5–Thiadiazole Analogs," *Life Sciences*, 56(11/12):807–814 (1995) (Elsevier Science, Ltd., Editors).

Sawyer and Narayanan, "Deacylation of Alkyl Carbamates: Selective Deprotection of Secondary Amines," *Syn. Comm.*, 13:135–138 (1983).

Schwarz, et al., "Mutations of Aspartate 103 in the Hm2 Receptor and Alterations in Receptor Binding Properties of Muscarinic Agonists," *Life Sciences*, 56(11/12):923–929 (1995).

Sheppard, et al., "3–(2–(3–Pyridinyl)thiazolidin–4–oyl)Indoles, a Novel Series of Platelet Activating Factor Antagonists," *J. Med. Chem.*, 37:2011–2032 (1994).

Showell, et al., "L–696,986: A Functionally Selective and Potent Muscarinic $M_1$ Receptor Partial Agonists," *Medicinal Chem. Res.*, 3:171–177 (1993).

Spande, et al., "Epibatidine: A Novel (Chloropyridyl)Azabicycloheptane with Potent Analgesic Activity from an Ecuadoran Poison Frog," *Org. Chem.* 5:332–335 (1992).

Spande, et al., "Epibatidine,: A Novel (Chloropyridyl) azabicycloheptane with Potent Analygesic Activity from an Ecuadoran Poison Frog," *J. Am. Chem. Soc.*, 114:3475–3478 (1992).

Steinbach and Ifune, "How many kinds of nicotinic acetylcholine receptor are there?" *Trends Neurosci.*, 12:3–6 (1989).

Stinson, S., "Osmium(III) Found to Disrupt Aromaticity," *Chemical and Engineering News*, pp. 27–30 (Nov. 1992).

Taylor, "Agents Acting at the Neuromuscular Junction and Autonomic Ganglia," *The Pharmacological Basis of Therapeutics*, (Goodman and Gilman, Editors, Pergamon Press, 9:166–186 (1990).

Thomsen, et al., "Preparation of B–Keto Sulfones from [(Phenylsulfonyl)methylene]dilithium and Acid Chlorides," *J. Org. Chem.*, 53:906–907 (1988).

Tobin et al., "Cigarette Smoking and Inflammatory Bowel Disease," *Gastroenterology*, 93:316–321 (1987).

Toube, T.P., "1.9 Cycloaddition Reactions of Acylpyrroles and Their Derivatives," *Pyrroles*, Part 2, (Jones, R. A., ed.) John Wiley, New York, pp. 92–95 (1992).

Tripathi et al., "Nicotine–Induced Antinociception in Rats and Mice: Correlation with Nicotine Brain Levels," *J. Pharmacol. Exp. Ther.*, 221(1):91–96 (1982).

Trost, B.M., et al., "Desulfonylation of Aryl Alkyl Sulfones," *Tetrahedron Lett.*, pp. 3477–3478 (1976).

Tsukamoto, et al., "Synthesis and Structure–Activity Studies of a Series of Spirooxazodine–2,4–diones: 4–Oxa Analogues of the Muscarinic Agonist 2–Ethyl–8–methyl–2, 8–iazaspiro[4.5]decane–1,3–dione," *J. Med. Chem.*, 36:2292–2299 (1993).

Volle, *Pharmacology of Ganglionic Transmission*, Kharkevich, D.A., ed., Springer–Verlag, Berlin, pp. 281–312 (1980).

Wani, M.C., et al.,, "Plant Antitumor Agents. IX. The Total Synthesis of dl –Camptothecin," *J. Am. Chem. Soc.*, 94:3631–3632 (1972).

Ward, et al., "Functionally Selective $M_1$ Muscarinic Agonists. 3. Side Chains and Azacycles Contributing to Functional Muscarinic Selectivity among Pyrazinylazacyles," *J. Med. Chem.*, 38:3469–3481 (1995).

Wess, et al., "Muscarinic Acetylcholine Receptors: Structural Basis of Ligand Binding and G Protein Coupling," *Life Sciences*, 56(11/12):915–922 (1995) (Elsevier Science, Ltd., Editors).

Williams, et al., "Neuronal Nicotinic Acetylcholine Receptors," *Drug News& Perspectives* 7(4):205–223 (1994).

7 R = Cl
11 R = OMe
12 R = H

7-AZABICYCLO[2.2.1]-HEPTANE AND -HEPTENE DERIVATIVES AS CHOLINERGIC RECEPTOR LIGANDS

This application claims the benefit of U.S. Provisional Application No. 60/002,551 filed on Aug. 21, 1995.

This invention is in the area of 7-azabicyclo[2.2.1] heptane and -heptene derivatives and their method of manufacture and pharmaceutical use.

BACKGROUND OF THE INVENTION

Opiates, and in particular, morphine, are routinely admininstered for the treatment of moderate to severe pain. Agents that are less potent than morphine, such as codeine, mixed agonist-antagonist opioids, and non-opiate analgesics, including non-steroidal anti-inflammatory drugs (NSAIDS) are often used to relieve mild to moderate pain. Because of the well-known side effects of opiates, including chemical dependence and respiratory depression, there is a strong need for a non-opiate based analgesic for moderate to severe pain that would equal or exceed the potency of opiate analgesics, yet lack the serious side effects associated with the administration of opiates.

Spande, et al., reported in 1992 that a potent nonopiate analgesic had been isolated from the skins of the Ecuadoran poison frog, *Epipedobates tricolor.* Spande, et al., 1992 *J. Am. Chem. Soc.,* 114, 3475–3478. The structure of the compound was determined by mass spectroscopy, infrared spectroscopy, and nuclear magnetic resonance as exo-2-(2-chloro-5-pyridyl)-7-azabicyclo [2.2.1]heptane (see FIG. 1). The compound, which was named epibatidine, is the first member of the class of 7-azabicyclo[2.2.1]heptane compounds to be found in nature. Limited pharmacological evaluation of epibatidine indicated that it is approximately 500 times more potent that morphine in eliciting the Straub-tail response, and that this effect is not reversed by the opiate antagonist naloxone. In the hot plate analgesia assay, epibatidine is approximately 200 times as potent as morphine. It has also been determined that epibatidine has a negligible affinity for opiate receptors (1/8000 times that of morphine). Based on this data, it appears that epibatidine is a very potent analgesic that acts via a non-opiate mechanism.

In 1993, it was reported that epibatidine is a nicotinic cholinergic receptor agonist. Qian, C.; Li, T.; Shen, T. Y.; Libertine, G. L.; Echman, J.; Biftu, T.; Ip, S. Epibatidine is a nicotinic analgesic. *European J. Pharmacology,* 1993, 250(3):R-13–14; Fletcher, S.; Baker, R.; Chambers, M. M.; Herbert, R. H.; Hobbs, S. C.; Thomas, S. R.; Veerler, H. M.; Watt, A. P.; Ball, R. G. Total synthesis and determination of the absolute configuration of epibatidine. *J. Org. Chem.,* 1994, 59(7):1771–1778; Baldio, B.; Daly, J. W.; Epibatidine. A potent analgetic and nicotinic agonist. *FASEB Journal,* 1994, 8(4–5):A875. *Mol. Pharmacol.,* 1994, 45:5361–569; Dukat, M.; Damaj, M. I.; Glassco, W.; Dumas, D.; May, E. I.; Martin, B. R.; Glennon, R. A. Epibatidine: A very high affinity nicotine-receptor ligand. *Medicinal Chem. Res.,* 1994, 4:131–139.

Cholinergic receptors play an important role in the functioning of muscles, organs and generally in the central nervous system. There are also complex interactions between cholinergic receptors and the function of receptors of other neurotransmitters such as dopamine, serotonin and catecholamines.

Acetylcholine (ACh) serves as the neurotransmitter at all autonomic ganglia, at the postganglionic parasympathetic nerve endings, and at the postganglionic sympathetic nerve endings innervating the eccrine sweat glands. Different receptors for ACh exist on the postganglionic neurons within the autonomic ganglia and at the postjunctional autonomic effector sites. Those within the autonomic ganglia and adrenal medulla are stimulated predominantly by nicotine and are known as nicotinic receptors. Those on autonomic effector cells are stimulated primarily by the alkaloid muscarine and are known as muscarinic receptors.

The nicotinic receptors of autonomic ganglia and skeletal muscle are not homogenous because they can be blocked by different antagonists. For example, d-tubocurarine effectively blocks nicotinic response in skeletal muscle, whereas hexamethonium and mecamylamine are more effective in blocking nicotinic responses in autonomic ganglia. The nicotinic cholinergic receptors are named the $N_M$ and $N_N$ receptors, respectively.

Muscarinic receptors are divided into at least four subtypes (M-1 through M-4). An M-5 receptor has been cloned in human cells. The M-1 receptor is localized in the central nervous system and perhaps parasympathetic ganglia. The M-2 receptor is the non-neuronal muscarinic receptor on smooth muscle, cardiac muscle and glandular epithelium. Muscarinic receptors can be blocked by administration of atropine. Bethanechol is a selective agonist for the M-2 receptor and pirenzepine is a selective antagonist of the M-1 receptor.

In light of the fact that epibatidine is a strong cholinergic receptor ligand, it would be of interest to provide new 7-azabicyclo[2.2.1]-heptane and -heptene derivatives with pharmacological activity.

Therefore, it is an object of the present invention to provide new 7-azabicyclo[2.2.1]-heptane and -heptene derivatives with analgesic, anti-inflammatory and other pharmaceutical activities.

It is a further object of the present invention to provide compounds which are cholinergic receptor ligands.

It is still another object of the present invention to provide compounds which are agonists and antagonists of muscarinic and nicotinic receptors.

It is still another object of the present invention to provide new methods for the treatment of pain.

It is another object of the present invention to provide compositions and methods for the treatment of cognitive, neurological, and mental disorders, as well as other disorders characterized by decreased or increased cholinergic function.

SUMMARY OF THE INVENTION 7-azabicyclo[2.2.1]-heptane and -heptene compounds are disclosed of Formula (I):

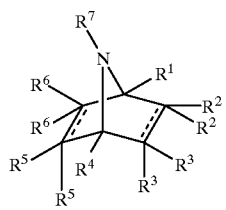

wherein:

$R^1$ and $R^4$ are independently hydrogen, alkyl, including $CH_3$; alkylhydroxy, including $CH_2OH$; alkyloxyalkyl, including —$CH_2OCH_3$; alkylthioalkyl, including —$CH_2SCH_3$; alkylamino, including —$CH_2NH_2$; alkylaminoalkyl or alkylaminodialkyl, including $CH_2NH(CH_3)$ and $CH_2N(CH_3)_2$; oxyalkyl, including —$OCH_3$; carboalkoxy, including carbomethoxy; allyl, aryl and thioalkyl, including —$SCH_3$;

$R^3$, $R^5$ and $R^6$ are independently hydrogen, alkyl, including —$CH_3$; alkylhydroxy, including —$CH_2OH$; alkyloxyalkyl, including —$CH_2OCH_3$; alkylthioalkyl, including —$CH_2SCH_3$; alkylamino, including —$CH_2NH_2$; alkylaminoalkyl or alkylaminodialkyl, including $CH_2NH(CH_3)$ and $CH_2N(CH_3)_2$; oxyalkyl, including —$OCH_3$; thioalkyl, including —$SCH_3$; halo, including Cl, F; haloalkyl, including $CF_3$; $NH_2$, alkylamino or dialkylamino, including —$N(CH_3)_2$ and —$NHCH_3$; cyclic dialkylamino, including

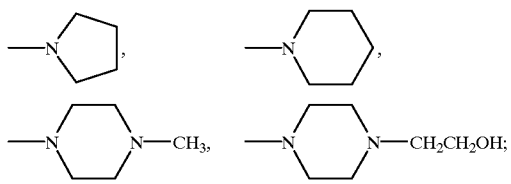

amidine, cyclic amidine including

and their N-alkyl derivatives;

—$CO_2H$; $CO_2$alkyl, including —$CO_2CH_3$; —C(O)alkyl, including —$C(O)CH_3$; —CN, —$C(O)NH_2$, —C(O)NH(alkyl), —$C(O)N(alkyl)_2$, including —$C(O)N(CH_3)_2$; allyl, —$SO_2$(alkyl), —$SO_2$aryl, including —$SO_2(C_6H_5)$, —S(O)alkyl, —S(O)aryl, aryl, heteroaryl;

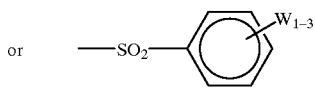

$R_5$ and $R_6$ together can be alkylidene or haloalkylidene, including —$CH_2$— and —$CF_2$—; epoxide (—O—); episulfide (—S—); imino (—N(alkyl)— or —N(H)—) or a fused aryl or heteroaryl ring including a fused phenyl ring;

$R_2$ is independently hydrogen, alkyl, including $CH_3$; alkenyl including —$CH_2$—$HC=CH_2$; alkylhydroxy, including —$CH_2$—OH; alkyloxyalkyl including —$CH_2$—O—(alkyl), alkylamine, including —$CH_2NH_2$; carboxylate, C(O)Oalkyl, including $CO_2Me$; C(O)Oaryl, C(O)Oheteroaryl, COOaralkyl, —CN, —NHC(O)$R^{12}$, —$CH_2NHC(O)R^{12}$, A, C(O)Q, -alkyl(Q), -alkenyl(Q), -alkynyl(Q), —O—(Q) —S—Q, —NH—Q or —N(alkyl)—Q;

$R_2$ and $R_3$ together can be —C(O)—$NR^8$—C(O) or CH(OH)—$N(R^8)$—C(O)— wherein $R^8$ can be alkyl, aryl including phenyl, or heteroaryl;

$R_7$ is hydrogen, alkyl, including $CH_3$, or $CH_2CH_3$; alkyl substituted with one or more halogens, including $CH_2CH_2Cl$; —$CH_2$—(cycloalkyl), including —$CH_2$—(cyclopropyl); —$CH_2CH=CH_2$, —$CH_2CH_2(C_6H_5)$, alkylhydroxy, including $CH_2CH_2OH$, alkylamino(alkyl)$_2$, including $CH_2CH_2N(CH_3)_2$ alkyloxyalkyl, alkylthioalkyl, aryl, dialkyl to form a quarternary ammonium including

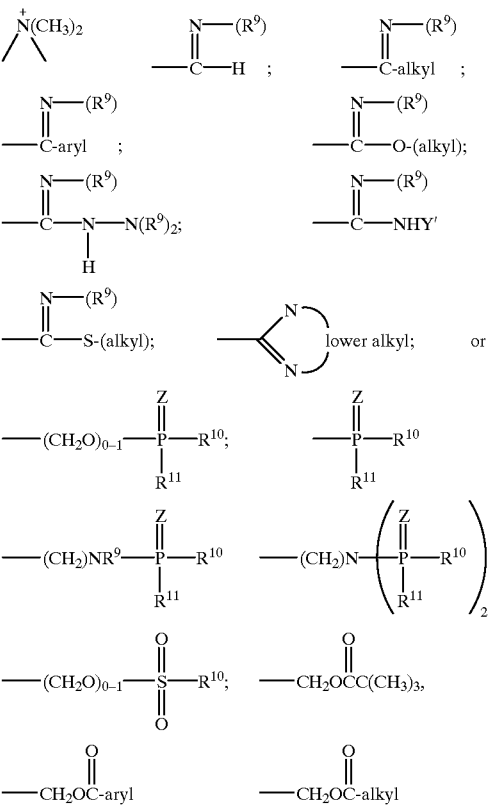

wherein $R^9$ is hydrogen or alkyl;
wherein Y' is CN, $NO_2$, alkyl, OH, —O-alkyl;
wherein Z is O or S;
wherein $R^{10}$ and $R^{11}$ are each independently —$O^-$, —OH, —O-alkyl, —O-aryl, —$NH_2$, —NH(alkyl), —$N(alkyl)_2$, —NH(aryl) and —$N(aryl)_2$;
wherein $R^{12}$ is alkyl, aryl, alkaryl, aralkyl, heteroaryl, alkenyl, alkynyl, and heteroaralkyl.

Q is

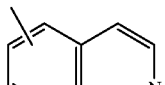

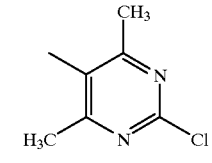

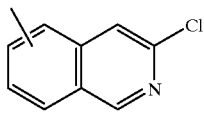

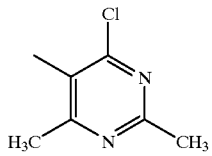

5
-continued
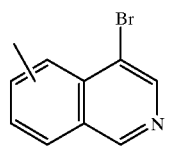
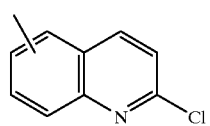
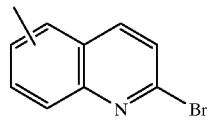
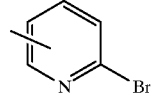
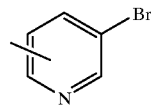
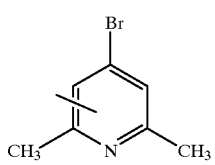
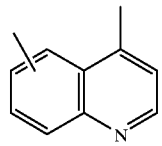
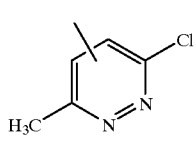
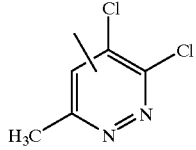
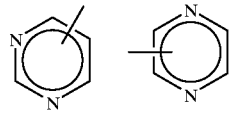
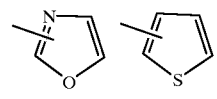
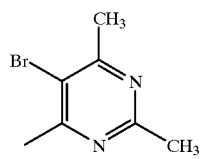
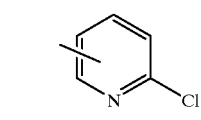
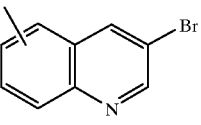
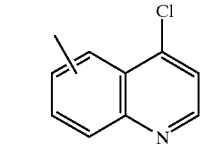
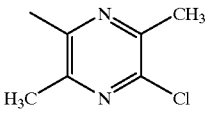
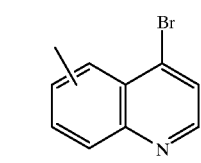
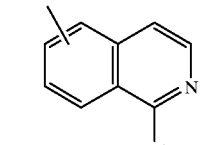
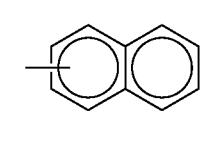
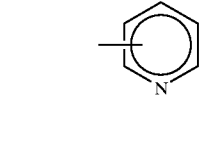
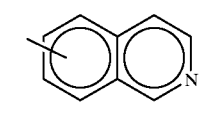
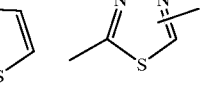
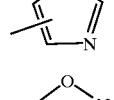
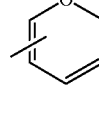
6
-continued
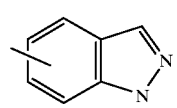
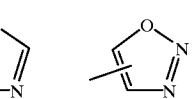
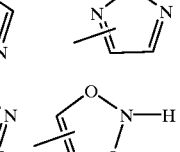
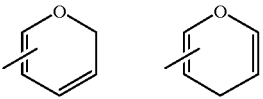
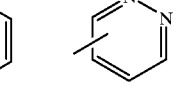
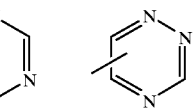
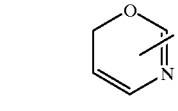
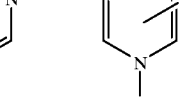
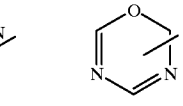
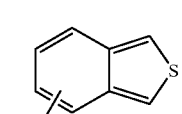
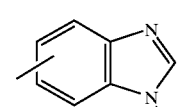

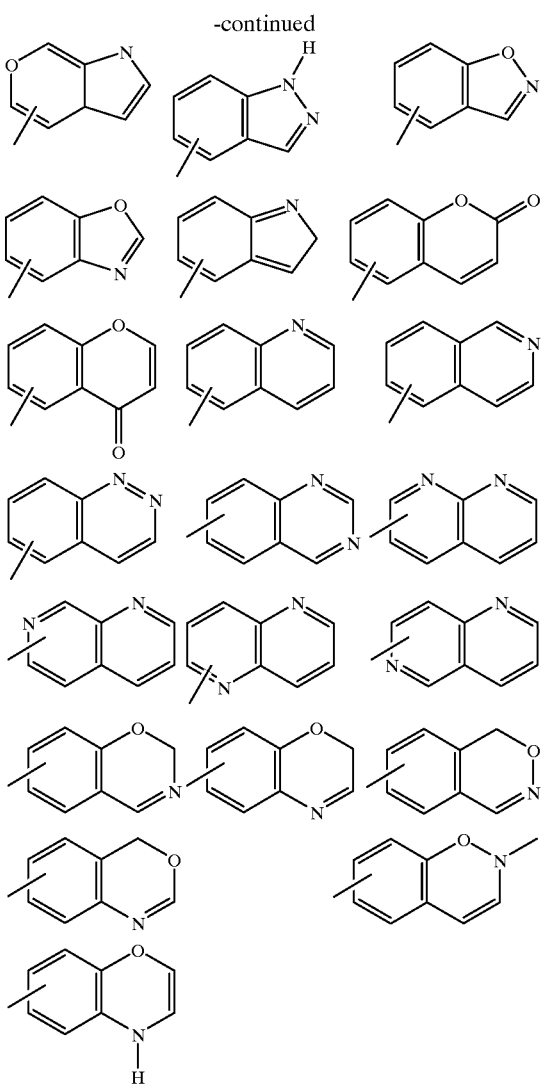

wherein the Q moiety can be optionally substituted with 1 to 3 W substituents; and W is alkyl, including $CH_3$; halo, including Cl and F; aryl, heteroaryl, OH, oxyalkyl, including —$OCH_3$; SH, thioalkyl, including —$SCH_3$; —SO(alkyl) including —$SOCH_3$; —$SO_2$alkyl, including —$SO_2CH_3$; —$OCH_2CH=CH_2$, —$OCH_2(C_6H_5)$, $CF_3$, CN, alkylenedioxy, including -methylenedioxy-; —$CO_2H$, —$CO_2$alkyl including —$CO_2CH_3$; —$OCH_2CH_2OH$, —$NO_2$, —$NH_2$, —NH(alkyl), including —$NHCH_3$; —$N(alkyl)_2$, including —$N(CH_3)_2$; —NHC(O)alkyl, including —$NHC(O)CH_3$; —$SO_2CF_3$, or —$NHCH_2$aryl, including —$NHCH_2(C_6H_5)$; —C(O) alkyl; —C(O)aryl; —C(O)aralkyl; —C(O)alkaryl; —C(O)heteroaryl; —$P(O)_2O^-M^+$ wherein M is a pharmaceutically acceptable cation; and wherein the ——— indicates an optional double bond.

These compounds are cholinergic receptor ligands, and thus act as nicotinic or muscarinic agonists or antagonists. Therefore, the compounds can also be used in the treatment of cognitive, neurological, and mental disorders, as well as other disorders characterized by decreased or increased cholinergic function.

The selectivity of the selected compound for for various receptor subtypes is easily determined by routine in vitro and in vivo pharmacological assays known to those skilled in the art, and described in more detail below. The receptor subtype selectivity is expected to vary based on the substituents on the 7-aza-norbornane or norbornene ring.

Compounds that act as nicotinic receptor agonists have central or peripheral analgesic activity, and, or alternatively, anti-inflammatory activity, and thus can be administered to a mammal, including a human, to treat pain and inflammatory disorders. A method for the treatment of pain is also presented that includes administering an effective amount of the compound or its pharmaceutically acceptable salt or derivative, or mixtures thereof, to a host in need of analgesic therapy, optionally in a pharmaceutically acceptable carrier or diluent.

DETAILED DESCRIPTION OF THE INVENTION

I. Definitions

Figure 1:
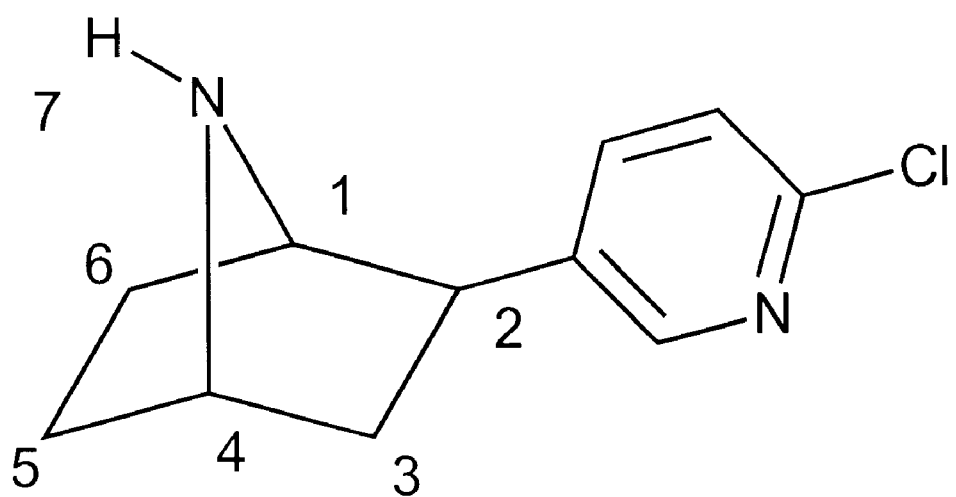
FIG. 1 is an illustration of the chemical structure of exo-2-(2-chloro-5-pyridyl)-7-azabicyclo[2.2.1]heptane (epibatidine).

The term alkyl, as used herein, refers to a saturated straight, branched, or cyclic (or a combination thereof) hydrocarbon of $C_1$ to $C_{10}$, and specifically includes methyl, ethyl, propyl, isopropyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term lower alkyl, as used herein, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, cyclopropylmethyl, pentyl, cyclopentyl, cyclobutylmethyl, isopentyl, neopentyl, hexyl, isohexyl, cyclohexyl, 3-methylpentyl, 2,2-dimethylbutyl, and 2,3-dimethylbutyl.

The term alkylamino refers to an amino group that has an alkyl substituent.

The term alkynyl, as referred to herein, refers to a $C_2$ to $C_{10}$ straight or branched hydrocarbon with at least one triple bond.

The term lower alkynyl, as referred to herein, refers to a $C_2$ to $C_6$ alkynyl group, specifically including acetylenyl and propynyl.

The term aryl, as used herein, refers to phenyl, or substituted phenyl, wherein the substituent is halo, alkyl, alkoxy, alkylthio, haloalkyl, hydroxyalkyl, alkoxyalkyl, methylenedioxy, cyano, C(O)(lower alkyl, carboxy, $CO_2$alkyl, amide, amino, alkylamino and dialkylamino, and wherein the aryl group can have up to 3 substituents.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined for aryl groups.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, pyrazinyl, benzofuranyl, quinolyl, iosquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a counteraction in a salt.

The term enantiomerically enriched composition or compound" refers to a composition or compound that includes at least 95%, and typically 98, 99, or 100 by weight of a single enantiomer of the compound.

The term pharmaceutically active derivative refers to any compound that upon administration to the recipient, is capable of providing directly or indirectly, the compounds disclosed herein.

As used herein, the term dipolarophile refers to a compound or moiety that reacts with a dipolar species to form a cycloaddition product.

As used herein, the term dienophile refers to a compound or moiety that reacts with a diene to form a cycloaddition product.

As used herein, the term η refers to a pi-orbital complex of an unsaturated compound with a metal, and wherein the superscript after the η refers to the number of $sp^2$ carbon atoms bonded to the metal.

The term electron withdrawing substituent as used herein refers to a substituent that pulls electron density from the moiety to which it is attached through induction or resonance. A wide variety of electron withdrawing substituents are well known to those skilled in organic synthesis.

II. Examples of Active Compounds

7-Azabicyclo[2.2.1]-heptane and -heptene derivatives of Formula (I) are provided that are cholinergic receptor ligands. These compounds typically act as nicotinic or muscarinic receptor agonists or antagonists. The compounds can be used in the treatment of cognitive, neurological, and mental disorders, as well as other disorders characterized by decreased or increased cholinergic function.

Some of the compounds have central and peripheral analgesic and, or alternatively, anti-inflammatory activity, and thus can be administered to a mammal, including a human, to treat pain and inflammation. A method for the treatment of pain is also presented that includes administering an effective amount of the compound or its pharmaceutically acceptable salt or derivative, or mixtures thereof, to a host in need of analgesic therapy, optionally in a pharmaceutically acceptable carrier or diluent.

The numbering scheme for 7-azabicyclo[2.2.1]-heptane and -heptene derivatives is as illustrated below.

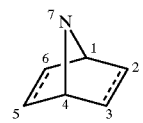

The 7-azabicyclo[2.2.1]-heptanes and -heptenes disclosed herein can exhibit a number of stereochemical configurations. As discussed above, the compounds are prepared in a Diels-Alder cycloaddition reaction of a dienophile with a pyrrole, or a modification of the Diels Alder reaction involving the reaction of a dipolarophile with a pentaammineosmium(II) activated pyrrole. In the transition state of the cycloaddition reaction, there are two possible relative orientations of the diene or dienophile, referred to as endo and exo. Endo configurations are formed when other unsaturated groups in the dienophile (or dipolarophile) lie near the developing double bond in the diene. Exo configurations are formed when other unsaturated groups in the dienophile (or dipolarophile) lie away from the developing double bond in the diene. Depending on the substitution on the carbon atoms, the endo and exo orientations can yield different stereoisomers.

Carbon atoms 2, 3, 5 and 6 in 7-azabicyclo[2.2.1]heptenes and carbon atoms 2 and 3 or 5 and 6 in 7-azabicyclo[2.2.1] heptenes are chiral when attached to different substituents. If at least one of the carbons in the molecule are chiral, the unsymmetrically substituted bicyclic compounds exist as one or more diastereomeric pairs. The R groups in the active compounds described herein can also include chiral carbons, and thus, optically active centers.

It is sometimes found that one or more enantiomers of a biologically active compound is more active, and perhaps less toxic, than other enantiomers of the same compound. Such enantiomerically enriched compounds are preferred for pharmaceutical administration to humans or other hosts.

One of ordinary skill in the art can easily separate the enantiomers of the disclosed compounds using conventional processes, and can evaluate the biological activity of the isolated enantiomers using methods disclosed herein or otherwise known. Through the use of chiral NMR shift reagents, polarimetry, or chiral HPLC, the optical enrichment of the compound can be determined.

Classical methods of resolution include a variety of physical and chemical techniques. For example, since the compound has a basic amine ($N^7$), it can be reacted with a chiral acid to form diastereomeric salts that may possess significantly different solubility properties. Nonlimiting examples of chiral acids include malic acid, mandelic acid, dibenzoyl tartaric acid, 3-bromocamphor-B-sulfonic acid, 10-camphorsulfonic acid, and di-p-toluoyltartaric acid, and (−)-menthyl chloroformate. Similarly, acylation of a free amine or hydroxyl group in the molecule with a chiral acid also results in the formation of a diastereomeric amide or ester whose physical properties may differ sufficiently to permit separation. Enantiomerically pure or enriched compounds can be also obtained by passing the racemic mixture through a chromatographic column that has been designed for chiral separations, including cyclodextrin bonded columns marketed by Rainin Corporation.

Chiral benzylated pyrrole complexes such as [Os(NH$_3$)$_5$ ($^2$-(ArRHC—(pyrrole)))]$^{2+}$) can be used for enantioselective syntheses of 7-azanorbornanes.

The following are nonlimiting examples of specific compounds that fall within the scope of the invention. These examples are merely exemplary, and are not intended to limit the scope of the invention.

(A) Epibatidine isomers:

1-7-aza-2-exo-(2-chloro-5-pyridyl)-bicyclo[2.2.1] heptane and its pharmaceutically acceptable salts, including the hydrochloride salt; 1-7-aza-2-exo-(2-chloro-5-pyridyl)-bicyclo[2.2.1] heptane and its pharmaceutically acceptable salts, including the hydrochloride salt; d and 1-7-aza-endo-(2-chloro-5-pyridyl)-bicyclo[2.2.1]heptane and its pharmaceutically acceptable salts, including the hydrochloride salts;

(B) d and l enantiomers of the 7-aza-bicyclo[2.2.1] heptane derivatives containing the following substituents:

A combination of 7-methyl, 7-allyl-, 7-cyclopropylmethyl, 7-cyclobutylmethyl, 7-phenethyl, 7-hydroxyethyl, 7-methoxyethyl, 7-methylthioethyl, 7-dimethylaminopropyl, 7-formamidinyl, 7-(2-chloroethyl), 7-disodium phosphate and 7-(4-methoxybenzyl) substituents with a 2-exo-(2-chloro-5-pyridyl) substituent; 2-exo-(3-pyridyl); 2-endo-(3-pyridyl); 7-methyl-2-exo-(3-pyridyl); 7-cyclopropylmethyl-2-exo-(3-pyridyl); 7-phenethyl-2-exo-(3-pyridyl); 2-exo-(4-pyridyl); 7-methyl-2-exo-(4-pyridyl); 7-allyl-2-exo-(4-pyridyl); 7-cyclopropylmethyl-2-exo-(4-pyridyl); 2-exo-(3-chloro-4-pyridyl); 7-cyclopropylmethyl-2-exo-(3-chloro-4-pyridyl); 7-phenethyl-2-exo-(3-chloro-4-pyridyl) 2-exo-(2chloro-3-pyridyl); 2-exo-(2-chloro-4-pyridyl); 2-exo-(2-fluoro-5-pyridyl); 2-exo-(2-methoxy-5-pyridyl); 2-exo-(2-methylthio-5-pyridyl); 2-exo-(2-methyl-5-pyridyl); 2-exo-(2-dimethylamino-5-pyridyl); 2-exo-(2 -hydroxy-5-pyridyl) and their 7-cyclopropylmethyl derivatives;

The exo and endo isomers of: 2-phenyl; 2-(3-chlorophenyl); 2-(3-dimethylaminophenyl); 2-(3-trifluoromethylphenyl); 2-(3,4-methylenedioxyphenyl); 2-(3,4-dimethoxyphenyl); 2-(4-fluorophenyl); 2-(4-hydroxyphenyl); 2-(4-methylthiophenyl); 2-(4-methylsulfonylphenyl), 2-(3,5-difluorophenyl); 2-(2-chlorophenyl); 2-(2-naphthyl); 2-(7methoxy-2-naphthyl); 2-(5-chloro-2-thienyl); 2-(chloro-5-thiazolyl); 2-(4-pyrimidyl); 2-(2-chloro-5-pyrimidyl); 2-(5-chloro-2-pyridazinyl); 2-(1,2,5-thiadiazol-3-yl); 2-(5-dimethylamino-2-furyl); 2-(5-indolyl); 2-(5-fluoro-3-indolyl); 2-(5-methoxy-3-indolyl); 2-(4-chlorobenzyl); 2-(5-chloro-3-pyridylmethyl); 2-(4-pyridylmethyl; 2-nicotinyl; 2-(6-chloronicotinyl); 2-isonicotinyl; 2-(3-chloro-isonicotinyl); 2(4-chlorobenzoyl); 2-(4-dimethylaminobenzoyl); 2-(3,4-dimethoxybenzoyl) and their 7-methyl, 7-cyclopropylmethyl, 7-allyl and 7-phenethyl derivatives;

(C) The exo and endo isomers of 7-aza-2-(2-chloro-5-pyridyl)-bicyclo[2.2.1]heptane containing the following substituents at the 1, 2, 3, 4, 5 or 6 positions:

1 or 4-methyl; 1 or 4-hydroxymethyl; 1 or 4- methoxymethyl; 1 or 4-carbomethoxy; 1 or 4-allyl; 1 or 4-benzyl; 1 or 4-(4-fluorobenzyl); 1 or 4-(4-methoxybenzyl); 1,4-dimethyl; 1,4-bis(hydroxymethyl); 1,4-bis(methoxymethyl); 1,6 or 4,5-butylidene;

Endo or exo-3-methyl; 3-hydroxymethyl; 3-methoxymethyl; 3-carbomethoxy; 3-carboxy; 3-carbamyl; 3-cyano; 3-acetyl; 3-aminomethyl; 3-dimethylaminomethyl; 3-methylthiomethyl; 3-phenylsulfonyl; 3-methanesulfonyl; 3-benzyl; 3-allyl; 3-cyano-1,4-dimethyl; 3-hydroxymethyl-1,4-dimethyl, 3-methoxymethyl-1,4-dimethyl; 3-methylthiomethyl-1,4-dimethyl; 5,6-bis(trifluoromethyl); 5 or 6-methoxy; 5 or 6-methyl; 5,6-dimethyl; 5,6-dicarbomethoxy; 5,6-bis(hydroxymethyl); 5,6-bis (methoxymethyl); 5 or 6-chloro; 5 or 6-hydroxy; 5,6-dehydro; 5,6-dehydro-1,4-dimethyl; 3,3-dimethyl; 2-methyl; 2,3-dimethyl, 5,6-methylene; and their corresponding 7-methyl, 7-cyclopropylmethyl, 7-allyl, 7-phenethyl and 7-(4-fluorobenzyl) derivatives.

(D) 7-Aza-2-(2-chloro-5-pyridyl)-bicyclo[2.2.1]hept-2-ene and its 7-methyl, 7-allyl, 7-cyclopropylmethyl, 7-phenethyl and 7-(4-methoxyphenethyl) derivatives; and the corresponding 1,4-dimethyl; 1 or 4-methyl; 5,6-dimethyl and 5,6-bis(trifluoromethyl) analogs.

(E) Benzo[5a,6a]epibatidine and its N-methyl derivative; 2,3-dehydroepibatidine; 5,6-bis(trifluoromethyl) deschloroepibatidine; 2-carbomethoxy-7-methyl-7-azabicyclo[2.2.1]heptane; 2-cyano-7-methyl-7-azabicyclo [2.2.1]heptane; trans-2,3-bis-carbomethoxy-7-azabicyclo [2.2.1]- heptane; exo-2-amino-7-methyl-7-azabicyclo [2.2.1]- heptane; exo-2-(1-pyrrolylmethyl)-7-methyl-7-azabicyclo [2.2.1] heptane; exo-2-hydroxymethyl-7-methyl-7-azabicyclo[2.2.1]heptane; exo-2-hydroxymethyl-7-methyl-2-azabicyclo[2.2.1]heptane.

(F) exo-2-acetamidomethyl-7-methyl-7-azabicyclo[2.2.1] heptane; exo-2-benzamidomethyl-7-methyl-7-azabicyclo [2.2.1]heptane; N-[exo-2-(7 -methyl-7-azabicyclo[2.2.1]-heptyl)methyl]-N$^1$-phenyl urea; exo-2,5'-(3'-methyl-1',2',4'-oxadiazolyl)-7-methyl-7-azabicyclo[2.2.1]heptane; exo-2, 5'-(3'-methyl-1',2',4'-oxadiazolyl)-1,4-dimethyl-7-azabicyclo[2.2.1]heptane; endo-2,5'-(3'-methyl-1',2',4'-oxadiazolyl)-7-methyl-7-azabicyclo[2.2.1]heptane; exo-2, 5'-(3'[4'-methoxyphenyl]-1,40 ,2',4'-oxadiazolyl)-7-methyl-7-azabicyclo[2.2.1]heptane; endo-2,2'-(5'-methyl-1',3',4'-oxadiazolyl)-7-methyl-7-azabicyclo[2.2.1]heptane; exo-2, 2'-(5'-methyl-1', 3',4'-oxadiazolyl)-7-methyl-7-azabicyclo [2.2.1]heptane; 2-carbomethoxy-7-(3',5'-dimethylbenzyl)-7-azabicyclo[2.2.1]heptane; 2-carbomethoxy-7-azabicyclo [2.2.1]heptane; (±)-(exo)-7-(1,1-dimethylethoxycarbonyl)-7-azabicyclo[2.2.1]heptan-2-one; (±)-7-(1,1-dimethylethoxycarbonyl)-7-azabicyclo[2.2.1]-heptan-2-ylidene; (±)-(exo)-7-(1,1-dimethylethoxycarbonyl)-2 -hydroxymethyl-7-azabicyclo[2.2.1]heptane; (±)-(exo)-7-(1,1-dimethylethoxycarbonyl)-2-formyl-7-azabicyclo[2.2.1] heptane; (±)-(exo)-2-[1'-(2',2'-dibromo-1'-ethenyl)]-7-(1,1-dimethylethoxycarbonyl)-7-azabicyclo[2.2.1]heptane; (±)-(exo)-2-(1'-ethynyl)-7-(1,1-dimethylethoxycarbonyl)-7-azabicyclo[2.2.1]heptane; (±)-7-(dimethylethoxycarbonyl)-2-[5'-(3'-methyl)isoxazolyl]-7-azabicyclo[2.2.1]heptane; 2-[5'-(3'-methyl)isoxazolyl]-7-azabicyclo[2.2.1]heptane; 2-[5'-(3'-methyl)isoxazolyl]-7-azabicyclo[2.2.1]heptane; (±)-(exo)-7-(methoxycarbonyl)-2-(2'-quinolyl)-7-azabicyclo[2.2.1]heptane; (±)-(exo)-2-(2'-quinolyl)-7-azabicyclo[2.2.1]heptane; (±)-(exo)-7-methyl-2-(2'-quinolyl)-7-azabicyclo[2.2.1]heptane; 2-(5'-oxazole)-7-methyl- 7-azanorbornane; 2-(1',3',4'-oxadiazole)-7-methyl-7-azanorbornane; 2-(tetrazole)-7-methyl-7-azanorbornane; 2-(imidazole)-7-methyl-7-azanorbornane; 2-(benzopyrimidinone)-7-methyl-7-azanorbornane; 2-(acylamino)-7-methyl-7-azanorbornane and 2-(acylaminomethyl)-7-methyl-7-azanorbornane.

III. Methods for the Synthesis of Optionally Substituted 7-Azabicyclo[2.2.1]-Heptanes and -Heptenes A. Synthesis of the 7-Azabicyclo[2.2.1]-Heptane or -Heptane Ring System from Pyrroles Via Pentaammineosmium(II) Complexes It has been discovered that 7-azabicyclo[2.2.1]-heptane and -heptene derivatives can be prepared by combining a dipolarophile with an optionally substituted pyrrole that has been complexed with pentaammineosmium(II).

Any dipolarophile can be used in this reaction that reacts with the pentaammineosmium pyrrole complex to provide an optionally substituted 7-azabicyclo[2.2.1]-heptene, which is easily converted to the corresponding 7-azabicyclo [2.2.1]-heptane. Examples of dipolarophiles include compounds of the structure $Z_1$—C≡C—$Z_2$, wherein $Z_1$ and $Z_2$ are independently electron withdrawing groups, including without limitation, esters, nitriles, ketones, aldehydes, amides, —$NO_2$, sulfones, anhydrides, —$CF_3$, pyridinium salts, and for example, CO(alkyl, aryl or heteroaryl), C(O)H, $CO_2$(alkyl, aryl, or heteroaryl), $SO_2$(alkyl, aryl, or heteroaryl), or wherein $Z_1$ and $Z_2$ are together $(CO)_2O$, or $(CO)_2N$. Specific compounds include N-methylated and 6-carboxylated pyridyl acrylates, alkyl acrylate, alkyl methacrylate, pyridyl substituted vinyl sulfones, acrylonitriles, anhydrides, maleimides, alpha-methylene-δ-butyrolactone, maleates, and fumarates.

Analogously, any optionally substituted pyrrole can be used that on complexation with pentaammineosmium(II) will react with a dipolarophile. Examples of suitable pyrroles include 2,5-dialkylpyrrole, 2-alkylpyrrole, 3-alkylpyrrole, 1-alkylpyrrole, 3,4-dialkylpyrrole, pyrrole, 1-silylated pyrrole, (1, 2, or 3)alkoxy or amino pyrrole, 2,3-dialkoxypyrrole, 2,5-dialkoxypyrrole, and 3,4-dialkoxypyrrole.

As shown below in Scheme 1, a complex is readily formed between pyrrole and the π-base pentaammineosmium(II) in which the osmium coordinates the heterocycle across C2 and C3. At 20° C., this species is in equilibrium with its linkage isomer in which the metal binds across C3 and C4. Although the 3,4-η species is only a minor component ($\Delta G_{iso} > 3$ kcal/mol), the metal coordination in this species renders the remaining portion of the pyrrole an azomethine ylide ($R_2C^+$—N(R)—C—$R_2 \leftrightarrow R_2C=N^+(R)$—$C^-R_2$), and thereby dramatically enhances the tendency of the ligand to undergo a 1,3-dipolar cycloaddition with suitable dipolarophiles.

while keeping the bicyclic framework intact. For example, derivatization of electron-withdrawing groups in the 2- or 3-positions of the norbornene framework, using conventional processes, provides a wide array of functionalized 7-azanorbornenes. Specifically, as shown in Scheme 2 below, the exo-carbonyl cycloadduct complex 2, prepared in a one-pot synthesis from 2,5-dimethylpyrrole, is reduced to the corresponding alcohol and oxidatively decomplexed to yield the relatively inaccessible 5-hydroxymethyl-7-azanorbornene 3.

Scheme 2.
Synthesis of a 5-Substituted 7-azanorbornene
(Os (II) = $[Os(NH_3)_5]$ $(OTf)_2$);
DMAc = N,N-dimethylacetamide; OTf = $CF_3SO_3$

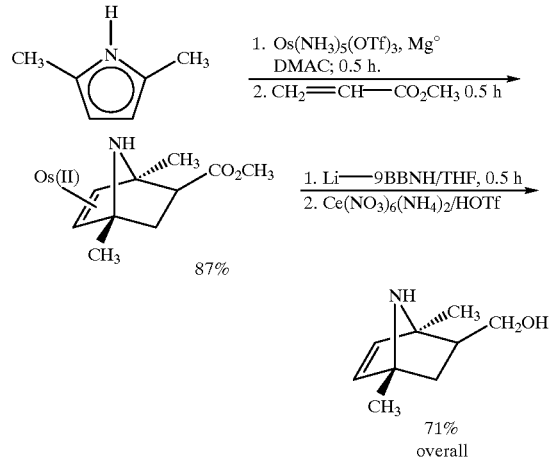

This approach can be used to construct the epibatidine ring system if a 3-vinyl pyridine is used as the dipolarophile.

Scheme 1.
Dipolar cycloaddition of η²-pyrrole complex with dipolarophile.
Os(II) = $[Os(NH_3)5]$ $(OTf)_2$.

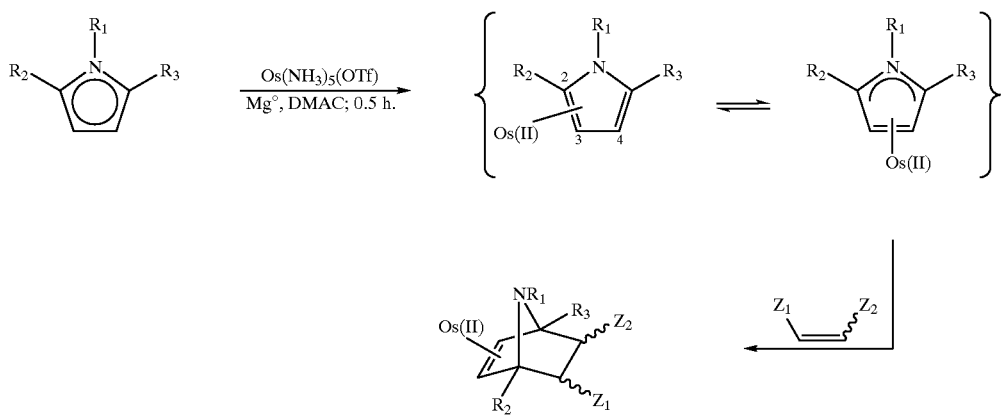

The resulting 7-azabicyclo[2.2.1]-hept-5-ene ligand is unstable with respect to cycloreversion, but metal coordination greatly stabilizes the complex and thus provides the opportunity to carry out functional group transformations The use of methyl-trans-3-(3-pyridyl)-acrylate in the above reaction sequence (using the 2,5-dimethylpyrrole complex shown in Scheme 2), yields compound 4, shown below, which contains the carbon skeleton of the natural product.

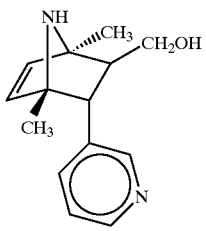

Epibatidine has no substitution at the bridgehead carbons (C[1] and C[4]). The reactivity of simple pentaammineosmium (II)- pyrrole complexes with dipolarophiles decreases in the order 2,5-dimethylpyrrole >N-methylpyrrole>pyrrole. Generally, additional activation of the dipolarophile, by careful selection of the electron withdrawing group attached to the olefin, or high pressure is required to obtain cycloadducts without substitution at the bridgehead positions. Although the parent pyrrole complex gives complex mixtures, the N-methyl pyrrole reacts with the N-methylated and 6-carboxylated pyridyl acrylates to yield cycloadducts 5 and 6 as single diastereomers.

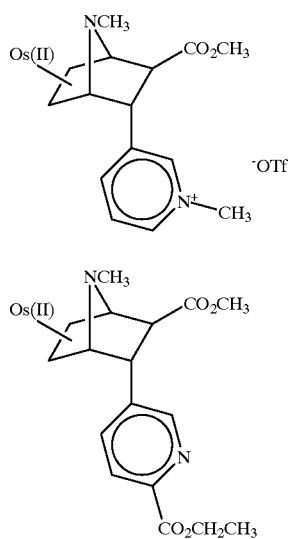

An alternative method for stabilization of the azabicyclo [2.2.1]-heptane nucleus involves protonation of the secondary amine (and pyridyl group) followed by oxidative removal of the metal and in situ hydrogenation of the azanorbornene. An example of this method is shown in Scheme 3 below for the synthesis of the 1,4-dimethyl-exo-carbomethoxy-norchloroepibatidine 7.

Scheme 3.
Decomplexation and hydrogenation to generate a 7-azanorbornane.
($[Os]^{2+} = [Os(NH_3)_5] \ (Otf)_2$)

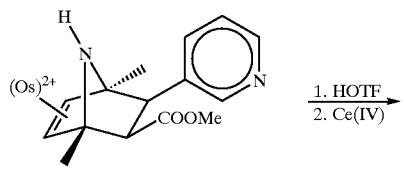

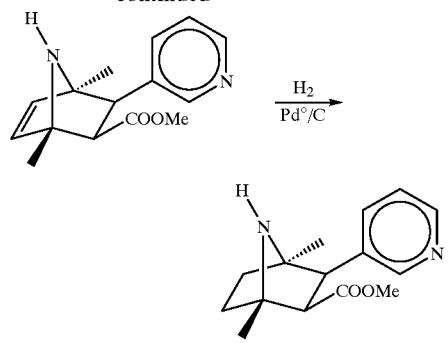

The process for preparing optionally substituted 7-azabicyclo[2.2.1]heptanes and 7-azabicyclo[2.2.1]hept-5-enes via pentaammineosmium(II) complexes proceeds in three steps. In the first step, the optionally substituted pyrrole is treated with pentaammineosmium(II). An excess of the pyrrole complex is usually preferred. Pentaammineosmium(II) is generated in situ by the reduction of pentaammineosmium(III) with a one electron reducing agent that has a reducing potential of less than −0.75 volts versus hydrogen. The counteranion of pentaammineosmium (II) can be any anion that does not adversely affect the overall reaction. Typical counteranions are $CF_3SO_3^-$ (Otf$^-$), $PF_6^-$, $S^-$, and (alkyl or aryl)$SO_3^-$.

Any chemical or electrochemical reducing agent that can reduce the osmium complex from a III valence state to a II valence state and which does not cause or participate in undesired side reactions is suitable. Examples of appropriate reducing agents include magnesium, zinc, aluminum, sodium, cobaltocene and electrochemical reduction. In a preferred embodiment, activated magnesium powder is used.

The optionally substituted pyrrole, pentaammineosmium (III), and reducing agent are stirred at a temperature ranging between 0° C. and 50° C. until the desired organometallic complex is formed, typically between 0.1 and 1.0 hours. The reaction can be carried out in a polar or nonpolar solvent, including but not limited to N,N-dimethylacetamide, N,N-dimethylformamide, water, methanol, acetonitrile, acetone, dimethylsulfoxide, $CH_2Cl_2$, or dimethoxyethane. The reaction is carried out in the absence of $O_2$, and typically under nitrogen, at a pressure of 1 atm or greater.

In the second step of the process, the dipolarophile is added to the stirring solution of the pyrrole pentaammineosmium (II) complex to produce an optionally substituted 7-azabicyclo[2.2.1]-hept-5-ene. Any molar ratio of dipolarophile to pyrrole can be used that provides the desired results. Typically, a molar ratio of dipolarophile to pyrrole ranging between approximately 1 and 10 provides a suitable yield of product. The reaction solution is stirred at a temperature ranging between 10 and 50° C. until the product is formed, typically between 1 and 24 hours.

In an optional step after the bicyclic ring system is formed, and while pentaammineosmium is still complexed to the pi-orbital of the heptene moiety, functional groups on the bicyclic ring can be derivatized using conventional processes. For example, esters can be reduced to alcohols, nitriles to amines, sulfones to sulfides, nitro groups to amines, and amides to amines. Sulfones and carboxylates can be reductively eliminated using the Barton decarboxylation procedure. High temperatures and strong bases should be avoided in the functionalization procedures to avoid ring disruption and unwanted side reactions.

In the third step of the reaction, the pentaammineosmium (II) complex is removed from the optionally substituted 7-azabicyclo[2.2.1]-hept-5-ene by, for example, treatment with cerium (IV) or oxygen in acidic solution. For example, the 7-azabicyclo[2.2.1]-hept-5-ene can be treated with one equivalent of cerium reagent at 20° C. in a polar solvent such as acetonitrile. Appropriate reagents include $Ce(NO_3)_6$ $(NH_4)_2$, DDQ, and other inorganic or organic oxidants with E>+0.70 volts versus hydrogen. Alternatively, the osmium reagent can be removed by heating the complex as necessary, usually between approximately 50° C. and 100° C.

Using the method of synthesis described above, a wide variety of substituted 7-azanorbornanes and 7-azanorbornenes can be prepared. Examples of representative compounds are summarized in Tables 1 and 2.

Some of them are useful as intermediates for the synthesis of desired compounds containing complex heteroaryl or polar substituents as $R_2$ and/or $R_3$.

TABLE 1

|  | $R_1$ | $R_2$ | $R_3$ |
|---|---|---|---|
| 7-azabicyclo[2.2.1]heptane | H | exo-$CH_2OH$ | H |
|  | H | exo-$CH_2OH_3$ | H |
|  | H | exo-$CH_2OH$ | endo-3-py |
|  | H | exo-$CO_2CH_3$ | endo-3-py |
|  | H | exo-$CO_2CH_3$ | exo-3-py |
|  | H | exo-$SO_2Ph$ | endo-3-py |
|  | H | endo-$SO_2Ph$ | exo-3-py |
| 7-azabicyclo[2.2.1]hept-5-ene | H | exo-$CH_2OH$ | H |
|  | CBz | exo-$CH_2OH$ | H |
|  | Cbz | exo-OCBz | H |
|  | H | exo-$CH_2OH$ | endo-3-py |

TABLE 2

| Example | $R_1$ | $R_2$ | $R_3$ |
|---|---|---|---|
| 15 | $CH_3$ | exo-COOMe | H |
| 15 | $CH_3$ | endo-COOMe | H |
| 16 | $CH_3$ | exo-C≡N | H |
| 16 | $CH_3$ | endo-C≡N | H |
| 17 | H | exo-COOMe | endo-COOMe |
| 18 | H | exo- —C(O)—N(Ph)—C(O)— |  |
| 18 | H | endo- —C(O)—N(Ph)—C(O)— |  |
| 19 | Et | exo- —C(O)—N(Ph)—C(O)— |  |
| 20 | H | exo- —C(O)—N(Ph)—C(O)— |  |
| 21 | $CH_3$ | exo-$CH_2NH_2$ | H |
| 22 | $CH_3$ | exo-$CH_2NC_4H_4$ | H |
| 23 | $CH_3$ | exo-$CH_2OH$ | H |

TABLE 2-continued

| Example | $R_1$ | $R_2$ | $R_3$ |
|---|---|---|---|
| 24 | $CH_3$ | exo-$CH_2OOCPh$ | H |
| 25 |  | (3-pyridyl) |  |

Methods for preparing compounds of Formula (I) via derivatization of a 5,6-$\eta^2$-7-aza-bicyclo[2.2.1]hept-5-ene are set out below. These examples are merely illustrative, and are not intended to limit the scope of the invention.

EXAMPLE 1

Preparation of 1,4-Dimethyl-2-exo-(hydroxymethyl)-7-azabicyclo[2.2.1]hept-5-ene (8)

A solution of the 5,6-$\eta^2$ osmium complex of compound 8 (727 mg, 1.0 mmol) in 2 grams acetonitrile was protonated with excess triflic acid (250 mg, 1.67 mmol) and treated at −10° C. with a likewise-cooled solution of ceric ammonium nitrate (560 mg, 1.02 mmol) and triflic acid (560 mg, 3.73 mmol) in 2 grams acetonitrile. Water (1–2 ml) was added to dissolve the precipitated salts, the mixture made basic with 40 ml 10% aqueous sodium carbonate and the product extracted with 5×20 ml methylene chloride. The extract was dried over $MgSO_4$ and the solvent evaporated, yielding 147 mg of brown oil. The crude product was purified by silica gel column chromatography using 1:10 of 15 wt % $NH_3$ in methanol/methylene chloride, yielding 62 mg (41%) of pure 8. (oil, $R_f$=0.5). $^1$H NMR (300 MHz, $CDCl_3$) d 6.31 (d, J=5.3 Hz, 1H), 6.09 (d, J=5.3 Hz, 1H), 3.99 (dd, J=10.3, 2.1 Hz, 1H), 3.67 (dd, J=10.3, 2.1, 1H), 3.6–2.8 (v br, ~2H, OH and NH), 1.4–1.8 (m, 3H), 1.48 (s, 3H), 1.47 (s, 3H); $^{13}$C NMR (75 MHz, $CDCl_3$) d 145.2 (CH), 141.5 (CH), 69.9 (C), 67.0 (C), 61.5 ($CH_2$), 41.7 (CH), 37.0 ($CH_2$), 18.9 ($CH_3$), 15.7 ($CH_3$). This material was further characterized by conversion to the picrate salt. m.p. 186–188° C.; Anal. Calcd. for $C_{15}H_{18}N_4O_8$: C, 47.12; H, 4.75; N, 14.65. Found: C, 46.96; H, 4.52; N, 14.66.

EXAMPLE 2

Preparation of N-CBZ-1,4-Dimethyl-2-exo-(hydroxymethyl)-7-azabicyclo[2.2.1]hept-5-ene (9) and N,O-Bis-CBZ-1,4-Dimethyl-2-exo-(hydroxymethyl)-7-azabicyclo[2.2.1]hept-5-ene (10)

The crude aminoalcohol 8 obtained from 1.0 mmol of the osmium complex as described above was suspended in a solution of aqueous $Na_2CO_3$ (0.38 grams in 2 grams water), and the mixture chilled to 0° C. Benzyl chloroformate (510 mg, 3 mmol) was added, and the mixture allowed to warm to room temperature with vigorous stirring. After 20 hours at 25° C. the mixture was extracted with methylene chloride, and the extracts dried and rotoevaporated, yielding 0.4 grams of brown oil. The crude material was chromatographed twice using 1:8 ethyl acetate/petroleum ether, yielding 43 mg (10%) of 9 and 64 mg (22%) of 10 ($R_f$=0.5 and 0.1, respectively) For 9: $^1$H NMR (300 MHz, $CDCl_3$) d 7.32 (m, 5H, Phenyl), 6.06 (ABq, J=5.7 Hz, 2H, H5 and H6), 5.04

(s, 2H, OCH$_2$Ph), 3.69 (m, 2H, CH$_2$OH), 2.18 (br s, 1H, OH), 1.75 (2Xs, 6H, CH$_3$), 1.7 (m, overlap, 1H), 1.55 (m, 2H); $^{13}$C NMR (75 MHz, CDCl$_3$) d 155.2 (CO), 140.5 (CH, C5 or C$_6$), 140.2 (CH, C6 or C5), 136.4 (C, ipso), 128.3 (CH), 127.9 (CH), 127.8 (CH), 71.1 (C), 69.0 (C), 66.4 (CH$_2$OH), 63.0 (CH$_2$), 45.6 (CH), 37.7 (CH$_2$), 19.4 (CH$_3$), 16.8 (CH$_3$). For 10: $^1$H NMR (300 MHz, CDCl$_3$) d 7.37 (m, 5H, Phenyl), 7.32 (m, 5H, Phenyl), 6.07 (ABq, J=5.5 Hz, 2H, H5 and H6), 5.16 (s, 2H, OCH$_2$Ph), 5.05 (ABq, J=13.5 Hz, 2H, OCH$_2$Ph), 4.33 (dd, J=10.5, 7 Hz, 1H, ½ CH$_2$OCBZ), 4.06 (dd, J=10.5, 7.5 Hz, 1H, ½CH$_2$OCBZ) 1.94 (m, 1H, H2), 1.79 (s, 3H, CH$_3$) 1.75 (s, 3H, CH$_3$), 1.60 (dd, J=11.4, 9 Hz, 1H, H3$_{endo}$), 1.4 (dd, J=11.4, 3.6 Hz, H3$_{exo}$) $^{13}$C NMR (75 MHz, CDCl$_3$) d 155.0 (CO), 154.9 (CO), 140.5 (CH, C5 or C6), 140.5 (CH, C6 or C5), 136.4 (C, ipso), 135.2 (C, ipso), 128.5 (overlap of 2×CH), 128.4 (CH), 128.3 (CH), 128.0 (CH), 127.8 (CH), 70.8 (C), 69.6 (overlap of 2× CH$_2$), 68.9 (C), 66.3 (CH$_2$O), 43.2 (CH, C5), 38.7 (CH$_2$, C6), 19.3 (CH$_3$), 17.0 (CH$_3$).

EXAMPLE 3
Preparation of 1,4-Dimethyl-2-endo-(3'-pyridyl)-3-exo-(hydroxymethyl)-7-azabicyclo[2.2.1]hept-5-ene (11)

The corresponding 5,6-η$^2$ osmium complex was treated as described above for compound 8. Diagnostic $^1$H NMR information: 6.43 (d, J=6H, 1H, H5 or H6), 6.0 (d, J=6 Hz, 1H, H6 or H5), 4.0 (dd, J=10, 2.5 Hz, 1H, ½ CH$_2$OH), 3.75 (dd, J=10, 2.5 Hz, ½ CH$_2$OH), 1.55 (s, CH$_3$), 1.38 (s, CH$_3$).

EXAMPLE 4
Preparation of 1,4-Dimethyl-2-exo-(hydroxymethyl)-7-azabicyclo[2.2.1]heptane (12)

A sample of crude compound 8 (85 mg, 0.56 mmol) was stirred with 30 mg 10% Pd-on-C and 0.5 g methanol in a 5-ml round-bottomed flask under 1 atmosphere of H$_2$ for 30 minutes. The reaction mixture was filtered through celite and evaporated, yielding 78 mg of oil. Purification by preparative thin layer chromatography (0.25 mm, 20×20 cm; Eluent=1:6 15% NH$_3$ in MeOH, CH$_2$Cl$_2$), yielded 14 mg (16%) of pure 12 (R$_f$=0.5) $^1$H NMR (300 MHz, CDCl$_3$) d 3.89 (br, 2H, NH and OH), 3.82 (d J=10.6 Hz, ½ CH$_2$OH), 3.38 (d, J=10.6 Hz, ½ CH$_2$OH), 1.7–1.5 (m, 7H, 3×CH$_2$+ CH), 1.41 (s, 3H, CH$_3$), 1.37 (s, 3H, CH$_3$); $^{13}$C NMR (75 MHz, CDCl$_3$) d 66.8, 64.0, 63.8, 45.5, 40.0, 39.1, 39.07, 20.6, 17.8

EXAMPLE 5
Preparation of 1,4-Dimethyl-2-exo-carboxymethyl-7-azabicyclo[2.2.1]heptane (13)

The corresponding 2,3-η2-osmium complex 18 was protonated and decomplexed with Ce(IV) as described for 8. The acetonitrile was evaporated and the unstable, protonated 7-azanorbornene hydrogenated in methanol as described for 12. Compound 13 was obtained as an oil following an aqueous workup (e.g., see procedure for 8) and preparative thin layer chromatography purification. $^1$H NMR (300 MHz, CDCl$_3$) d 3.60 (s, 3H, CH$_3$O), 2.63 (dd, J=8.1, 5.1 Hz, 1H, H2), 2.49 (br s, 1H, NH), 1.82 (dd, J=12.2, 8.1 Hz, 1H, H3$_{endo}$), 1.75–1.2 (m, overlap, 5H), 1.32 (s, CH$_3$), 1.2 (s, 3H, CH$_3$); $^{13}$C NMR (75 MHz, CDCl$_3$) d 176.5 (CO), 67.7, 63.4, 53.0, 51.3, 44.0, 38.3, 36.7, 20.5, 18.3.

EXAMPLE 6
Preparation of 1,4-Dimethyl-2-endo-(3'-pyridyl)-3-exo-carboxymethyl-7-azabicyclo[2.2.1]heptane (14a) and its exo-pyridyl-endo-carboxyl isomer (14b)

These isomers were obtained as an inseparable 94:6 mixture from the corresponding mixture of osmium complexes following the procedure for 13. For 14a, $^1$H NMR (300 MHz, CDCl$_3$) d 8.45 (m, 2H, H2' and H6' overlap), 7.49 (dt, J=7.8, 1.5 Hz, 1H, H4'), 7.23 (dd, J=7.8, 4.8 Hz, 1H, H5') 3.64 (s, 3H, CH$_3$O), 3.29 (dd, J=5.9, 2.1 Hz, 1H, H2), 2.95 (d, J=5.9 Hz, 1H, H3), 2.62 (br s, 1H, NH), 1.85–1.6 (m, 2H, CH$_2$'s), 1.5 (m, 1H), 1.35 (m, 1H), 1.29 (s, 3H, CH$_3$), 1.26 (s, 3H, CH$_3$); $^{13}$C NMR (75 MHz, CDCl$_3$) d 175.7 (CO), 149.8 (CH), 148.2 (CH), 135.3 (CH), 134.1 (C), 123.1 (CH), 67.6 (2×C overlap), 58.7 (CH), 58.3 (CH), 51.7 (CH$_3$O), 38.6 (CH$_2$), 30.3 (CH$_2$), 19.3 (CH$_3$), 18.7 (CH$_3$). Diagnostic features of 14b: d 3.36 (d, J=6 Hz, H2), 2.8 (dd, J=6, 2 Hz, H3)

EXAMPLE 7
Preparation of 1,4-Dimethyl-2-endo-(3'-pyridyl)-3-exo-(hydroxymethyl)-7-azabicyclo[2.2.1]heptane (15)

Compound 14 was reduced with lithium aluminum hydride in ether, yielding a clear resin after an aqueous workup. Diagnostic $^1$H NMR resonances: 3.87 (dd, J=10.6, 2.8 Hz, 1H, ½ CH$_2$OH), 3.46 (dd, J=10.6, 3.0 Hz, 1H, ½ CH2OH), 3.16 (dd, J=5.0, 1.9 Hz, 1H, H2), 1.5 (s, 3H, CH$_3$), 1.25 (s, 3H, CH$_3$)

EXAMPLE 8
Preparation of 1,4-Dimethyl-2-endo-(3'-pyridyl)-3-exo-phenylsulfonyl-7-azabicyclo[2.2.1]heptane (16a) and its exo-pyridyl, endo-phenylsulfonyl isomer (16b)

The procedure for compounds 13 and 14 was followed yielding a mixture of isomeric 7-azanorbornanes. Diagnostic $^1$H NMR peaks for major isomer: 3.6 (d, J=7 Hz, 1H, CH$_{endo}$), 2.95 (dd, J=7, 1.5 Hz, 1H, CH$_{exo}$), 1.85 (s, 3H, CH$_3$), 1.25 (s, 3H, CH$_3$)

EXAMPLE 9
Preparation of [Os(NH$_3$)$_5$(2,3-η$^2$-2,5-dimethylpyrrole)] (OTf)$_2$ (17)

To a solution of [Os(NH$_3$)$_5$OTf]OTf$_2$ (1.445 grams, 2.00 mmol) in 1.5 grams N,N-dimethylacetamide was added 2,5-dimethylpyrrole (1.5 g, 16 mmol) and activated Mg° (1.0 g, 41 mmol) and the slurry stirred for 45–60 minutes. The slurry was filtered through a medium-porosity frit into 150 ml CH$_2$Cl$_2$, giving a light yellow precipitate, which was filtered, washed with CH$_2$Cl$_2$ and ether, then dried. The yield of a light-yellow powder was 1.23–1.31 g (92–98%).

EXAMPLE 10
Preparation of 5,6-exo-η$^2$-Os(NH$_3$)$_5$-1,4-dimethyl-2-exo-carbomethoxy-7-azabicyclo-[2.2.1]hept-5-ene) (OTf)$_2$ (18)

The 2,5-dimethylpyrrole complex (669 mg, 1.0 mmol) was suspended in 2 grams methyl acrylate and the slurry stirred for 1 hour. Acetonitrile (c. 1 ml) was added to dissolve the solids and the resulting solution added dropwise to 50 ml of ether while stirring. The precipitate was filtered, washed with ether and dried, yielding 730 mg (97%) of an off-white powder. $^1$H NMR (300 MHz, CD$_3$CN) d 3.97 (br s, 3H, trans-NH$_3$), 3.65 (s, 3H, CH$_3$O), 3.34 (br s, 12H, cis-NH$_3$), 3.17 (d, J=6.3 Hz, 2H, H5 or H6), 3.13 (d, J=6.3 Hz, 1H, H6 or H5), 2.77 (dd, J=8.1, 4.2 Hz, 1H, H2), 2.14 (br s, 1H, NH), 2.05 (dd, J=11.6, 8.1 Hz, 1H, H3$_{endo}$), 1.63 (dd J=11.6, 4.2 Hz, H3$_{exo}$), 1.39 (s, 3H, CH$_3$), 1.24 (s, 3H, CH$_3$); $^{13}$C NMR (75 MHz, CD$_3$CN) d 176.4 (CO), 75.7 (C), 71.0 (C), 59.1 (CH), 58.0 (CH), 55.3 (CH), 51.6 (OCH$_3$), 47.1 (CH$_2$), 18.3 (CH$_3$), 15.9 (CH$_3$); Anal. Calcd. for C$_{12}$H$_{30}$N$_6$O$_8$S$_2$F$_6$Os: C, 19.10; H, 4.01; N, 11.14. Found: C, 18.57; H, 3.96; N, 11.02.

EXAMPLE 11
Preparation of Pentaammineosmium-Pyrrole Complexes: 2,3-$\eta^2$-[Os(NH$_3$)$_5$]-Ligand](OTf)$_2$, where Ligand is pyrrole or N-methyl pyrrole A mixture of [Os(NH$_3$)$_5$OTf](OTf$_2$) (723 mg, 1.0 mmol), N,N-dimethylacetamide (1 g), DME (3 g), pyrrole or N-methyl pyrrole (1 g) and magnesium (0.5 g) was stirred for 1 hour. The solution was filtered through a 60-ml medium fritted glass funnel with the aid of 10–15 ml of DME, and the filtrate added dropwise to methylene chloride (150 ml). The resulting precipitate was filtered, and washed with portions of methylene chloride (20 ml) and ether (2×20 ml), and dried under nitrogen. The yield of this reaction is typically 90–95% of a yellow-orange solid containing approximately 8% of a binuclear impurity.

EXAMPLE 12
Preparation of Pentaammineosmium-Cycloadduct Complexes

The pentaammineosmium-pyrrole complex obtained from Example 11 was treated with an excess (3–30 eq) of a dipolarophile in either acetonitrile or N,N-dimethylacetamide solution. After 1–10 hours, the solution was added to ether or methylene chloride with stirring (20 ml of ether per gram of acetonitrile or 75 ml methylene chloride per gram of N,N-dimethylacetamide). The resulting precipitate was worked up as described in Example 11 providing a yield of 85–95%.

EXAMPLE 13
One-Pot Process for the Synthesis of Pentaammineosmium-Cycloadduct Complexes A dipolarophile (e.g., methyl acrylate) was added directly to the reaction mixture in the synthesis of the parent pyrrole complex as described in Example 11. After a suitable reaction time (e.g., 1–10 hours), the mixture was filtered to remove the magnesium, and the filtrate was added to 1:1 methylene-chloride/ether (100 ml for every gram of N,N dimethylacetamide used in the synthesis) with stirring. The solid was isolated as described in Example 11 yielding the cycloadduct complex as mono-N,N-dimethylacetamide solvate in ~95% yield.

EXAMPLE 14
One-Pot Process for the Synthesis of 7-Azanorbornanes from the Pentaammineosmium-Cycloadduct Complex The cycloadduct complex (1.0 mmol) prepared in Example 13 was dissolved in acetonitrile (4 g), protonated with triflic acid (3–5 eq), and treated with DDQ (1 eq). The dark solution was transferred to a 50-ml round-bottomed flask with the aid of an additional 20 ml of acetonitrile, treated with 10% palladium-on-carbon (approximately 0.5 g, 40 mole %), and hydrogenated under 1 atm H$_2$ (balloon) for a suitable period of time (2–20 hours) (The pyrrole-derived complexes, lacking a substituent on nitrogen, underwent reductive amination to N-ethyl derivatives in acetonitrile. In these cases the solvent was evaporated and the reduction carried out in methanol). Workup A: The reaction mixture was filtered through celite to remove the Pd/C, the cake washed with acetonitrile (or methanol), and the filtrate evaporated. The residue was dissolved in water (approximately 10–15 ml), transferred to a separatory funnel, rendered basic with 10% aqueous Na$_2$CO$_3$ (20 ml) and extracted with methylene chloride (3×40 ml). The extract was dried over MgSO$_4$ and evaporated, yielding the crude 7-azanorbornanes. Workup B: The hydrogenation reaction mixture was treated with 1 ml NH$_4$OH, diluted with an equal volume of methylene chloride (about 30 ml), then filtered directly through 20 cc of silica gel in a 30-ml medium fritted glass funnel. The flask and silica were washed with an additional 2×30 ml of 1:1 methylene chloride/acetonitrile (or methanol) containing ~3–5% NH$_4$OH, and the combined eluent evaporated, yielding the crude 7-azanorbornanes.

EXAMPLE 15
Preparation of 2-Carbomethoxy-7-methyl-7-azabicyclo[2.2.1]heptanes These compounds, obtained as a 1:1 mixture of isomers, were prepared in 66% overall yield from N-methyl pyrrole and methyl acrylate using the method set forth in Examples 13 and 14 (workup B). The isomers were separated by preparative thin layer chromatography using 1:1:5 HMDS/Methanol/methylene chloride: Exo isomer (1): $R_f$=0.76; $^1$H NMR (CDCl$_3$) δ 3.66 (s, 3H, CH$_3$O), 3.62 (d, J=4.2 Hz, 1H, H4), 3.30 (t, J=4.0 Hz, 1H, H4), 2.40 (dd, J=9.6, 5.4 Hz, 1H, H2), 2.21 (s, 3H, CH$_3$N), 2.18 (m, 1H), 1.86 (m, 2H), 1.57 (dd, J=12.6, 9.6 Hz, 1H, H3$_{endo}$), 1.33 (m, 2H); $^{13}$C NMR (CDCl$_3$) δ 174.6 (C, CO), 64.2 (CH, C1 or C4), 61.1 (CH, C4 or C1), 51.9 (CH$_3$, CH$_3$O), 47.4 (CH, C2), 34.5 (CH$_3$, CH$_3$N), 33.3 (CH$_2$), 26.7 (CH$_2$), 26.2 (CH$_2$); Endo isomer (2): $R_f$=0.62; $^1$H NMR (CDCl$_3$) δ 3.65 (s, 3H, CH$_3$O), 3.44 (t, J=4.5 Hz, 1H, H1 or H4), 3.21 (t, J=4.5 Hz, 1H, H4 or H1), 3.08 (m, 1H, H2), 2.26 (s, 3H, CH$_3$N), 1.95 (m, 1H), 1.75 (m, overlap, 3H), 1.36 (m, 2H); $^{13}$C NMR (CDCl$_3$, 50° C.) δ 174.3 (C, CO), 64.1 (CH, C1 or C4), 62.1 (CH, C4 or C1), 51.4 (CH$_3$, CH$_3$O), 45.2 (CH, C2), 34.4 (CH$_3$, CH$_3$N), 30.6 (CH$_2$), 28.0 (CH$_2$), 24.2 (CH$_2$). The picrate salt (both isomers combined) was crystallized from wet ethanol (m.p. 102–108° C.); Anal. Calcd. for C$_{15}$H$_{18}$N$_4$O$_9$; C, 45.23; H, 4.55; N, 14.07. Found: C, 45.42; H, 4.59; N, 14.10.

EXAMPLE 16
Preparation of 2-Cyano-7-methyl-7-azabicyclo[2.2.1] heptanes

These compounds, obtained as a 1:1 mixture of isomers, were prepared in 57% overall yield from N-methyl pyrrole and acrylonitrile using the method set forth in Examples 13 and 14 (workup B). The isomers were separated by preparative thin layer chromatography, using 1:1:8 HMDS/methanol/methylene chloride. Exo isomer (3): $R_f$=0.71; $^1$H NMR (CDCl$_3$) δ 3.53 (d, J=3.3 Hz, 1H, H1), 3.37 (t, J=3.8 Hz, 1H, H4), 2.44 (dd, J=9.3, 5.1 Hz, 1H, H2), 2.36 (s, 3H, CH$_3$N), 2.1 (m, 1H), 1.83 (m, 2H), 1.75 (dd, J=12.6, 9.3 Hz, 1H, H3$_{endo}$), 1.3 (m, 2H); $^{13}$C NMR (CDCl$_3$) δ 122.7 (C, CN), 65.5 (CH, C1 or C4), 60.8 (CH, C4 or C1), 35.7 (CH$_2$), 35.3 (CH$_3$), 31.9 (CH), 27.5 (CH$_2$), 26.9 (CH$_2$); Endo isomer (4): $R_f$=0.55; $^1$H NMR (CDCl$_3$) δ 3.44 (t, J=4.5 Hz, 1H, H1 or H4), 3.29 (t, J=4.5 Hz, 1H, H4 or H1), 2.92 (dtd [11 line pattern], J=12, ~4.8, 1.8 Hz, 1H, H2), 2.26 (s, m overlap, 4H, CH$_3$N and H3$_{exo}$), 2.0–1.8 (m, 3H), 1.57 (dd, J=12.3, 5.1 Hz, 1H, H3$_{endo}$), 1.45 (m, 1H); $^{13}$C NMR (CDCl$_3$, 50° C.) δ 121.7 (C, CN), 63.8 (CH, C1 or C4), 61.6 (CH, C4 or C1), 34.6 (CH$_2$), 34.4 (CH$_3$, CH$_3$N), 29.2 (CH, C2), 27.9 (CH$_2$), 24.1 (CH$_2$). The picrate salt (both isomers combined) was crystallized from ethanol (mp 218–224° C.): Anal. Calcd. for C$_{14}$H$_{15}$N$_5$O$_7$: C, 46.03; H, 4.14; N, 19.17. Found: C, 45.85; H, 4.08; N, 18.88.

EXAMPLE 17
Preparation of trans-2,3-Bis-carbomethoxy-7-azabicyclo[2.2.1]heptane This compound was prepared in 42% overall yield from pyrrole and dimethyl fumarate using the procedures set forth in Examples 11, 12 (using acetonitrile as a solvent), and 14 (hydrogenation solvent—methanol; reaction time—2 h;

workup A). $^1$H NMR (CDCl$_3$) δ 3.95 (t, J=4.5 Hz, 1H, H4), 3.84 (d, J=4.8 Hz, 1H, H1), 3.70 (s, 3H, CH$_3$O), 3.695 (s, 3H, CH$_3$O), 3.22 (td, J=4.8, 1.8 Hz, 1H, H3), 3.03 (d, J=4.8 Hz, 1H, H2), 2.55 (br s, 1H, NH), 0.8–1.3 (overlapping m, 4H); $^{13}$C NMR (CDCl$_3$) δ 174.8 (C, CO), 172.1 (C, CO), 61.8 (CH, C1 or C4), 59.1 (CH, C4 or C1), 52.3 (CH), 52.1 (CH$_3$, CH$_3$O), 52.0 (CH$_3$, CH$_3$O), 50.1 (CH), 28.7 (CH$_2$), 24.9 (CH$_2$).

EXAMPLE 18
Preparation of Hexahydro-2-phenyl-4, 7-imino-1H-isoindole-1,3(2H)-dione This compound was obtained as a 4:1 mixture of exo and endo isomers, respectively, in 39% overall yield from pyrrole and N-phenylmaleimide using the procedures set forth in Examples 11, 12 (using acetonitrile as a solvent), and 14 (hydrogenation solvent—methanol; reaction time—2 hours; workup A). The crude material was chromatographed on a preparative thin layer chromatography plate (20×20 cm, 2 mm) using a gradient elution of ether containing ~4% conc. NH$_4$OH and 5, 10 and 20% methanol. Two bands were extracted with ether-methanol: F1 (R$_f$=0.75, ether containing 3% NH$_4$OH and 10% methanol). This material was recrystallized from ethyl acetate-petroleum ether, yielding colorless crystals (mp 206–209° C.); exo isomer. $^1$H NMR (CDCl$_3$) δ 7.5–7.3 (m, 5H, Ph), 4.15 (t, J 2 Hz, 2H, H1, H4), 2.86 (s, 2H, H2, H3), 1.7 (m, 4H, 2×CH$_2$), 1.54 (br s, 1H, NH); $^{13}$C NMR (CDCl$_3$) δ 177.3 (CO), 132.1 (C), 129.0 (CH), 128.5 (CH), 126.5 (CH), 59.9 (CH, C1, C4), 49.0 (CH, C2, C3), 29.5 (CH$_2$). The second fraction (R$_f$=0.21) yielded the endo isomer: $^1$H NMR δ 7.6–7.2 (m, 5H, Ph), 4.18 (br s, 2H, H1 and H4), 3.64 (br s, 1H, NH), 3.41 (br s, 2H, H2 and H3), 1.8–1.6 (m, 4H); $^{13}$C NMR δ 175.9 (C), 132.0 (C), 129.7 (CH), 129.3 (CH), 126.9 (CH), 59.6 (CH), 51.5 (CH), 26.5 (CH$_2$).

EXAMPLE 19
Preparation of 8-Ethylhexahydro-2-phenyl-exo-4,7-imino-1H-isoindole-1,3(2H)-dione This compound was formed when the synthesis of hexahydro-2-phenyl-4,7-imino-1H-isoindole-1,3(2H-dione was carried out using acetonitrile in the hydrogenation step of the method set forth in Example 14 (reaction time—18 h, workup A). The crude material was chromatographed on silica gel (3.5×13 cm column). Elution with ether yielded 56 mg (21%) of the title product (R$_f$=0.8; ether containing NH$_4$OH). Further elution with ether containing 10% methanol and 3% conc. NH$_4$OH yielded a second fraction containing 69 mg of crude hexahydro-2-phenyl-4,7-imino-1H-isoindole-1,3(2H)-dione (R$_f$=0.2; ether containing NH$_4$OH). The first fraction was treated with decolorizing charcoal, filtered, evaporated, and the residue recrystallized from ethyl acetate/petroleum ether. Yield=21 mg of lustrous colorless crystals mp 126–128° C. $^1$H NMR (CDCl$_3$) δ 7.5–7.25 (m, 5H, Ph), 3.82 (t, J=2.2 Hz, 2H, H1, H4), 2.80 (s, 2H, H2, H3), 2.37 (q, J=7.2 Hz, 2H, NCH$_2$), 1.93 (m, 2H, H5$_{exo}$, H6$_{exo}$), 1.51 (m, 2H, H5$_{endo}$, H6$_{endo}$), 1.04 (t, J=7.2 Hz, 3H, CH$_3$); $^{13}$C NMR (CDCl$_3$) δ 177.8 (CO), 132.4 (C, C1'), 129.1 (CH), 128.5 (CH), 126.7 (CH), 62.6 (CH, C1, C4), 49.5 (CH, C2, C3), 40.4 (CH$_2$N), 25.0 (CH$_2$), 14.5 (CH$_3$).

EXAMPLE 20
Preparation of Hexahydro-1-hydroxy-2-phenyl-4,7-imino-1H-isoindole-3(2H)-one The exo imide formed in Example 18 (25 mg. ~0.1 mmol) was treated with excess sodium borohydride (40 mg, ~1.0 mmol) in 5 ml ethanol and the mixture refluxed for 20 minutes. The ethanol was evaporated, the residue acidified with 1 M HCl, and treated with Na$_2$CO$_3$ and methylene chloride. Evaporation of the extract yielded 20 mg of crude material. Preparative thin layer chromatography (gradient elution; ether containing 5% NH$_4$OH and 10–20% methanol) yielded the product (R$_f$=0.25, ether with 3% NH$_4$OH and 10% methanol), still contaminated with a minor product. $^1$H NMR (CDCl$_3$) δ 7.55–7.2 (m, 5H, Ph), 5.22 (s, 1H, NCH(OH)), 3.82 (d, J=2 Hz, 1H), 2.60 (d, J=2H, 1H), 2.71 (d, J=10 Hz, 1H), 2.08 (d, J=10 Hz, 1H), 1.63–1.3 (m, overlap, 6H, 2×CH$_2$, NH, OH).

EXAMPLE 21
Preparation of exo-2-aminomethyl-7-methyl-7-azabicyclo[2.2.1]heptane The nitrile formed in Example 16 (55 mg, 0.4 mmol) was treated with excess lithium aluminum hydride (30 mg, 0.79 mmol) in 10 ml ether with stirring. After 5 minutes (a white suspension formed), the reaction was quenched with methanol (0.1 g), then water (0.1 g), acidified with 1 M HCl, then basified with conc., NH$_4$OH, and extracted with methylene chloride. Drying and evaporation of the extract yielded the corresponding primary amine as an oil (17 mg, 30%). $^1$H NMR (CDCl$_3$) δ 3.18 (t, J=3.9 Hz, 1H, H4), 3.03 (d, J=3.9 Hz, 1H, H1), 2.70 (dd, J=12, 7.8 Hz, 1H, ½ CH$_2$N), 2.51 (dd, J=12, 6 Hz, 1H, ½ CH$_2$N), 2.22 (s, 3H, CH$_3$N), 1.86 (m, 2H), 1.6–1.2 (m, 7H, CH$_2$+NH$_2$ overlap).

EXAMPLE 22
Preparation of exo-2-(1-Pyrrolylmethyl)-7-methyl-7-azabicyclo[2.2.1]heptane The primary amine formed in Example 21 (17 mg, 0.121 mmol) was treated with 2,5-dimethoxytetrahydrofuran (25 mg, 0.189 mmol) in acetic acid (0.1 g) at 150° C. for 5 minutes in an oil bath. Extraction of the basified (10% aqueous Na$_2$CO$_3$) reaction mixture with methylene chloride yielded a mixture of products from which was obtained 8 mg (~30%) of crude exo-2-(1-pyrrolylmethyl) product by preparative thin layer chromatography using 1:1:8 hexamethyldisilazane/methanol/methylene chloride. $^1$H NMR (CDCl$_3$) δ 6.68 (s, 2H), 6.18 (s, 2H), 3.92 (dd, J=15, 12 Hz, 1H, ½CH$_2$N), 3.72 (dd, J=15, 7 Hz, 1H, ½CH$_2$N), 3.22 (m, 1H), 2.96 (m, 1H), 2.26 (s, 3H, CH$_3$N), 1.98 (m, 1H), 1.83 (m, 2H), 1.5–1.22 (m, 4H).

EXAMPLE 23
Preparation of exo-2-Hydroxymethyl-7-methyl-7-azabicyclo[2.2.1]heptane The aminoester formed in Example 15 (41 mg, 0.243 mmol) was treated with lithium aluminum hydride (10 mg, 0.264 mmol) in 5 ml ether. After 5 minutes, the reaction mixture was quenched with methanol, acidified with 1 M HCl, basified with conc. NH$_4$OH, and extracted with methylene chloride. Evaporation of the extract yielded the desired product (11 mg, 32%). $^1$H NMR (CDCl$_3$) δ 3.80 (dd, J=9, 1 Hz, 1H, ½ CH$_2$O), 3.39 (dd, J=9, 2 Hz, 1H, ½ CH$_2$O), 3.21 (t, J=5 Hz, 1H, H4), 3.19 (d, J=4 Hz, 1H, H1), 2.18 (s, 3H, CH$_3$N), 1.82 (m, 3H), 1.7 (m, 1H), 1.5–1.2 (m, 4H).

EXAMPLE 24
Preparation of exo-2-benzoyloxymethyl-7-methyl-7-azabicyclo[2.2.1]heptane The alcohol formed in Example 23 (11 mg, 0.078 mmol) was treated with benzoic anhydride (34 mg, 0.15 mmol) and DMAP (10 mg) in methylene chloride. The product was purified by preparative thin layer chromatography (20×20 cm×0.25 mm) using 1:3:80 NH$_4$OH/methanol/ether (R$_f$= 0.6). Yield: 10 mg (52%). $^1$H NMR (CDCl$_3$) δ 8.05 (d, J=7.2 Hz, 2H, ortho-H), 7.55 (t, J=7.2 Hz, 1H, para-H), 7.44 (t, J=7.2 Hz, 2H, meta-H), 4.18 (m, 2H, CH2O), 3.22 (t, J=3.9 Hz, 1H, H4), 3.18 (d, J=3.6 Hz, 1H, H1), 2.25 (s, 3H, CH$_3$N), 2.05–1.85 (m, overlap, 3H), 1.48 (dd, J=12, 9 Hz, 1H, H3$_{endo}$), 1.34 (m, 3H).

EXAMPLE 25

Preparative of Norbornane Analog of Epibatidine using Reductive Heck Methodology: exo-2-(3-pyridyl) bicyclo [2.2.1]heptane This procedure is based on that described by R. Larock et al. (*J. Chem. Soc. Chem. Comm.* 1989, 1368). A mixture of norbornene (101 mg, 1.07 mmol), 3-iodopyridine (205 mg, 1.0 mmol), tetra-n-butylammonium chloride (287 mg, 1.03 mmol), potassium formate (255 mg, 3.03 mmol), and palladium acetate (28 mg, 0.125 mmol) was stirred in DMF (1.2 g) at room temperature for 72 hours. The mixture was diluted with 10 ml of 10% Na$_2$CO$_3$ (aq) and 10 ml of ether and the aqueous phase extracted again with ether. The combined extracts were dried over MgSO$_4$, filtered and evaporated, and the residue purified by preparative thin layer chromatography (20×20 cm, 2.0 mm, 1:1 petroleum ether/ethyl acetate, Rf=0.5), yielding the title product as an oil (73 mg, 42%). $^1$H NMR (CDCl$_3$) δ 8.42 (s, 1H, H2'), 8.33 (d, J=4.5 Hz, 1H, H6'), 7.43 (d, J=7.8 Hz, 1H, H4'), 7.11 (dd, J=7.8, 4.5 Hz, 1H, H5'), 2.67 (dd, J=8.7, 5.7 Hz, 1H, H2), 2.30 (m, 2H, 1H, H1 and H4), 1.8–1.2 (m, overlap, 8H, 4×CH$_2$, $^{13}$C NMR (CDCl$_3$) δ 149.1 (CH), 146.3 (CH), 142.3 (C), 134.0 (CH), 122.9 (CH), 44.7 (CH), 42.5 (CH), 38.7 (CH$_2$), 36.7 (CH), 35.9 (CH$_2$), 30.3 (CH$_2$), 28.6 (CH$_2$).

Figure 2A:
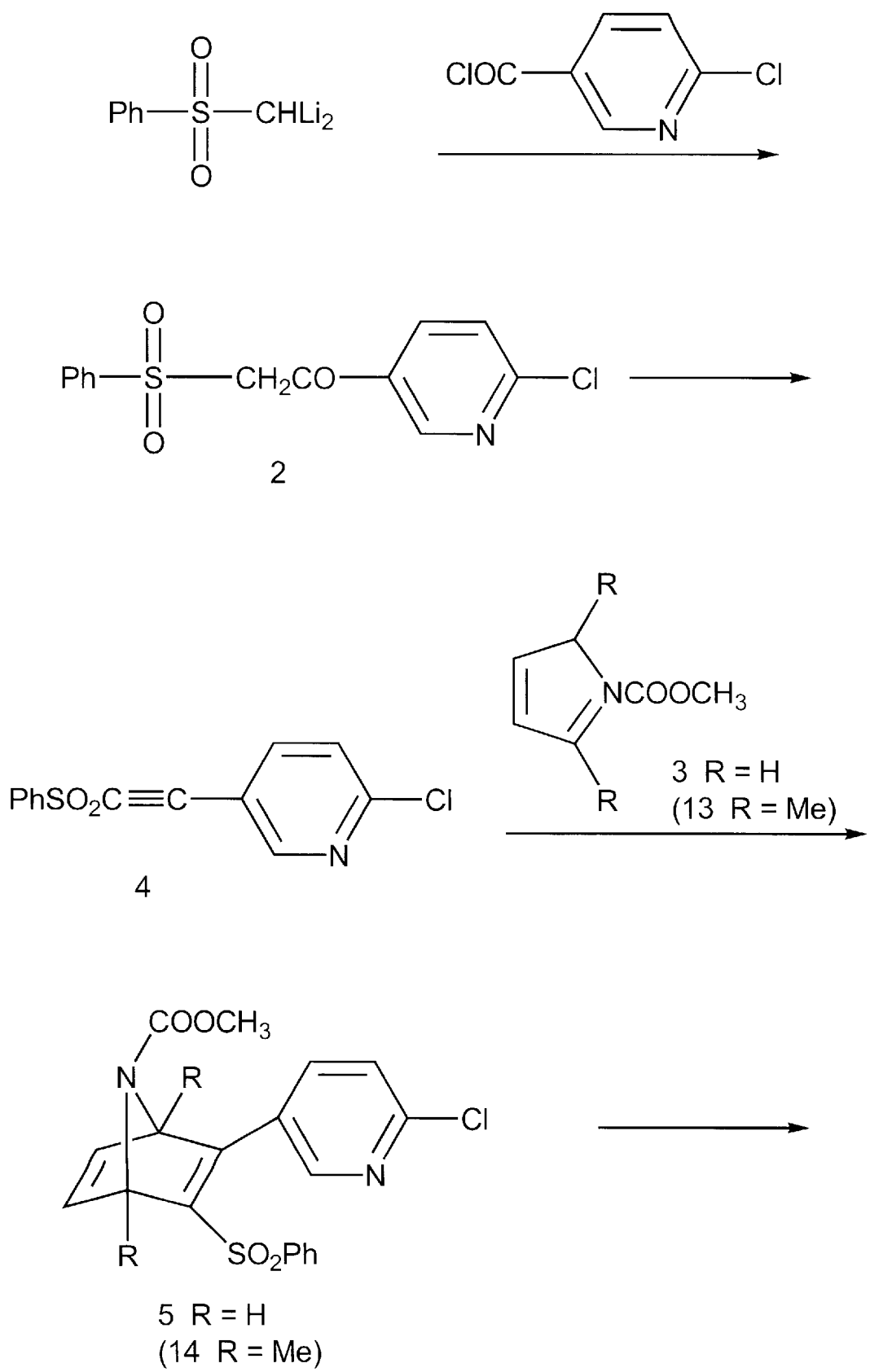
FIGS. 2a and 2b are schematic illustrations of processes for the preparation of active compounds through the Diels-Alder reaction of an N-(electron withdrawing substituted) pyrrole with an arylsulfonyl (optionally substituted aryl or heterocyclic) acetylene.
Figure 2A:
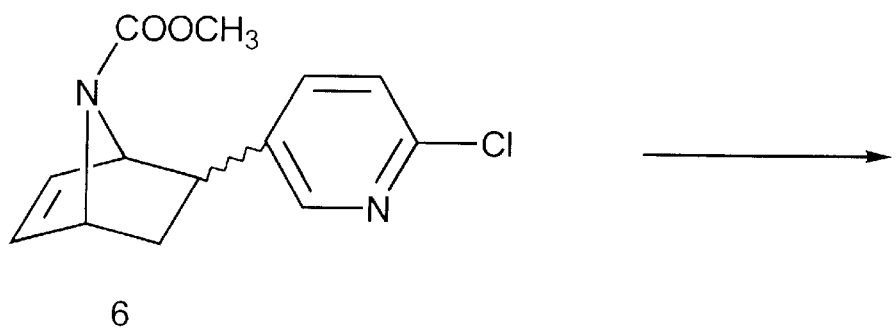
Figure 2A:
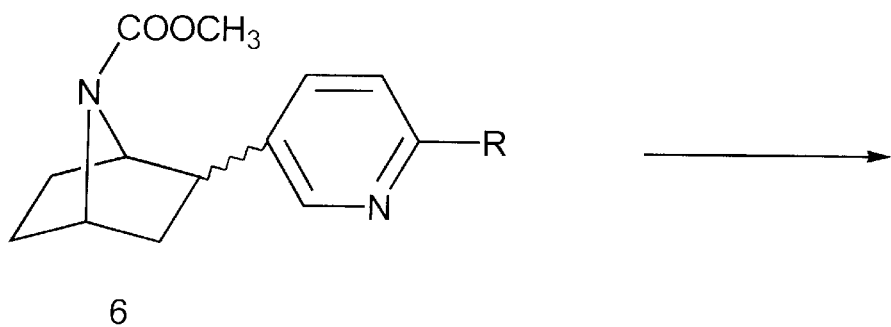
Figure 2A:
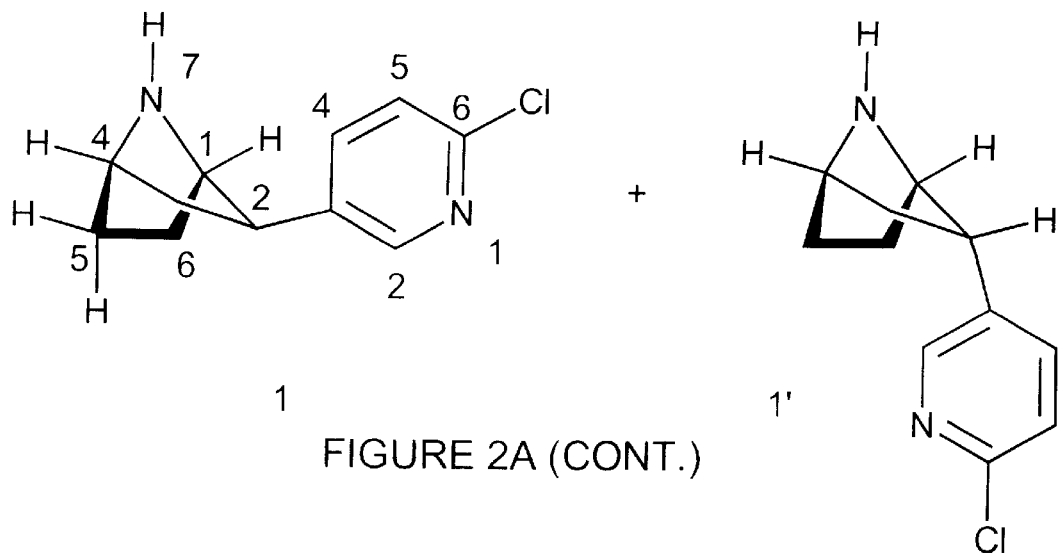
Figure 2B:
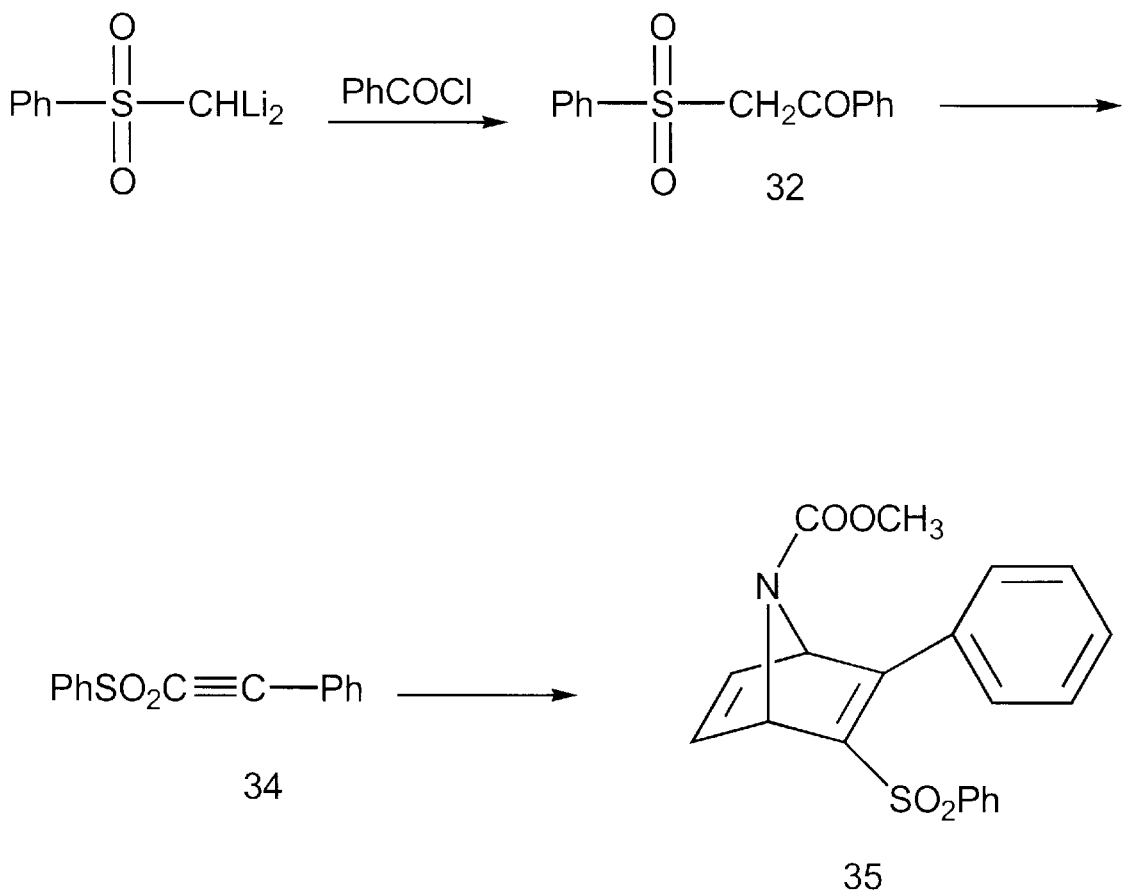

B. Synthesis of the 7-azabicyclo[2.2.1]-heptane or -heptene ring system using Diels-Alder approach In an alternative embodiment, as illustrated in FIGS. 2a and 2b, active compounds, or their precursors, are prepared through the Diels-Alder reaction of an N-(electron withdrawing-substituted)pyrrole with an arylsulfonyl (optionally substituted aryl or heterocyclic)acetylene. The electron withdrawing group at the N$^7$-position decreases the aromaticity of the pyrrole ring and activates the ring in favor of the cycloaddition reaction.

The product of the reaction between the N-(electron withdrawing-substituted)pyrrole with the arylsulfonyl (optionally substituted aryl or heterocyclic)acetylene is a 7-(electron withdrawing substituted)-2-(optionally substituted aryl or heteroaromatic)-3-arylsulfonyl-7-azabicyclo [2.2.1]-hepta-2,5-diene (compounds 23 and 32, FIG. 2). This diene can be derivatized using conventional methods to a wide variety of 7-azabicyclo[2.2.1]-heptanes and -heptenes. For example, an R$^3$ alkyl or aralkyl group can be added by reacting the saturated bicycloheptane derivative of compound 23 or 32 with n-butyl lithium and R$^3$I, followed by treatment with a reducing agent to remove the 3-arylsulfonyl moiety. (Julia, M. and Paris, J-M., *Tetrahedron Letters*, 49, 4833 (1973).) R$^5$ and R$^6$ groups can be added to compound 24 (FIG. 2) by appropriate and conventional reactions of the double bond. (See *Advanced Organic Chemistry* F. A. Carey and R. J. Sundberg (1990) pp. 167–218 Plenum Publishing Co.) Nonlimiting examples of addition reactions include hydrogenation, hydroboration, hydrohalogenation, hydroxylation, halohydrination, alkylation, carbene and dihalo carbene addition and epoxidation followed by ring opening reactions with nucleophiles such as alkoxide, amines, alkylsulfide, halide, and hydroxide.

The reactive chloro in compounds 24 and 25 (FIG. 2) is easily displaced by nucleophiles such as alkoxy, including methoxy, alkylthio, hydroxy, amino, cyano, azide, bromide, iodide, and dimethylamino.

The reaction between the N-(electron withdrawing-substituted)pyrrole with the arylsulfonyl(optionally substituted aryl or heterocyclic)acetylene is carried out in excess N-(electron withdrawing substituted)-pyrrole or in a solvent, for example, toluene, tetrahydrofuran, dimethylformamide, diethoxyethane or other inert solvents. Any molar ratio of pyrrole to dienophile can be used that provides an acceptable yield of product, and typically ranges between 0.5:1 to 50:1, preferable (1–5):1.

The reaction is conducted at any temperature that produces the desired product, and typically, between room temperature and 150° C., until the reaction is completed, for typically between 1 hour and 72 hours at 1 atm. or elevated pressure in a sealed reactor.

Several methods have been investigated for the removal of the N-electron withdrawing group, and specifically, the N-carbomethoxy protecting group, after synthesis of the desired 7-azabicyclo[2.2.1]-heptane or -heptene framework. Hydrolysis of compound 25 (FIG. 2) with potassium hydroxide in methanol results in substitution of the moderately reactive chlorine in the pyridine ring by a methoxy group. Treatment of 25 with methyllithium stopped at the formation of N-acetyl epibatidine (identical with an authentic sample from acetylation of rac-epibatidine as described below), which resisted further cleavage by methyllithium even after a prolonged treatment. This is in accordance with the known stability of N-acetyl epibatidine. Compound 25 is successfully deblocked by treatment with hydrobromic acid in acetic acid for 24 hours at room temperature. The products isolated from silica gel chromatography, with a mixed solvent system of ethyl acetate, methylene chloride and ammonia in methanol as the eluent, were rac-epibatidine (19, 25%), rac-endo-epibatidine (19', 28.4%) and unchanged carbamate (25, 20%). Notably, the recovered starting material is essentially the pure endo isomer of 25, indicating some stereoselectivity in the cleavage of the N-carbomethoxy group with hydrobromic acid. The exo-isomer was apparently cleaved at a higher rate than the endo-isomer, presumably influenced by the proximity of the pyridyl group and the carbamate group. The rac-epibatidine thus obtained, m.p. 50–51°, is very pure, as evidenced by its spectral data.

i) N-(electron withdrawing-substituted)pyrrole

Many substituted pyrroles are known and are easily converted to N-(electron withdrawing-substituted)-pyrroles for use in the Diels-Alder process to prepare 7-azabicyclo [2.2.1]heptanes and -heptenes. For example, 3-(thioalkyl) pyrrole, including 3-(SCH$_3$)pyrrole; 2,5-dialkylpyrrole, including 2,5-dimethylpyrrole; 3,4-dihaloalkylpyrrole, including 3,4-bis(trifluoromethyl)pyrrole, 2-alkylpyrrole, including 2-methylpyrrole; 2-alkoxyalkylpyrrole, including 2-methoxymethylpyrrole; 2-alkylthioalkylpyrrole, including 2-methylthiomethylpyrrole; 2-dialkylaminoalkylpyrrole, including 2-dimethylaminomethylpyrrole; alkyl pyrrole 2-acetate, including dimethylaminomethylpyrrole; alkyl pyrrole 2-acetate, including methyl pyrrole 2-acetate; 2-alkoxyalkoxyalkylpyrrole, including 2-methoxymethoxyethylpyrrole; 3-aryloxyalkylpyrrole, including 3-benzyloxymethylpyrrole; 2-alkoxypyrrole, including 2-methoxypyrrole; 3-alkoxypyrrole, including 3-methoxypyrrole; 3-aryloxypyrrole, including 3-benzyloxypyrrole; 3,4-dialkylpyrrole, and 3-alkylpyrrole, including 3-methylpyrrole and 3,4-dimethylpyrrole; 1,6 and 4,5-alkylidene pyrrole, including 4,5,6,7-tetrahydroindole and 2- methyl-4,5,6,7-tetrahydroindole.

The N-substituent on the pyrrole ring is any moiety that is electron withdrawing and that activates the ring toward cycloaddition with a dienophile. The N-substituent is preferably carbomethoxy, however, other electron withdrawing moieties, including carbobenzyloxy, tert-butoxycarbonyl and optically active alkoxycarbonyl, including (+) and (−)-menthyloxycarbonyl can also be used.

ii). Arylsulfonyl(optionally substituted aryl or heteroaromatic)acetylene

In this process, a compound of the formula aryl-$SO_2C \equiv C$—(optionally substituted aryl or heteroaromatic) is reacted with the N-(electron withdrawing-substituted) pyrrole or its derivative.

The arylsulfonyl-(optionally substituted aryl or heteroaromatic)-acetylene can be prepared by methods known to those of skill in the art. In one embodiment, described in detail in the Example 26 below, the compound is prepared by reacting the lithium salt of methyl(aryl) sulfone with the desired optionally substituted aryl or heteroaromatic acid chloride to produce a 1-(aryl or heteroaromatic)-2-arylsulfonylethanone, that is converted to the corresponding acetylene via an enolphosphate intermediate as described in Example 27 below. Any optionally substituted aryl or heteroaromatic acid chloride can be used, including without limitation, the acid chloride of nicotinic acid, isonicotinic acid, 5-chloronicotinic acid, 6-methylnicotinic acid, 6-methoxynicotinic acid, 6-phenylnicotinic acid, 6-methylthionicotinic acid, 2-chloropyridine-4-carboxylic acid, 2,6-dimethylpyridine-4-carboxylic acid, 1-methyl-2(1H)-pyridone-3-carboxylic acid, 6-methylthionicotinic acid, 3-quinolinic acid, 4-quinolinic acid, 7-chloro-3-quinolinic acid, 6-methoxy-3-quinolinic acid, isoquinoline-4-carboxylic acid, 5-chlorothiophene-2-carboxylic acid, pyrimidine-5-carboxylic acid, 5-methoxyindole-3-carboxylic acid, 1,2,5-thiadiazole-2-carboxylic acid, thiazole-5-carboxylic acid, 2-chlorothiazole-5-carboxylic acid, and 5-chloropyridazine-2-carboxylic acid. Substituents that can be positioned on the aromatic or heteroaromatic group include, but are not limited to, alkyl, halo, aryl, alkoxy, dialkylamino, alkylthio, hydroxy, hydroxyalkyl, and C(O) (alkyl or aryl).

The aryl group attached to the sulfone can be any group that sufficiently activates the acetylenic group to act as a dienophile toward the activated pyrrole and which does not interfere with the cycloaddition reaction. Nonlimiting examples are phenyl, p-alkylphenyl, including p-methylphenyl; halophenyl, and including p-chlorophenyl, p-fluorophenyl, and p-nitrophenyl. Fluoroalkanesulfonyl, including $CF_3SO_2$ and $C_4F_9SO_2$, can also be used to activate an aryl- or heteroarylacetylene.

Methods to prepare a wide variety of arylsulfonyl-(aryl or heteroaromatic)-acetylenes are described in Bhattacharya, S. N., et al, *Organomet. Chem. Synth.* 1, 145 (1970), and the reaction of an aryl or heteroaromatic trimethylsilyl acetylene (Sakamoto, T., et al., *Synthesis,* 312 (1983)) with tosyl chloride in the presence of a Lewis acid catalyst such as aluminum trichloride.

The process for preparing active compounds through the Diels-Alder reaction of an N-(electron withdrawing-substituted)pyrrole with an arylsulfonyl(optionally substituted aryl or heterocyclic)acetylene is set out in detail in the working examples below. These examples are merely illustrative, and not intended to limit the scope of the process or the compounds that can be made according to the process. As discussed above, this is a general method that can be combined with conventional synthetic techniques to provide a wide variety of products, all of which are considered to fall within the scope of the invention. The compounds are numbered as illustrated in FIG. 2.

EXAMPLE 26

Preparative of 1-(2-chloro-5-pyridyl)-2-phenylsulfonylethanone (9)

To a cold solution (−30° C.) of 20 g methyl phenyl sulfone in 400 ml dried tetrahydrofuran was added 128 ml 2.5M n-butyllithium (2.4 eq) slowly. The resulting solution was stirred at −30° C. for 30 minutes. A solution of 26 g 6-chloronicotinyl chloride in 100 ml tetrahydrofuran was then added during a 20 minute period. After stirring at the same temperature for 30 minutes, the mixture was quenched by addition of sat. ammonium chloride (ca. 100 ml). The organic layer was separated and the aqueous layer extracted with chloroform three times. The combined organic layer was washed with sat. brine and dried over magnesium sulfate. After removal of solvent, the brown solid was triturated with methanol (150 ml) to give 7.06 g of a slightly yellow solid. Another crop of the product (11.75 g) was obtained from the mother liqueur by chromatography on a short silica gel column using 50% ethyl acetate in petroleum ether as the eluent. The total yield is 18.81 g (49.7%). m.p. 152–3° C. MS(CI) m/z 296, 298(M+1).

In a similar manner, when the acid chlorides of nicotinic acid, isonicotinic acid, 5-chloronicotinic acid, 6-methylnicotinic acid, 6-methoxynicotinic acid, 6-phenylnicotinic acid, 6-methylthionicotinic acid, 2-chloropyridine-4-carboxylic acid, 2,6-dimethylpyridine-4-carboxylic acid, 1-methyl-2(1H)pyridone-3-carboxylic acid, 6-methylthionicotinic acid, 3-quinolinic acid, 4-quinolinic acid, 7-chloro-3-quinolinic acid, 6-methoxy-3-quinolinic acid, isoquinoline-4-carboxylic acid, 5-chlorothiophene-2-carboxylic acid, pyrimidine-5-carboxylic acid, 5- methoxyindole-3-carboxylic acid, 1,2,4-thiadiazole-2-carboxylic acid, thiazole-5-carboxylic acid, 2-chlorothiazole-5-carboxylic acid, 5-chloropyridazine-2-carboxylic acid are used in place of 6-chloronicotinyl chloride in the condensation reaction, the corresponding ketosulfones are obtained.

EXAMPLE 27

Preparation of 2-chloro-5-pyridyl phenylsulfonyl acetylene (22)

A solution of 3.34 g (11.3 mmol) of 20 in 100 ml dried tetrahydrofuran was added to a suspension of 840 mg 60% sodium hydride (washed with ethyl ether) in 100 ml tetrahydrofuran. After stirring 10 minutes, 1.88 ml (11.3 mmol) diethyl chlorophosphate was added in one portion. The mixture was stirred at room temperature overnight, then cooled to −78° C., and 1.35 g potassium t-butoxide is added in portions. The brown solution was stirred at −78° C. for another 10 minutes and allowed to warm to ca. −30° C. Water was added and the aqueous layer extracted with methylene chloride. After drying and evaporation in vacuo, the residue was purified on a silica gel column, and eluted with 25% ethyl acetate in petroleum ether. The white solid (1.2 g) obtained after evaporation of solvent has a m.p. 140–141° C. MS(CI) m/z 278, 280 (M+1), yield 38%.

In a similar manner, when other heterocyclic ketosulfones described in Example 26 are used in place of compound 20, the corresponding acetylenes are obtained.

EXAMPLE 28

(Preparation of N-carbomethoxy pyrrole (21 )

Potassium (5.85 g, 0.15 mol) was added to a solution of 10 ml pyrrole (0.145 mol) in 80 ml hot cyclohexane in several portions. The mixture was refluxed for 1 hour. To this cold solution was added 15 g (0.16 mol) methyl chloroformate slowly. After addition, the mixture was stirred at room temperature for 30 minutes. During this period, 2.5 ml dimethyl sulfoxide was added for catalysis. After quenching with ice-water, the organic layer was separated and the aqueous layer extracted with ether. The combined organic layer was washed with 10% sodium bicarbonate, sat. sodium chloride and dried over magnesium sulfate. Removal of solvent yielded 17.4 g of a liquid. Bulb to bulb distillation gives 16.5 g N-carbomethoxy pyrrole 21 as a colorless liquid, yield 91%. The product requires storage at −20° C.

In a similar manner, the N-carbomethoxy, N-carbobenzyloxy and N-tert-butoxycarbonyl derivatives of 2,5-dimethylpyrrole, 3,4-bis(trifluoromethyl)pyrrole, 2methylpyrrole, 2-methoxymethylpyrrole, 2-methylthiomethylpyrrole, 2-dimethylaminomethylpyrrole, methyl pyrrole-2 -acetate, 2-methoxymethoxyethylpyrrole, 3-benzyloxymethylpyrrole, 2-methoxypyrrole, 3-methoxypyrrole and 3-benzyloxypyrrole are prepared.

EXAMPLE 29
Preparation of 7-carbomethoxy-2-(2-chloro-5-pyridyl)-3-phenylsulfonyl-7-aza-bicyclo[2.2.1]-2,5-diene (23)

2-Chloro-5-pyridyl phenylsulfonyl acetylene 22 (1.12 g, 40.3 mmol) was dissolved in 8.0 g N-carbomethoxy pyrrole 21. The mixture was stirred in a covered flask at 80–85° C. for 24 hours. After evaporation in vacuo to recover N-carbomethoxy pyrrole, the residue was chromatographed on a silica gel column using 25% to 50% ethyl acetate in petroleum ether as eluent to recover 0.2 g of the acetylene 22 and obtain 1.21 g of a slightly dark product. The crude product was triturated with methanol to yield 0.94 g (58% or 70% according to recovered starting material) of a white solid. m.p. 101° C. MS(CI) m/z 403, 405 (M+1). When the arylsulfonyl acetylene derivatives described in Example 27 are used in place of compound 22 in this experiment, the corresponding Diels-Alder adducts are obtained.

EXAMPLE 30
Preparation of 7-carbomethoxy-5-(2-chloro-5-aza-bicyclo [2.2.1]hept-2-ene (24)

Compound 23 (0.726 g, 1.9 mmol) was dissolved in 50 ml anhydrous methanol and 7 ml dried tetrahydrofuran containing 1.0 g (8.0 mmol) of sodium dihydrophosphate. To this mixture was added 3.0 g 6% sodium amalgam in two portions at −20° C. under nitrogen. The stirred mixture was allowed to warm spontaneously to room temperature during a 2 hour period and stirred at room temperature for another hour. The upper layer was decanted and the residue washed with methanol. Water and 10% HCl were added to the combined methanolic extracts to bring the pH to 6 and most of the methanol removed in vacuo. The mixture was then extracted with methylene chloride. The combined organic layer was washed with sat. brine and dried over magnesium sulfate. After removal of solvent, the residue was purified on a silica gel column using 33% ethyl acetate in petroleum ether as the eluent to yield 215.3 mg (42.9%) of a colorless oil. $^1$H-NMR shows that it is a (1:2) mixture of exo and endo isomers. MS (CI) m/z 265, 267 (M+1). $^1$HNMR 6.01–6.53 (2H, $H_{5,6}$), 4.61–4.91 (2H, $H_{1,4}$). When other Diels-Alder adducts described in Example 29 are treated with sodium amalgam in a similar manner, the corresponding substituted 7-aza-bicyclo[2.2.1]hept-2-enes are obtained.

EXAMPLE 31
Preparation of 7-carbomethoxy-2-(2-chloro-5-pyridyl)-7-aza-bicyclo[2.2.1]heptane (25)

Compound 24 (178.4 mg, 0.674 mmol) (mixture of isomers) was dissolved in 10 ml methanol containing 5 mg 10% Pd-C. The mixture was hydrogenated under 1 atm. of hydrogen. After 18 ml of hydrogen was absorbed (5 minutes), the catalyst was removed by filtration and methanol removed in vacuo to give 165 mg (92%) of colorless oil. $^1$H-NMR indicates that it is a (1:2) mixture of exo and endo isomers. MS(CI) m/z 267, 269 (M+1). $^1$H-NMR 4.21–4.44 (2H, $H_{1,4}$). In a similar manner, other substituted 7-azabicyclo[2.2.1]hept-2-enes described in Example 30 are hydrogenated to the corresponding substituted 7-aza-bicyclo [2.2.1]heptane analogs.

EXAMPLE 32
Preparation of racemic epibatidine (19) and endo-epibatidine (19')

Compound 25 (90 mg, 0.338 mmol) was dissolved in 2.5 ml hydrobromic acid (33% in acetic acid). The mixture was stirred at room temperature for 20 hours. After evaporation of the mixture in vacuo the residue was dissolved in water and extracted with ethyl ether to recover the starting material (26 mg). The aqueous layer was neutralized with potassium hydroxide to pH 11 and extracted with methylene chloride. The combined organic layer was washed with saturated brine and dried over magnesium sulfate. After removal of the solvent, the 56 mg residue was chromatographed on silica gel column using ethyl acetate, methylene chloride and sat. ammonia methanol (2:1:0.03) to give 18 mg (25%) of epibatidine (19) m.p. 50–51° and 20 mg (28.4%) of endo-epibatidine (19'). The spectral data for these compounds is provided in Table 3.

TABLE 3

| Spectra for data for epibatidine (19) and endo-epibatidine (19') | | |
|---|---|---|
| | epibatidine (19) | endo-epibatidine (191) |
| MS (CI) m/z | 209, 211 (M + 1) | 209, 211 (M + 1) |
| H$^1$-NMR | | |
| $H_{1,4}$, | 3.80 (t, 3.9Hz), 3.56 (br. s) | 3.76 (q, 4.8Hz) |
| $H_{3e}$ | 1.90 (dd, 12.0, 9.0Hz) | 2.12 (tdd, 12.3, 4.8, 3.3Hz) |

The N-acetyl derivatives of epibatidine can be prepared from epibatidine and acetic anhydride in the presence of triethylamine. Likewise, other N-substituted 7-azabicyclo [2.2.1]heptanes described in Example 31 are deprotected to the corresponding free amine. The amines are readily acylated to the amide, alkylated to the tertiary amine and quaternary ammonium derivatives by using conventional methods. The amines also form stable and water-soluble salts with organic and inorganic acids as preferred in the pharmaceutical formulation.

EXAMPLE 33
Preparation of 7-carbomethoxy-2-(2- methoxypyridyl)-7-aza-bicyclo[2.2.1] heptane (29)

7-Carbomethoxy-2-(2-chloro-5-pyridyl)-7-aza-bicyclo [2.2.1]heptane 25 (20 mg, 0.076 mmol) was dissolved in 1.0 ml methanol containing 12.8 mg (0.2 mmol) potassium hydroxide. The mixture was refluxed for one hour, then concentrated and partitioned between ethyl ether and water. The aqueous layer was extracted with ether again and the combined organic layer was washed with sat. sodium bicarbonate, and dried over magnesium sulfate. Removal of solvent yielded a 10 mg residue. H$^1$-NMR shows it is a 1:2 mixture of exo and endo isomers of the title compound. H$^1$-NMR 3.92, 3.90 (2s, Py-OCH$_3$), 3.71, 3.66 (2s, NCOOCH$_3$).

EXAMPLE 34

Preparation of deschloro analogues of epibatidine (30)

N-carbomethoxy-5-(2-chloro-5-pyridyl)-7-aza-bicyclo[2.2.1]hept-2-ene 25 (16 mg) was dissolved in 3 ml methanol containing 7 mg 10% palladium on carbon. The mixture was hydrogenated under a slightly elevated pressure of hydrogen for one hour. After removal of catalyst and solvent, the residue was partitioned between ether and aqueous sodium bicarbonate. The aqueous layer was extracted with ether and the combined organic layer was dried over magnesium sulfate. Removal of solvent gave 10 mg of 7-carbomethoxy-2-(3-pyridyl)-7-azanorbornane (12). MS (CI) m/z 233 (M+1), $H^1$-NMR 3.72, 3.66 (2s, N—COOCH$_3$).

EXAMPLE 35

Preparation of 5,6-dehydro analogs of epibatidine

When the N-acylated 7-aza-bicyclo[2.2.1] hept-5-ene derivatives prepared in Example 30 are acid hydrolyzed under conditions similar to that described in Example 32, the corresponding 5,6-dehydro analogs of epibatidine (19) and its endo-isomer (19') are obtained.

EXAMPLE 36

Preparation of 1,4-dimethyl-2-(6-chloro-3-pyridyl)-3-phenylsulfonyl-7-carbomethoxy-7-aza-bicyclo[2.2.1]hept-2,5-diene A mixture of 0.14 g (0.5 mmol) 2-chloro-5-pyridyl phenylsulfonyl acetylene(22) and 0.7 g 2,5-dimethyl-N-carbomethoxypyrrole (31) was heated and maintained at 85° C. for 48 hour. The excess pyrrole (31) was removed in vacuo and the dark residue chromatographed on silica gel using 25%–33% ethyl acetate in petroleum ether as eluent, yielding 76 mg (35%) of the title compound. MS(CI) m/z 431, 433 (M+1). $H^1$-NMR 6.79, 6.55 (AB J=5.4 Hz, $H_{5,6}$), 3.52 (s, 3H, N—COOCH$_3$), 1.96, 1.68 (2s, 6H, 2CH$_3$).

EXAMPLE 37

Preparation of benzoyl phenylsulfonyl methane (32)

A procedure similar to the preparation of compound 20 was used. The product was obtained in 60% yield as a white crystal (crystallized from carbon tetrachloride). m.p. 91–93° C. (lit, m.p. 93–94° C.).

When the acid chloride of 4-chlorobenzoic acid, 3-methoxybenzoic acid, 3,4-methylenedioxybenzoic acid, 3,4,5-trimethoxybenzoic acid, 3-trifluoromethylbenzoic acid, 3-dimethylaminobenzoic acid, 4-methylthiobenzoic acid, 4-methylsulfinylbenzoic acid, 4methylsulfonylbenzoic acid, 3,5-difluorobenzoic acid, 2-naphthoic acid, 4-dimethylamino-2-naphthoic acid, 6-methoxy-2-naphthoic acid, 2-phenylpropionic acid and 2-(3,4-methylenedioxyphenyl) propionic acid are used in place of benzoyl chloride above, the corresponding substituted ketosulfones are prepared.

EXAMPLE 38

Preparation of phenyl phenylsulfonyl acetylene (34)

A procedure similar to the preparation of compound 22 was used. Chromatography of the crude product on silica gel using 5% ethyl acetate in petroleum ether as the eluent yielded 20% of the acetylene 34 as a solid.

Using a similar procedure, the other ketosulfones described in Example 37 are converted to the corresponding substituted aryl and aralkyl acetylenic derivatives.

EXAMPLE 39

Preparation of 7-carbomethoxy-2-phenyl-3-phenylsulfonyl-7-azanorborna-2,5-diene (35)

Phenyl phenylsulfonyl acetylene 34 (84.3 mg, 0.35 mmol) was mixed with 0.42 g of N-carbomethoxy pyrrole (21). The mixture was heated to and maintained at 85° C. for 48 hours. After removal of the excess pyrrole, the residue was chromatographed on silica gel column and eluted with 25–33% ethyl acetate in petroleum ether to give 30 mg (23%) of the adduct as a colorless oil. MS(CI) m/z 368(M+1). $H^1$-NMR 7.05(s, 2H, $H_{5,6}$), 5.51, 5.48 (2s, 2H, $H_{1,4}$), 3.5(br.s. 3H, N—COOCH$_3$).

Using a similar procedure, cycloadditions of substituted pyrroles described in Example 28 and substituted acetylenic derivatives prepared in Example 38 give the corresponding 7-aza-bicyclo[2.2.1]hepta-2,5-diene adducts.

EXAMPLE 40

Preparation of 2-phenyl-7-aza-bicyclo [2.2.1]heptane (36)

The bicyclic adduct 35 was reductively desulfonated, hydrogenated and acid hydrolyzed as described in Examples 30, 31 and 32 to yield 36. Similarly, the other bicyclic adducts in Example 39 are converted to the corresponding 2-substituted aryl-7-aza-bicyclo[2.2.1]heptanes.

EXAMPLE 41

Preparation of 2-phenyl-7-aza-bicyclo[2.2.1]hept-5-ene (37)

The bicyclic adduct 35 is reductively desulfonated and acid hydrolyzed as described in Examples 30 and 32 to yield 37. Similarly, the other bicyclic adducts in Example 39 are converted to the corresponding 2-substituted aryl-7-aza-bicyclo[2.2.1]hept-5-enes.

EXAMPLE 42

Preparation of 5 and/or 6 substituted 2-aryl (or heteroaryl)-7-aza-norbornanes from the corresponding 7-N-acyl or 7-aza-2-aryl (or heteroaryl)-norborn-5-enes The 5 and/or 6-substituents are introduced by functioning the 5,6-bond through conventional reactions, e.g., additions, hydroboration, epoxidation followed by ring opening with nucleophiles (alkoxide, amine, azide, alkylsulfide, halide, hydroxide, etc.).

EXAMPLE 43

Preparation of 3-methyl-7-aza-2-exo-(2-chloro-5-pyridyl) bicyclo[2.2.1] heptane (38)

7-Carbomethoxy-2-(2-chloro-5-pyridyl)-3-phenylsulfonyl-7-azabicyclo[2.2.1]hept-2,5-diene (23) is hydrogenated in methanol containing 10% Pd-C until both double bonds are saturated. The product, 7-carbomethoxy-2-(2-chloro-5-pyridyl)-3-phenylsulfonyl-7-aza-bicyclo [2.2.1]heptane 39, is dissolved in dry tetrahydrofuran and treated with n-butyl lithium (1.1 eq) at −30 to 0° C., followed by methyl iodide (1-1 eq) in tetrahydrofuran. The reaction mixture is then stirred at room temperature and poured into iced water. The product is extracted with ether and washed with water. After drying and evaporation of the ether solution, the crude product is chromatographed on a silica gel column, using a mixture of petroleum ether and ethyl acetate (3:1 by volume) to yield stereoisomers of 7-carbomethoxy-2-(2-chloro-5-pyridyl)-3-methyl-3-phenylsulfonyl-7-aza-bicyclo[2.2.1]heptane (40). The alkylation products are each treated with sodium amalgam as in Example 30 to remove the phenylsulfonyl group, followed by acid cleavage of the 7-carbomethoxy group as in Example 32 to yield isomeric 3-methyl analogs of compound 8 and 8'.

Similarly, when methyl iodide is replaced by ethyl bromide, allyl bromide, benzyl chloride, methoxymethyl chloride and methoxyethyl methanesulfonate, and corresponding 3-ethyl, 3-allyl, 3-benzyl, 3-methoxymethyl and 3-methoxyethyl derivatives are obtained.

Other 2-aryl or 2-heteroaryl derivatives of 7-N-acyl-7-aza-3-phenylsulfonyl-bicyclo[2.2.1] hepta-2,5-diene described in Example 29 are likewise hydrogenated, converted to the sulfonyl carbanion, alkylated, desulfonated and deacylated to give the corresponding 3-alkyl or aralkyl analogs.

EXAMPLE 44

Preparation of 7-methyl-7-aza-2-exo-(2-chloro-5-pyridyl) bicyclo[2.2.1]heptane (41)

Epibatidine 19 prepared in Example 32 is alkylated with methyl iodide (1.1 eq) in dry tetrahydrofuran at room temperature, followed by the usual isolation procedure, to give the 7-N-methyl derivative.

Similarly, alkylation with ethyl iodide, isopropyl bromide, allyl bromide, cyclopropylmethyl bromide, benzyl chloride, 4-methoxybenzyl chloride, 3,4-dimethoxybenzyl chloride, phenethyl bromide, propargyl bromide, hydroxyethyl chloride and methoxyethyl iodide yield the corresponding 7-N-alkylated derivatives.

Other substituted 7-aza-bicyclo[2.2.1]heptane analogs described in the examples above are alkylated to their 7-N-alkyl is derivatives in the same manner.

The N-acetyl derivative of epibatidine in Example 7 is reduced to the N-ethyl derivative by the treatment of lithium aluminum hydride in dry tetrahydrofuran at room temperature. Similarly, the 7-N-propionyl, N-benzoyl, N-phenylacetyl and N-2-furoyl derivative of epibatidine are reduced to the corresponding 7-propyl, 7-benzyl, 7-phenethyl and 7-(2-furfuryl) derivatives.

EXAMPLE 45

Resolution of racemic compounds

The substituted 7-aza-bicyclo[2.2.1]heptane derivatives are resolved to their optical isomers by conventional methods including chromatography on a chiral column, fractional crystallization of diastereomeric salts of chiral acids and separation of the chiral ester or amide derivatives followed by regeneration of the optically pure enantiomers. (See Optical Resolution Procedures for Chemical Compounds, Vol. 1, Amines. by P. Newman, 1980 Optical Resolution Information Center, N.Y. 10471.)

EXAMPLE 46

Resolution of racemic epibatidine (19).

To a solution of racemic epibatidine 19 and triethylamine (1.1 eq) in methylene chloride is added (−)-menthyl chloroformate (1.1 eq). The reaction mixture is stirred at room temperature for 6 hours, washed with iced water and dried over magnesium sulfate. After evaporation of solvent, the residue is chromatographed on a silica gel column, using a mixture of petroleum ether and ethyl acetate (5:1 by volume) to yield a mixture of two diastereoisomers of 7-N-(−)-menthyloxycarbonyl derivatives of d- and l-epibatidine. Separation of the diastereoisomers by HPLC on a chiral column and treatment of each isomer with HBr/AcOH as in Example 32 yields the corresponding d and l-epibatidine.

EXAMPLE 47

Preparation of optical isomers of substituted 7-aza-bicyclo [2.2.1] heptane derivatives from chiral intermediates N-carbo-(−)-menthyloxy pyrrole is prepared from pyrrole and (−)-menthyl chloroformate by the method described above. The chiral pyrrole is treated with the sulfonyl acetylene 22 or 34 as in Example 29 to give a diastereoisomeric mixture of the chiral cycloadduct 7-aza-bicyclo[2.2.1]hepta-2,5-diene derivative. After treatment with sodium amalgam as in Example 30, the diastereoisomeric mixture of 2-exo-aryl-7-aza-bicyclo[2.2.1]hepta-5-ene derivatives is obtained. These diastereomers are separated by chromatography to give the d and l enantiomers. The optically active intermediates are each reduced and treated with HBr/AcOH to yield optically active epibatidine enantiomers. Similarly, other substituted 7-aza-bicyclo[2,2,1] heptane analogs are prepared from the corresponding chiral pyrroles and chiral cycloadducts.

EXAMPLE 48

Preparation of benzo[5a,6a] epibatidine (39)

Scheme 4 illustrates the preparation of compound 39.

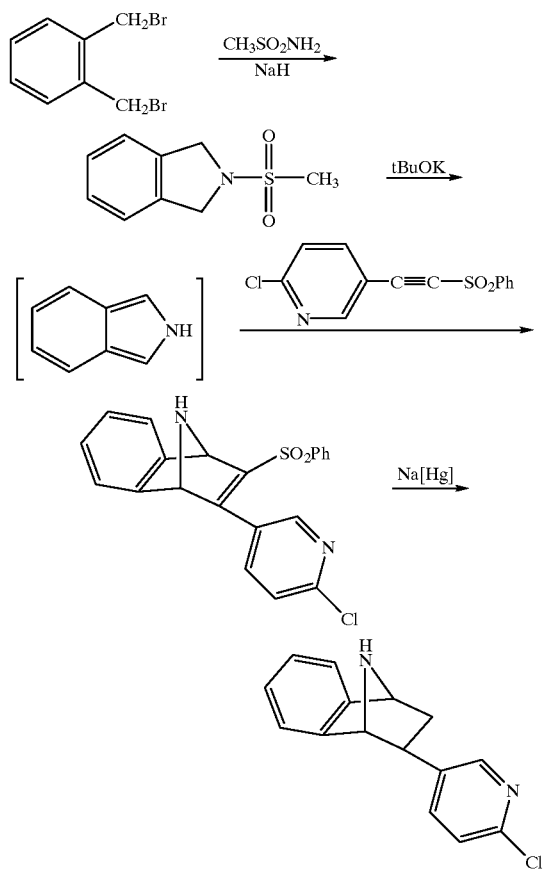

a) Preparation of N-methanesulfonyl isoindole (40)

Sodium hydride (0.88 g) was suspended in 3 ml dimethyl formamide. To this stirred solution was added methanesulfonamide (0.95 g, 10 mmol) in 5 ml dimethyl formamide dropwise under nitrogen. After stirring at 60° C. for 0.5 hours, a solution of 2.64 g (10 mmol) α,α'-dibromo-o-xylene in 7 ml DMF was added at a rate appropriate to maintain the temperature at 60–70° C. The mixture was stirred at room temperature for another hour, then quenched by pouring into water. The resulting precipitate was collected and washed with water, petroleum ether and ether successively. Weight 1.57 g (80%). $^1$H-NMR δ2.37 (s, 3H, —CH$_3$), 4.709 (s, 4H, 2CH$_2$). 7.25–7.35 (m. 4H, ArH).

b) Preparation of 2-(6-chloro-3-pyridyl)-3-phenylsulfonyl-1,4-dihydronaphthalene-1,4-imine (41)

Potassium t-butoxide (560 mg, 5.0 mmol) was dissolved in 3 ml DMSO under nitrogen. To this stirred solution was added 197 mg (1.0 mmol) N-methanesulfonyl isoindole in portions. After addition, the mixture was stirred at room temperature for 1.5 hours and quenched by addition of 3 ml water. After extraction with 45 ml ether, the combined organic layer was washed with saturated brine and dried over magnesium sulfate for 10 minutes. After filtration, the filtrate was combined with 83 mg (0.3 mmol) 1-(6-chloro-3-pyridyl)-2-phenylsulfonyl acetylene 22. The reaction mixture was stirred at room temperature overnight to evaporate in vacuo and chromatographed on silica gel column. Eluting with a mixed solvent (ethyl acetate, methylene chloride and ammonia in methanol) gave 108 mg blue residue. The color material was removed by washing the acidified material. After basification and extraction with ether, 62 mg of pure compound 41 was obtained as a foam. Yield 52%. MS(CI), 395, 397(M+1). $^1$H-NMR (CDCl$_3$): δ5.242 (d, J=1.5Hz, 1H), 5.362 (d, J=0.9Hz, 1H). (H$_1$ or H$_4$).

c) Preparation of exo and endo-benzo [5a,6a] epibatidine (39)

Compound 41 (54 mg, 0.137 mmol) was dissolved in a mixture of 3 ml methanol and 1 ml tetrahydrofuran. The solution was cooled to −20° C. and 66 mg 6% sodium amalgam was added. The mixture was stirred for 2 hours. The excess reagent was decomposed by water and the liquid layer was decanted out. After concentration of the liquid in vacuo, the residue was extracted with methylene chloride (3×5 ml). The combined organic layer was washed with saturated brine and dried over magnesium sulfate. After removal of solvent, the residue was separated on preparative thin layer chromatography with 33% methylene chloride in ethyl acetate to give 5.5 mg exo-benzo [5a,6a] epibatidine and 8.5 mg endo-benzo [5a,6a] epibatidine. Both isomers are an oil. Yields are 15% and 25% respectively. MS(CI), 257, 259(M+1). $^1$H-NMR (CDCl$_3$), (for exoisomer). 2.753 (dd, J=4.8, 8.4 Hz, 1H, H$_2$), 4.371 (s, 1H, H$_1$), 4.656 (d, J=4 Hz, 1H, H$_4$).

EXAMPLE 49

Preparation of N-methyl-benzo [5a,6a] epibatidine (42)

Scheme 5 illustrates a method for the production of N-methyl-benzo [5a, 6a ] epibatidine 42.

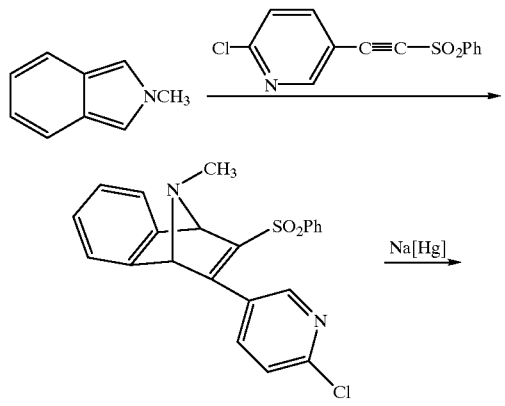

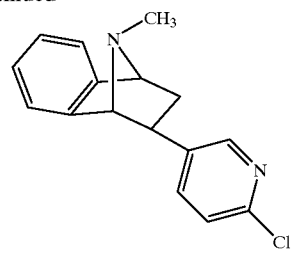

a) Preparation of N-methyl isoindole (43)

N-methyl isoindole was prepared according to the method set forth in B. Zeeh and K. H. König, Synthesis 1972, 45.

b) Preparation of 2-(6-chloro-3-pyridyl)-3-phenylsulfonyl-1,4-dihydronaphthalene-1,4-imine (44)

N-methyl isoindole (91 mg, 0.7 mmol) was mixed with 1-(6-chloro-3-pyridyl)-2-phenylsulfonyl acetylene 22 (139 mg, 0.5 mmol) in ethyl ether. After stirring at room temperature for 1 hour, the mixture was concentrated and chromatographed on silica gel column, eluting with ethyl acetate. This gave 204 mg of compound 44 as a clear oil. Yield 100%. MS(CI), 409, 411(M+1). H$^1$-NMR (CDCl$_3$). δ 2.36 (br, 3H, NCH$_3$), 4.805 (s, 1H), 4.93 (br.s., 1H), (H$_1$, or H$_4$).

c) Preparation of N-methyl-benzo [5a,6a] epibatidine (42)

Compound 44 (125 mg, 0.306 mmol) was dissolved in 10 ml methanol together with 4 ml tetrahydrofuran. The solution was cooled to −20° C. and 216 mg sodium dihydrophosphate was added to the solution followed by 1.0 g 6% sodium amalgam. The mixture was then stirred at room temperature for 3 hours and quenched with water. The organic layer was decanted out and concentrated in vacuo. The residue was extracted with methylene chloride (2×10 ml). The combined organic layer was washed with saturated brine and dried over magnesium sulfate. After removal of solvent, the residue was chromatographed on silica gel column eluting with 50% ethyl acetate in petroleum ether. This gave 19 mg (19%) exo-N-methyl-benzo[5a,6a] epibatidine. Further elution with a mixed solvent (ethyl acetate, methylene chloride and ammonia in methanol) yielded 55 mg (66%) of the endo-isomer. Total yield 85%. MS(CI), 271, 273(M+1). H$^1$-NMR (CDCl$_3$), (for exoisomer): 2.679 (dd, J=4.5, 8.7Hz, 1H, H$_2$), 3.935 (s, 1H, H$_1$), 4.203 (d, J=4.0Hz, 1H, H$_4$), 2.072 (s, 3H, NCH$_3$).

EXAMPLE 50

Preparation of N-formamidinyl epibatidine dihydrochloride (45)

Scheme 6 shows the preparation of compound 45.

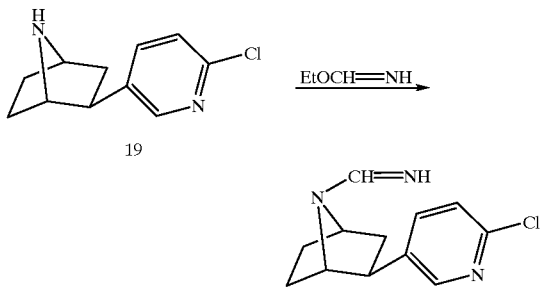

Racemic-epibatidine 19 (42 mg, 0.2 mmol) was mixed with 77 mg (0.7 mmol) freshly prepared ethyl formamidinate hydrochloride and 129 mg (1.0 mmol) diisopropyl ethylamine in 1 ml acetonitrile. After stirring at room temperature for 48 hours, the mixture was acidified with 1.0M hydrogen chloride in ether. After evaporation in vacuo, the residue was separated on silica gel preparative thin layer chromatography, using a solvent system of 25% methanol in chloroform, to give 25 mg of the compound 45 as a hygroscopic solid. Yield 36%. MS(CI), 236, 238 (free base M+1). $H^1$-NMR (CD$_3$OD). δ 3.40 (M, 1H, H$_2$).

EXAMPLE 51

The process of Example 50 was repeated with the replacement of ethyl formamidinate by S-methyl pseudothiourea, S-methyl-N-methyl pseudothiourea, S-methyl-N-nitro pseudothiourea, or methyl acetamidinate to form the N-guanidyl, N-methyl-guanidyl, N-nitroguanidyl and N-acetamidinyl epibatidine.

EXAMPLE 52

Preparation of N-formamidinyl deschloroepibatidine dihydrochloride (46)

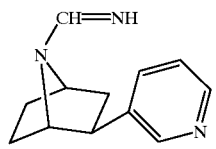

N-Formamidinyl epibatidine (12 mg, 0.04 mmol) 45 was dissolved in 2 ml methanol containing 5 mg 10% palladium on carbon. After hydrogenation under 1 atm hydrogen for 3 hours, the catalyst was removed by filtration. The filtrate was concentrated in vacuo to give 10 mg compound 46 as a hygroscopic solid. Yield 100%. MS(CI), 202(M+1 —2HCl). $H^1$-NMR (CD$_3$OD), δ 3.5 (M, 1H, H$_2$).

EXAMPLE 53

Preparation of 1-methyl epibatidine (47), and 4-methyl epibatidine (48)

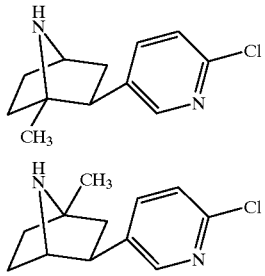

a) Preparation of 2-methylpyrrole (49)

2-Methylpyrrole was prepared according to the method set forth in J. Org. Chem. 28, 3052.

b) Preparation of N-t-butoxycarbonyl-2-methylpyrrole (50)

2-Methyl pyrrole (2.5 g) was dissolved in 6 ml tetrahydrofuran, and was slowly added to a suspension of 2.4 g 60% sodium hydride (washed with ether) in 30 ml tetrahydrofuran. A solution of 7.6 g di-t-butyl-dicarbonate in 20 ml of the same solvent was added to this cooled mixture. After shaking occasionally for 3 hours, it was decomposed carefully with water, and extracted with ether. The combined organic layer was washed with saturated brine and dried over magnesium sulfate. Removal of the solvent gave 6 g residue. Bulb-to-bulb distillation gave 4.5 g slightly yellow oil (ca. 80° C./5 mmHg). Yield 80%. MS(CI), 183(M+2). $H^1$-NMR (CDCl$_3$) δ 1.584 (s, 9H, 3CH$_3$), 2.421 (s, 3H, CH$_3$).

c) Preparation of 1- (and 4) -methyl-2-(6-chloro-3-pyridyl)-3-phenylsulfonyl-7-t-butoxycarbonyl-7-azanorborna-2,5-diene (51)

Compound 50 (10 mmol, 1.8 g) was mixed with 1-(6-chloro-3-pyridyl-2-phenylsulfonyl acetylene (22) 555 mg (2.0 mmol). The mixture was heated at 78° C. in a tightly covered flask under nitrogen for 24 hours. The mixture was separated on silica gel column eluting with 25% of ethyl acetate in petroleum ether. After recovery of 1.5 g of compound 50 and 120 mg compound 22, 636 mg of compound 51 was obtained as a yellow oil. Yield 69.3%. $^1$H-NMR showed that the oil is a 2:1 mixture of 1-methyl isomer and 4-methyl isomer. MS(CI), 459, 461. (M+1). $H^1$-NMR (CDCl$_3$), (for major isomer): 1.37 (s, 9H, 3CH$_3$), 1.748 (s, 3H, CH$_3$), 5.45 (d, J=3Hz, 1H, H$_4$). (For the minor isomer), 1.346 (s, 9H, 3CH$_3$), 1.958 (s, 3H, CH$_3$), 5.26 (d, 1H, J=3Hz, H$_1$).

d) Preparation of N-t-Boc-1 (and 4) -methyl epibatidine (52)

Compound 51 (1.0 mmol, 459 mg) was dissolved in a mixture of 20 ml methanol and 10 ml tetrahydrofuran. The solution was stirred and cooled to −20° C. To this solution was added 720 mg sodium dihydrophosphate followed by 1.5 g (6.0 mmol) 6% sodium amalgam. After stirring at room temperature for 2 hours, another 0.8 g of 6% sodium amalgam was added and stirring was continued for another 2 hours. The excess reagent was decomposed by water, and the solution was decanted out. After concentration of the solution at ambient temp in vacuo, the residue was extracted with methylene chloride (4×15 ml). The combined organic layer was washed with saturated brine and dried over magnesium sulfate. After removal of solvent, the residue (372 mg) was hydrogenated under 1 atm hydrogen in the presence of 8.4 mg platinum oxide for 2 hours. The catalyst was removed by filtration and the filtrate was concentrated in vacuo to a residue (360 mg). Separation took place on a silica gel column eluting with 17% ethyl acetate in petroleum ether. 95 mg of the endo-isomers and 65 mg of the exo-isomers were obtained. Total yield 50%. MS(CI), 323, 325(M+1). $H^1$-NMR (CDCl$_3$) (for exo isomer major), 2.78 (dd, 1H, J=5.4Hz, 7.8Hz, $H_2$), 4.45 (t, 1H, J=4.5Hz, $H_4$).

e) Preparation of 1-methyl epibatidine (47) and 4methyl epibatidine (48)

The exo-isomer of compound 52 (65 mg) was dissolved in 5 ml methylene chloride. To this cooled solution (0° C.) was added 2.5 ml trifluoroacetic acid. The resulting pink solution was then stirred at room temperature for 1.5 hours. After neutralization with 4.5 g potassium carbonate in 10 ml water, the organic layer was separated and the aqueous layer was extracted with methylene chloride. The combined organic layer was washed with saturated brine and dried over magnesium sulfate. Removal of solvent and separation on silica gel preparative thin layer chromatography developing with a mixed solvent (ethyl acetate, methylene chloride and ammonia in methanol) gave 6 mg of 4-methyl epibatidine 48 and 12 mg 1-methyl epibatidine 47. Total yield 40.2% MS(CI), 223, 225(M+1). $H^1$-NMR (CDCl$_3$), (for 1-methyl epibatidine, major, exo-isomer). δ 2.657 (dd, J=4.8, 8.7Hz, 1H, $H_2$), 3.694 (t, J=4.7Hz, 1H, $H_4$). (For 4-methyl epibatidine, minor exo-isomer): 2.887 (dd, J=4.7Hz, 1H, $H_2$), 3.486 (d, J=4.5Hz, 1H, $H_1$).

EXAMPLE 54

Preparation of 2-(2-fluoro-5-pyridyl)-7-azanorbornane (53)

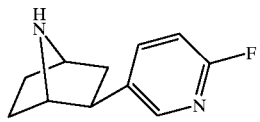

a) Preparation of 1-(2-fluoro-5-pyridyl)-2-phenylsulfonyl ethanone (54)

The method set forth in Example 26 was used, replacing 6-chloronicotinyl chloride with 6-fluoronicotinyl chloride (see Anderson et al; J. Med. Chem, 1990, 33(6) 1667), providing compound 54 as a white crystal, mp. 127–128° C. Yield 72%. MS(CI), 280(M+1). $H^1$-NMR (CDCl$_3$). δ 2.70 (s, 2H, CH$_2$).

b) Preparation of 1-(2-Fluoro-5-pyridyl)-2-phenylsulfonyl acetylene (55)

Use of the method set forth in Example 27 gave compound 55 in 62% yield from compound 54 as a white solid. mp. 97–98.5° C. MS(CI) 262(M+1).

c) Preparation of 7-carbomethoxy-2-(2-fluoro-5-pyridyl)-3-Phenylsulfonyl-7-azabicyclo[2.1.1]-hepta-2,5-diene (56)

Use of the method set forth in Example 29 gave compound 56 in 66% yield plus 22% of recovered acetylene 55.

Compound 56 is a white cubic crystal, mp. 85–87° C. MS(CI) 387(M+1). $H^1$-NMR (CDCl$_3$), 3.446 (br.s., 3H, CH3), 5.459 (d, J=7.2Hz, 2H, $H_{1,4}$).

d) Preparation of 7-carbomethoxy-5-(2-fluoro-5-pyridyl)-7-azabicyclo[2.2.1]hept-2-ene (57)

Use of the method set forth in Example 30 gave compound 57 as a 1:2.5 mixture of exo and endo isomers in a total yield of 64% from compound 56. MS(CI) 249(M+1). $H^1$-NMR (CDCl$_3$), (for endo-isomer). 3.682 (s, 3H, OCH$_3$), (for exo-isomer, 3.655 (s, 3H, OCH$_3$).

e) Preparation of 7-carbomethoxy-2-(2-fluoro-5-pyridyl)-7-azabicyclo[2.2.1]heptane (58)

Use of the method set forth in Example 31 gave compound 58 as a colorless oil in a yield of 93.3% from compound 57. MS(CI) 251(M+1). $H^1$-NMR (CDCl$_3$), (for endo-isomer), δ 3.722 (s, OCH$_3$), (for exo-isomer) δ 3.671 (s, 3H, OCH$_3$).

f. Preparation of 2-(2-fluoro-5-pyridyl)-7-azanorbornane (53)

The method set forth in Example 32 was used to produce 23 mg (16.2%) of the exo-isomer of compound 53 and 54.8 mg (38%) of the endo isomer of compound 53, as an oil from 185 mg of Compound 58 (0.74 mmol). MS(CI) 193(M+1). $^1$H-NMR (CDCl$_3$). δ 2.763 (dd, J=0.8, 9.0Hz, 1H, $H_2$), 3.532 (s, 1H, $H_1$), 3.769 (t, J=3.6Hz, 1H, $H_4$). (For endo-isomer). δ 3.324 (dt, J=12Hz, 5.7Hz, 1H, $H_2$), 3.779 (q, J=5.1Hz, 2H, $H_{1,4}$).

EXAMPLE 55

Preparation of 2-(2-chloro-3-pyridyl)-7-azanorbornane (59)

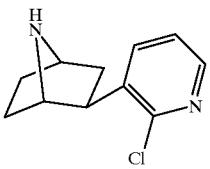

a) Preparation of 1-(2-chloro-3-pyridyl)-2-phenylsulfonyl ethanone (60)

Use of the method set forth in Example 26 gave compound 60 in 74% yield from 2-chloronicotinyl chloride as white solid, mp. 103–104° C. MS(CI) 296, 297(M+1). $H^1$-NMR (CDCl$_3$) δ 4.871 (s, 2H, —CH$_2$—).

b) Preparation of 1-(2-chloro-3-pyridyl)-2-phenylsulfonyl acetylene (61)

Use of the method set forth in Example 27 gave compound 61 in 27% yield from compound 60 as a white solid, mp. 90–94° C. MS(CI) 278, 280(M+1).

c) Preparation of 7-carbomethoxy-2-(2-chloro-3-pyridyl)-3-phenylsulfonyl-7-azabicyclo[2.2.1]hepta-2,5-diene (62)

Use of the method set forth in Example 29 gave compound 62 in 62.4% from 61 as an oil. MS(CI) 403, 405(M+1). $H^1$-NMR (CDCl$_3$), δ 3.612 (s, 3H, OCH$_3$). 5.429 (t, J=2.1Hz, 1H), 5.497 (t, J=2.1Hz, 1H).

d) Preparation of 7-carbomethoxy-5-(2-chloro-3-pyridyl)-7-azabicyclo[2.2.1]hept-2-ene (63)

Use of the method set forth in Example 30, gave compound 63 as the exo-isomer, 12%, and the endo-isomer, 35%. MS(CI) 265, 267(M+1). $H^1$-NMR (CDCl$_3$) (for exo-isomer). δ 3.66 (s, 3H, OCH$_3$), 6.502 (br.s. 2H, H$_{5,6}$). $H^1$-NMR (CDCl$_3$) (for endo-isomer). δ 3.686 (s, 3H, OCH$_3$), 4.882, 5.029 (2br.s. 2H, H$_{1,4}$). 5.88, 6.544 (2br.s., 2H, H$_{5,6}$).

e) Preparation of 7-carbomethoxy-2-(2-chloro-3-pyridyl)-7-azabicyclo[2.2.1]heptane (64)

Using the method set forth in Example 31, the exo-compound 63 was hydrogenated to give compound 64 in quantitative yield. MS(CI) 267, 269(M+1). $H^1$-NMR (DCCl$_3$) δ 3.277 (dd, J=4.5, 8.4Hz, 1H, H$_2$). 3.654 (s, 3H, OCH$_3$).

f) Preparation of 2-(2-chloro-3-pyridyl)-7-azanorbornane (59)

Use of the method set forth in Example 32, gave compound 59 from exo-compound 64, in 41% yield as an oil. MS(CI) 209, 211(M+1). $H^1$-NMR (CDCl$_3$) δ 3.162 (dd, J=4.8, 8.7Hz, 1H, H$_2$), 3.681 (s, 1H), 3.795 (t, J=3.6Hz, 1H), (H$_1$, H$_4$).

EXAMPLE 56

Preparation of 2-(2-chloro-4-pyridyl)-7-azabicyclo [2.2.1] heptane (65)

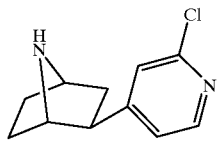

a) Preparation of 1-(2-chloro-4-pyridyl)-2-phenylsulfonylethanone (66)

Using the method set forth in Example 26, where 2-chloroisonicotinyl chloride (see Anderson et al., J. Med. Chem. 1990, 33(b), 1667) was used instead of 6-chloronicotinyl chloride, compound 66 was obtained in 51% yield as a white crystal, mp. 124–125.5° C. (methanol). MS(CI) 296, 298(M+1).

b) Preparation of 1-(2-chloro-4-pyridyl)-2-phenylsulfonyl acetylene (67)

Using the method set forth in Example 27, compound 67 was obtained in 54% yield from compound 66 as a white crystal, mp. 78–79° C. MS(CI) 278, 280(M+1).

c) Preparation of 7-carbomethoxy-2-(2-chloro-4-pyridyl)-3-phenylsulfonyl-7-azabicyclo[2.2.1]hepta-2,5-diene (68)

Using the method set forth in Example 29, compound 68 was obtained from compound 67 in 68% yield as a slightly brown oil. MS(CI) 403, 405(M+1). $H^1$-NMR (CDCl$_3$) δ 3.502 (br.s. 3H, OCH$_3$), 5.420, 5.483 (25, 2H, H$_{1,4}$), 7.065 (s, 2H, H$_{5,6}$).

d) Preparation of 7-carbomethoxy-5-(2-chloro-4-pyridyl)-7-azabicyclo[2.2.1]hept-2-ene (69)

Using the method set forth in Example 30, compound 69 was obtained from the desulfonation of compound 68 in 13.6% yield as a 1:2 mixture of exo- and endo-isomers. MS(CI) 265, 267(M+1). $^1$H-NMR (CDCl$_3$), (for endo-isomer) δ 3.682 (s, 3H, OCH$_3$), (for exo-isomer). δ 3.665 (s, 3H, OCH$_3$).

e) Preparation of 7-carbomethoxy-2-(2-chloro-4-pyridyl)-7-azabicyclo[2.2.1]heptane (70)

Using the method set forth in Example 31, compound 70 was obtained from the hydrogenation of compound 69 in 95% yield. MS(CI) 267, 269(M+1). $^1$H-NMR (CDCl$_3$) (for endo-isomer), δ 3.694 (s, 3H, OCH$_3$), (for exo-isomer). δ 3.655 (s, 3H, OCH$_3$).

f) Preparation of 2-(2-chloro-4-pyridyl)-7-azabicyclo[2.2.1]heptane (65)

Using the method set forth in Example 32, compound 65 was obtained from the deprotection of compound 70 in 23.6% (exo-isomer). MS(CI) 209, 211(M+1). $^1$H-NMR (CDCl$_3$), δ 2.738 (dd, J=9.0, 5.1Hz, 1H, H$_2$), 3.629 (d, J=2.4Hz, 1H), 3.791 (br.s., 1H). Some endo-isomer can be isolated.

EXAMPLE 57

Preparation of disodium 7-epibatidinylphosphate (71)

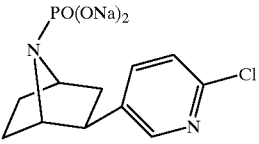

Epibatidine (40.0 mg) was dissolved in 3 ml phosphorous oxychloride and the mixture was refluxed for 3 hours in the absence of moisture. The excess reagent was removed in vacuo to give 100 mg 7-epibatidinyl phosphoryl dichloride as a brown oily residue. To 28 mg of this residue in 2 ml tetrahydrofuran was added 2 ml 1M sodium hydroxide in ice bath. The mixture was stirred at room temperature for another 4 hours. After evaporation of the organic solvent, the aqueous solution was washed with ethyl ether (2×5 ml). The aqueous layer was then evaporated in vacuo to ca. 0.5 ml and left to stand at room temperature for several hours to give compound 71 as a white crystal. Yield 14 mg (80%). $^1$H-NMR(D$_2$O) δ2.745 (p, J=4.5Hz, 1H, H2), 3.723 (br.s., 1H), 3.920 (br.s., 1H). 7.357 (d, J=8.4Hz, 1H). 8.073 (dd, J=2.4, 8.4Hz, 1H), 8.263 (d, J=2.4Hz, 1H). $^{31}$P-NMR (D$_2$O). 5.332. Chlorosulfonic acid or other N-sulfate reagents can be used in place of phosphorus oxychloride, under these reaction conditions to prepare the N-sulfate derivative of epibatidine and analogs thereto.

EXAMPLE 58

Preparation of 2,3-dehydroepibatidine (72)

Scheme 7 shows the production of compound 72.

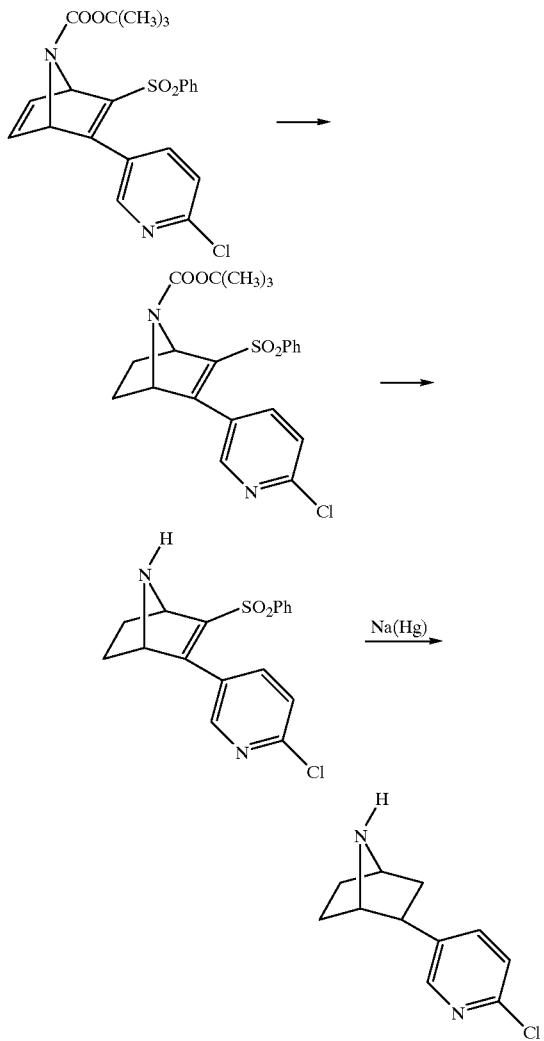

a) Preparation of 7-carbo-t-butoxy-2-(2-chloro-5-pyridyl)-3-phenylsulfonyl-7-azabicyclo[2.2.1]hepta-2,5-diene (73)

Using the method set forth in Example 29, compound 73 was obtained from the Diels-Alder reaction of 1-(2-chloro-5-pyridyl)-2-phenylsulfonylacetylene 22 with N-carbo-t-butoxy pyrrole (N-t-Boc-pyrrole) in 64% yield as a white solid. mp. 133–134° C. MS(CI) 445, 447(M+1).

b) Preparation of 7-t-boc-2-(2-chloro-5-pyridyl)-3-phenylsulfonyl-7-azabicyclo[2.2.1]hept-2-ene (73)

Adduct 73 (445 mg) was dissolved in a mixture of 20 ml methanol and 10 ml tetrahydrofuran containing 8 mg platinum oxide. After hydrogenation under 1 atm hydrogen for 3 hours, the catalyst was removed by filtration. The filtrate was concentrated in vacuo to give 440 mg residue. It was solidified after trituration in methanol. Yield 98%. MS(CI) 447, 449(M+1). $H^1$-NMR (CDCl$_3$) δ 1.266 (s, 9H, C(CH$_3$)$_3$), 4.905, 4.945 (2br.s., 2H, H2,4).

c) Preparation of 2-(2-chloro-5-pyridyl)-3-phenylsulfonyl-7-azabicyclo[2.2.1]hept-2-ene (75)

Using the method set forth in Example 53e, the t-Boc of compound 74 was easily deprotected by trifluoro acetic acid at 0° C. to give compound 75 in 95.4% yield as a white solid. MS(CI) 347, 349(M+1). $H^1$-NMR (CDCl$_3$) δ4.423 (d, J=4.2Hz, 1H), 4.500 (d, J=3.6Hz, 1H) (H$_{1,4}$).

d) Preparation of 2,3-dehydroepibatidine (72)

Compound 75 (365 mg) was desulfonated using the method set forth in example 30 to give 23 mg of compound 72 as a colorless oil. Yield 19%. MS(CI) 207, 209(M+1). $H^1$-NMR (CDCl$_3$) δ 4.323 (s, 1H, H$_1$), 4.574 (d, J=3.0Hz, 1H, H$_4$), 6.560 (d, J=2.4Hz, 1H, H$_3$).

EXAMPLE 59

Preparation of Chloroethylepibatidine (76)

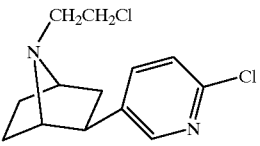

Using the method set forth in Example 44, epibatidine 19 was alkylated with 1-chloro-2-bromoethane to give compound 76 in a 35% yield as a clear oil. MS(CI) 271,273, 275(M+1). $H^1$-NMR (CDCl$_3$). δ 3.225, 3.476 (2S, 2H, H$_{1,4}$), 3.568 (t, J=6.6Hz, 2H).

EXAMPLE 60

Preparation of 2-(2-hydroxy-5-pyridyl)-7-azanorbornane (77)

Compound 53 (8.5 mg, 0.044 mmol) was dissolved in 1 ml tert-butanol. To this solution was added 1 ml 2M potassium hydroxide. After reflux for 20 hours and evaporation of butanol, the mixture was adjusted with 1M hydrochloric acid to pH 6–7. Evaporation of solvent in vacuo and purification of product with silica gel preparative thin layer chromatography developing with 20% 7N ammonia methanol in chloroform gave 4.2 mg compound 77 as an oil. Yield 50%. MS(CI) 191(M+1). $^1$H-NMR (CDCl$_3$) δ 2.554 (br.s., 1H, H$_2$), 3.503; 3.743 (2br.s., 2H, H$_{1,4}$).

EXAMPLE 61

Preparation of 2-(2-methylthio-5-pyridyl)-7-azanorbornane (78)

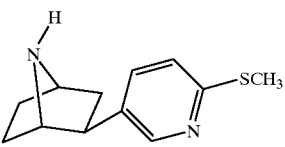

Using the method set forth in Example 33, compound 78 was obtained in 28% yield from sodium methylmercaptanide in ethanol as a colorless oil. MS(CI) 221, 223(M+1). $^1$H-NMR(CDCl$_3$) δ 2.542 (s, 3H, SCH3), 2.757 (dd, J=5.1, 8.7Hz, 1H, H$_2$), 3.546, 3.781 (2br.s., 2H, H$_{1,4}$).

EXAMPLE 62

Preparation of 5,6-bis(trifluoromethyl) deschloroepibatidine (79)

Scheme 8 shows the preparation of compound 79.

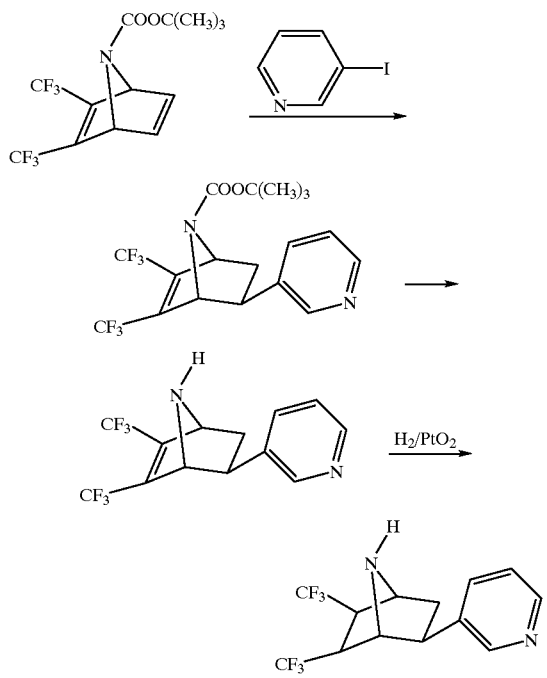

a) Preparation of 7-t-Boc-1,2-bis(trifluoromethyl)-7-azabicyclo[2.2.1]hepta-2,5-diene (80)

Compound 80 was prepared according to the procedure set forth in J. Leroy et al, Synthesis, 1982 313.

(b) Preparation of 7-t-Boc-2,3-bis(trifluoromethyl)-5-(pyridyl)-7-azabicyclo[2.2.1]hept-2-ene (81)

Compound 80 (165 mg, 0.5 mmol) and 105 mg 3-iodopyridine (0.5 mmol) were dissolved in 1 ml dimethyl formamide containing 9 mg palladium acetate, 21 mg triphenyl phosphine, 120 mg piperidine and 60 mg 88% formic acid. The mixture was stirred at 60–70° C. under nitrogen for 1.5 hours and at room temperature overnight. The solvent was removed in vacuo and the residue was partitioned between methylene chloride and water. The organic layer was separated and the aqueous layer was extracted with methylene chloride. The combined organic layer was washed with saturated brine and dried over magnesium sulfate. After removal of solvent in vacuo, the residue (218 mg) was separated in silica gel column eluting with 20% ethyl acetate in petroleum, to give 48 mg unstable compound 81 as a red oil. MS(CI) 409(M+1). Yield 23%. $^1$H-NMR (CDCl$_3$) δ 1.427 (s, 9H, OC(CH$_3$)$_3$), 2.974 (dd, J=4.2, 8.4Hz, 1H, H$_2$), 4.906, 5.147 (2br.s., 2H, H$_{1,4}$).

The 5-(2-chloro-5-pyridyl) analog was obtained by replacing the iodopyridine in the above reaction with 2-chloro-5-iodopyridine.

c) Preparation of 2,3-bis(trifluoromethyl)-5-pyridyl-7-azabicyclo[2.2.1]hept-2-ene (82)

Using the method set forth in Example 53e, compound 81 was easily deprotected with trifluoroacetic acid to give compound 82 in 90% yield. $^1$H-NMR (CDCl$_3$). δ 2.02 (dd, J=8.4, 2.1Hz, 2H, H$_3$), 2.88 (dd, J=4.8, 8.4Hz, 1H, H$_2$), 4.36, 4.63 (2br.s., 2H, H$_{1,4}$).

The 5-(2-chloro-5-pyridyl) analog was obtained in the manner set forth above.

d) Preparation of 5,6-bis(trifluoromethyl) deschloroepibatidine (79)

Compound 82 was hydrogenated under high pressure of hydrogen, providing compound 79.

5,6-Bis(trifluoromethyl) epibatidine was obtained in the manner set forth above.

C. SYNTHESIS OF 7-AZA-2-HETEROCYCLIC-BICYCLO[2.2.1]HEPTANES or HEPTENES

The syntheses described herein can be used to prepare 7-aza-2-heterocyclic-bicyclo[2.2.1]heptanes and heptenes. As described above, the dipolar cycloaddition of pentaamminesosmium-pyrrole complexes affords 2-carbomethoxy-7-azanorbornanes which are useful starting materials for 7-aza-2-heterocyclic-bicyclo[2.2.1]heptanes and heptenes. Reactions of these esters with acetamidoxime affords 7-aza-(1',2',4'-oxadiazoles)-bicyclo[2.2.1]heptanes and heptenes. Specific examples of these compounds are shown in Table 4. The analogous 7-benzyl and 7-unsubstituted compounds can be synthesized from the corresponding methyl esters described in Examples 66 and 67. The corresponding 3'-methyl-5'-2-(7-azanorbornyl) isoxazoles, can be synthesized via the reaction of the methyl esters such as those produced in Examples 72 and 73 with the dianion of acetone oxime.

TABLE 4

| R$_1$ | R$_2$ | R$_3$ |
|---|---|---|
| CH$_3$ | exo-CH$_2$NHCOCH$_3$ | H |
| CH$_3$ | exo-CH$_2$NHCOPh | H |
| CH$_3$ | exo-CH$_2$NHCONHPh | H |
| CH$_3$ | exo- (oxadiazole-CH$_3$) | H |
| CH$_3$ | exo- (oxadiazole-CH$_3$) | CH$_3$ |
| CH$_3$ | endo- (oxadiazole-CH$_3$) | H |

TABLE 4-continued

[Structure: bicyclic skeleton with substituents R1 (on N), R2, R3]

| R1 | R2 | R3 |
|---|---|---|
| CH3 | exo- [1,2,4-oxadiazol-5-yl linked to 4-methoxyphenyl] | H |
| CH3 | exo- [1,3,4-oxadiazol-2-yl with CH3] | H |
| CH3 | endo- [1,3,4-oxadiazol-2-yl with CH3] | H |
| ArCH2 | endo- COOCH3 | H |
| H | endo- COOCH3 | H |

EXAMPLE 63

Preparation of exo-2-acetamidomethyl-7-methyl-7-azabicyclo[2.2.1]heptane

A solution of the exo-2-aminomethyl-7-methyl-7-azabicyclo[2.2.1]heptane formed in Example 21 (27 mg, 0.19 mmol) in ether (3 mL) was treated with acetic anhydride (30 mg, 0.3 mmol). After 20 minutes, the reaction mixture was extracted with aqueous 10% $Na_2CO_3$. The organic phase was dried over $MgSO_4$, filtered, and evaporated, affording 29 mg (82%) of the title product. $^1H$ NMR (CDCl$_3$) δ 7.66 (br, s, 1H, NH), 3.24–3.14 (m, 3H, overlap of CH$_2$N and H4), 3.06 (d, J=3.9 Hz, 1H, H1), 2.18 (s, 3H, CH$_3$N), 1.91 (s, 3H, CH$_3$CO, 1.87–1.75 (m, 3H), 1.45 (m, 2H), 1.25 (m, 2H); $^{13}C$ NMR (CDCl$_3$) δ 170.5 (CO), 64.9 (CH), 61.5 (CH), 44.2 (CH$_2$), 40.6 (CH, C2), 35.3 (CH$_2$), 34.0 (CH$_3$N), 25.8 (CH$_2$), 25.4 (CH$_2$), 23.2 (CH$_3$).

EXAMPLE 64

Preparation of exo-2-benzamidomethyl-7-methyl-7-azabicyclo[2.2.1]heptane

The procedure described in Example 63 was followed, replacing acetic anhydride with benzoyl chloride. Purification of the crude product by column chromatography on silica gel (using ether containing 2% NH$_4$OH and 8% methanol) afforded the title product in 71% yield. $^1H$-NMR (CDCl$_3$) δ 9.16 (br s, 1H, NH), 7.86–7.4 (m, 5H, Ph), 3.5–3.3 (m, 3H overlap of CH$_2$N and H4), 3.18 (d, J=3.6 Hz, 1H, H1), 2.32 (s, 3H, CH$_3$N), 1.99–1.91 (m, 3H), 1.69–1.51 (m, 2H), 1.41–1.37 (m, 2H); $^{13}C$ NMR (CDCl$_3$) δ 167.4 (CO), 134.8 (C), 130.9 (CH), 128.3 (CH), 126.8 (CH), 65.4 (CH), 61.4 (CH), 44.8 (CH$_2$N), 40.0 (CH, C2), 35.4 (CH$_2$), 34.0 (CH$_3$), 25.6 (CH$_2$), 25.7 (CH$_2$).

EXAMPLE 65

Preparation of N-[exo-2-(7-methyl-7-azabicyclo[2.2.1]heptyl)methyl]-N$^1$-phenyl urea The procedure described in Example 63 was followed, replacing acetic anhydride with phenyl isocyanate. Purification by column chromatography on silica gel (ether containing 5% NH$_4$OH and 10% methanol) afforded the title product in 67% yield. $^1H$-NMR (CDCl$_3$) δ 7.30–6.9 (m, 5H, Ph), 6.89 (br s, 1H, NH) 3.3–3.2 (m, 3H, overlap of CH$_2$N and H4), 3.04 (d, J=3.3 Hz, 1H, H1), 2.6 (br s, 1H, NH), 2.07 (s, 3H, CH$_3$N), 1.86–1.81 (m, 3H), 1.51–1.43 (m, 2H), 1.33–1.29 (m, 2H); $^{13}C$ NMR (CDCl$_3$) δ 156.6 (CO), 138.9 (C), 129.0 (CH), 123.3 (CH), 121.0 (CH), 64.8 (CH), 61.4 (CH), 44.9 (CH$_2$N), 41.4 (CH, C2), 35.2 (CH$_2$), 34.1 (CH$_3$), 25.8 (CH$_2$), 25.5 (CH$_2$).

EXAMPLE 66

Preparation of exo-2,5'-(3'-methyl-1',2', 4'-ozadiazolyl)-7-methyl-7-azabicyclo[2.2.1]heptane The procedure set forth in Carrol et al., J. Med. Chem, 1993, 36, 2846 was used to prepare this compound. Sodium hydride (27 mg, 1.1 mmol) was added to a solution of acetamidoxime (77 mg, 1.04 mmol, 5 eg) in THF (10 mL) and the mixture was stirred and refluxed under nitrogen for 1 hour. Exo-2-carbomethoxy-7-methyl-7-azabicyclo[2.2.1] heptane (34 mg, 0.2 mmol) and powdered molecular sieves (85 mg) were added to the mixture and the reaction was refluxed and stirred for an additional 3 hours. The mixture was filtered, the cake was washed with THF, the filtrate was evaporated, and the residue was chromatographed on silica gel using 1% NH$_4$OH, and 3% methanol in ether. This provided the exo product as a colorless resin (12 mg, 31%). $^1$H NMR (CDCl$_3$) δ 3.66 (d, J=4.2 Hz, 1H, H1), 3.39 (t, J=4.2 Hz, 1H, H4), 2.93 (dd, J=9.3, 5.1 Hz, 1H, H2), 2.36 (s, 3H), 2.3 (m, 1H), 2.23 (s, 3H), 2.0–1.8 (m, 3H), 1.45 (m, 2H); $^{13}C$ NMR (CDCl$_3$) δ 182.3 (C), 167.4 (C), 65.8 (CH), 61.5 (CH). 41.4 (CH), 36.3 (CH$_2$), 35.1 (CH$_3$N), 26.8 (CH$_2$), 26.3 (CH$_2$), 12.0 (CH$_3$).

EXAMPLE 67

Preparation of exo-2,5'-(3'-methyl-1',2',4'-oxadiazolyl)-1,4-dimethyl-7-azabicyclo[2.2.1]heptane The procedure of Example 66 was used except that exo-2-carbomethoxy-1,4-dimethyl-7-azabicyclo[2.2.1]heptane was used in place of exo-2-carbomethoxy-7-methyl-7-azabicyclo[2.2.1]heptane. The product was purified by prep. GC on a OV-17 column (180° C.). $^1$H NMR (CDCl$_3$) δ 3.30 (dd, 1H), 2.37 (s, 3H), 2.15 (dd, 1H), 1.90 (m, 1H), 1.6–1.8 (5H), 1.44 (s, 3H), 1.05 (s, 3H); $^{13}$C NMR (CDCl$_3$) δ 181.9 (C), 166.8(C), 68.1(C), 66.6 (C), 46.4 (CH), 45.9 (CH$_2$), 38.6 (CH$_2$), 37.0 (CH$_2$), 20.6 (CH$_3$), 18.36 (CH$_3$), 11.5 (CH$_3$).

EXAMPLE 68

Preparation of endo-2,5'-(3'-methyl-1',2',4'-oxadiazolyl)-7-methyl-7-azabicyclo[2.2.1]heptane The procedure of Example 67 was repeated in the absence of molecular sieves using 2.25 eq of acetamidoxime and 3 eq NaH. This provided of exo and endo isomers. The isomers were separated by preparative TLC (2.0 mm plate, 2% saturated $NH_3$-methanol in ether; exo $R_f$=0.4, endo $R_f$=0.3) (isolated yields after chromatographic separation: 17%, 15%, respectively). Data for endo isomer: $^1$H NMR ($CDCl_3$) δ 3.61 (m, 2H, overlap of H1 and H2), 3.35 (t, J=4.5 Hz, 1H, H4), 2.40 (s, 3H), 2.36 (s, 3H), 2.3 (m, 1H), 1.9 (m, 1H), 1.8 (m, 1H), 1.6 (m, 1H), 1.4 (m, 1H), 1.15 (m, 1H), $^{13}$C NMR ($CDCl_3$) δ 180.5 (C), 166.8 (C), 65.0 (CH), 61.9 (CH), 37.9 (br, CH), 34.5 ($NCH_3$), 32.7 (br, $CH_2$), 28.1 (br, $CH_2$), 23.6 (br, $CH_2$), 11.5 ($CH_3$).

EXAMPLE 69

Preparation of exo-2,5'-(3'-[4'-methoxyphenyl]-1',2',4'-oxadiazolyl)-7-methyl-7-azabicyclo[2.2.1]heptane This compound was prepared using the procedure set forth in Example 68, replacing acetamidoxime with 4-methoxybenzamidoxime. $^1$H NMR ($CDCl_3$) δ 8.0 (d, J=9 Hz, 2H), 6.96 (d, J=9 Hz, 2H), 3.89 (s, 3H, $CH_3O$), 3.77 (d, J=4.2 Hz, 1H, H1), 3.41 (t, J=4.2 Hz, 1H, H4), 3.00 (dd, J=8.1, 4.2 Hz, 1H, H2), 2.47–2.38 (m, 1H), 2.24 (s, 3H, $CH_3N$), 2.04–1.85 (m, 3H), 1.55–1.42 (m, 2H); $^{13}$C NMR ($CDCl_3$) δ 181.8 (C), 167.9 (C), 161.7 (C), 129.1 (CH), 119.5 (C), 114.1 (CH), 65.5 (CH), 61.1 (CH), 55.3 ($CH_3O$), 41.2 (CH, C2), 35.6 ($CH_2$), 34.8 ($CH_3N$), 26.7 ($CH_2$), 26.1 ($CH_2$).

EXAMPLE 70

Preparation of endo-2,2'-(5'-methyl-1',3',4'-oxadiazolyl)-7-methyl-7-azabicyclo[2.2.1]heptane This compound was prepared using the method set forth in Ainsworth et al., J. Org. Chem., 1966, 31, 3442. A mixture of endo-2-carbomethoxy-7-methyl-7-azabicyclo[2.2.1]heptane (108 mg, 0.64 mmol), ethanol (2 mL), and hydrazine hydrate (0.44 g, 13.8 eq) was refluxed for 14 hours and the volatiles were removed in vacuo. The resulting crude hydrazide was refluxed in excess triethyl orthoacetate (0.86 g, 8.3 eq) for 18 hours. The mixture was acidified with HCl and the unreacted orthoester was evaporated. The residue was made basic with $NH_3$-methanol, triturated with methylene chloride, and filtered to remove the insoluble $NH_4Cl$. The filtrate was evaporated, and the crude material purified by preparative TLC (ether containing 7% of saturated $NH_3$-$CH_3OH$), providing 29 mg (24%) of the title product. $^1$H NMR ($CDCl_3$) δ 3.51–3.45 (m, 2H, overlap of H2 with H1 or H4), 3.31 (t, J=4.8 Hz, 1H, H4 or H1), 2.47 (s, 3H), 2.33 (s, 3H), 2.29–2.19 (m, 1H), 1.95 (m, 1H), 1.86–1.74 (m, 1H), 1.68–1.59 (m, 1H), 1.46–1.38 (m, 1H), 1.22–1.14 (m, 1H); $^{13}$C NMR ($CDCl_3$) δ 168.5 (C), 164.3 (C), 65.6 (CH), 62.4 (CH), 37.5 (br, CH), 35.1 ($NCH_3$), 32.8 (br, $CH_2$), 28.4 (br, $CH_2$, 23.8 (br, $CH_2$), 11.4 ($CH_3$).

EXAMPLE 71

Preparation of exo-2,2'-(5'-methyl-1',3',4'-oxadiazolyl)-7-methyl-7-azabicyclo[2.2.1]heptane The endo isomer produced in Example 70 (21 mg, 0.11 mmol) was refluxed in methanol (1 mL) containing potassium hydroxide (20 mg, 0.3 mmol) for 45 minutes. The methanol was evaporated, the residue was dissolved in water, and the resulting mixture was extracted with methylene chloride. The extract was dried and evaporated, affording 10 mg of a 1:1 mixture of exo and endo isomers. The isomers were separated using preparative TLC (acetonitrile containing 10% $NH_3$-methanol), affording the title product (3 mg, 15% based on recovered endo isomer). $^1$H NMR ($CDCl_3$) δ 3.59 (d, J=3.9 Hz, 1H, H1), 3.37 (t, J=4.2 Hz, 1H, H4), 2.93 (dd, J=9.3, 5.1 Hz, 1H, H2), 2.46 (S, 3H), 2.24 (s, 3H), 2.0–1.7 (m, 4H), 1.5–1.37 (m, 2H).

EXAMPLE 72

Preparation of 2-carbomethoxy-7-(3',5'-dimethylbenzyl)-7-azabicyclo[2.2.1]heptane The procedure used in the synthesis of 2-carbomethoxy-7-methyl-7-azabicyclo[2.2.1]heptane was used to make the title compound from 3',5'-dimethylbenzylpyrrole using the procedures set forth in Example 13 and 14. This title compound was obtained as a 1:3 mixture of exo/endo isomers in 27% yield. Data for major (endo) product: $^1$H NMR ($CDCl_3$) δ 7.0 (s, 2H), 6.9 (s, 1H), 3.85 (s, 3H), 3.53 (br s, 2H), 3.35 (m, 2H), 3.13 (m, 1H), 2.4 (m, 1H), 2.35 (s, 6H), 2.0 (m, 1H), 1.9–1.32(m, 4H).

EXAMPLE 73

Preparation of 2-carbomethoxy-7-azabicyclo[2.2.1]heptane

The product formed in Example 72 was treated with an equal weight of 10% Pd-on-C and refluxed in 96% formic acid for 12 hours. The mixture was filtered, the filtrate was partitioned between 10% aqueous $Na_2CO_3$ and methylene chloride, and the extract dried and evaporated, affording a 48% yield of the title compound. Major (endo) isomer: $^1$H NMR ($CDCl_3$) δ 4.12 (t, 1H), 3.92 (t, 3H), 3.8 (s, 3H), 3.2 (m, 1H), 2.3 (br s, 1H), 2.2–1.55 (m, 6H).

Figure 6:
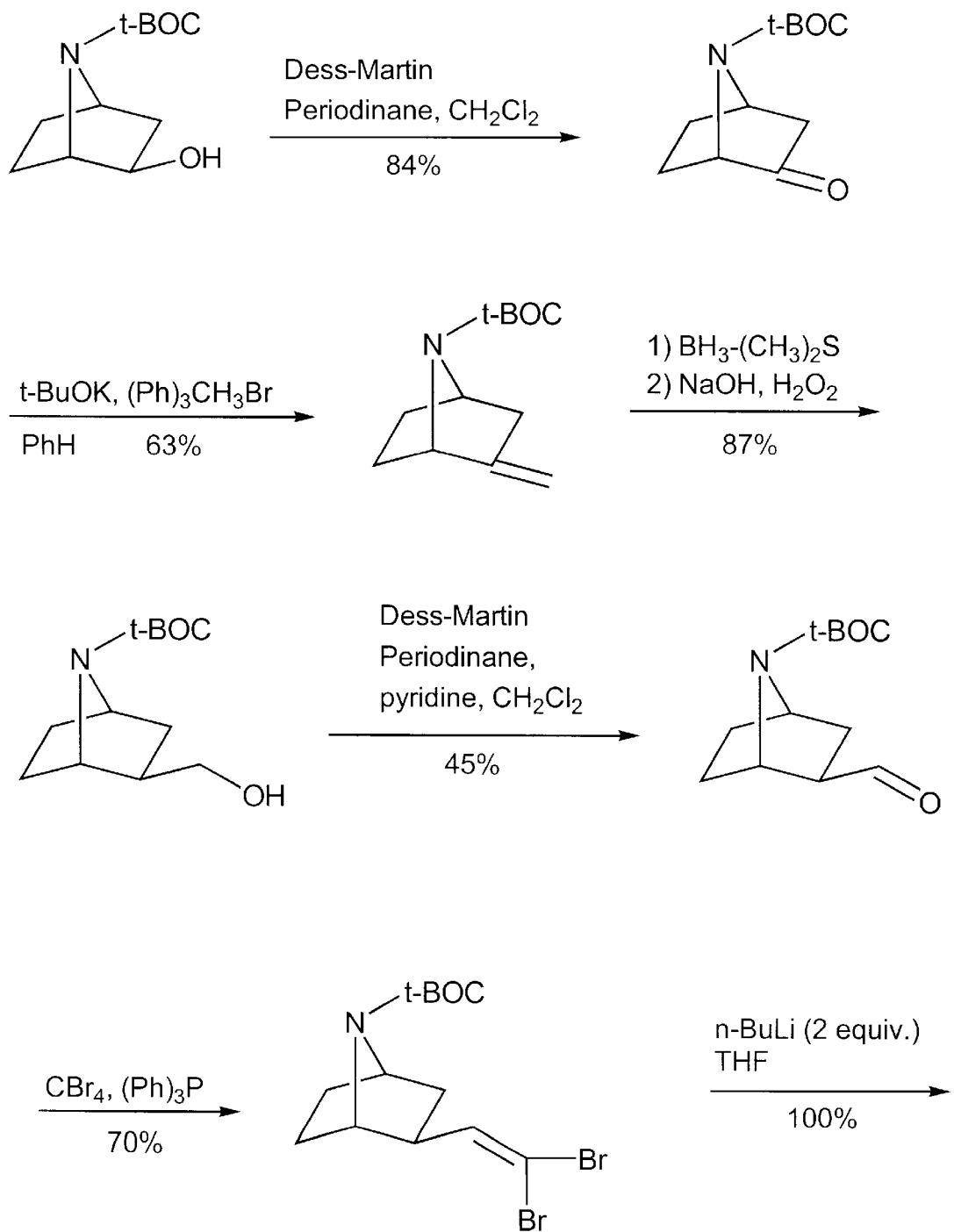
FIG. 6 is a schematic illustration of the synthesis of 7-methyl-7-aza-2-[isoxazolyl]-bicyclo[2.2.1]heptane.
Figure 6A:
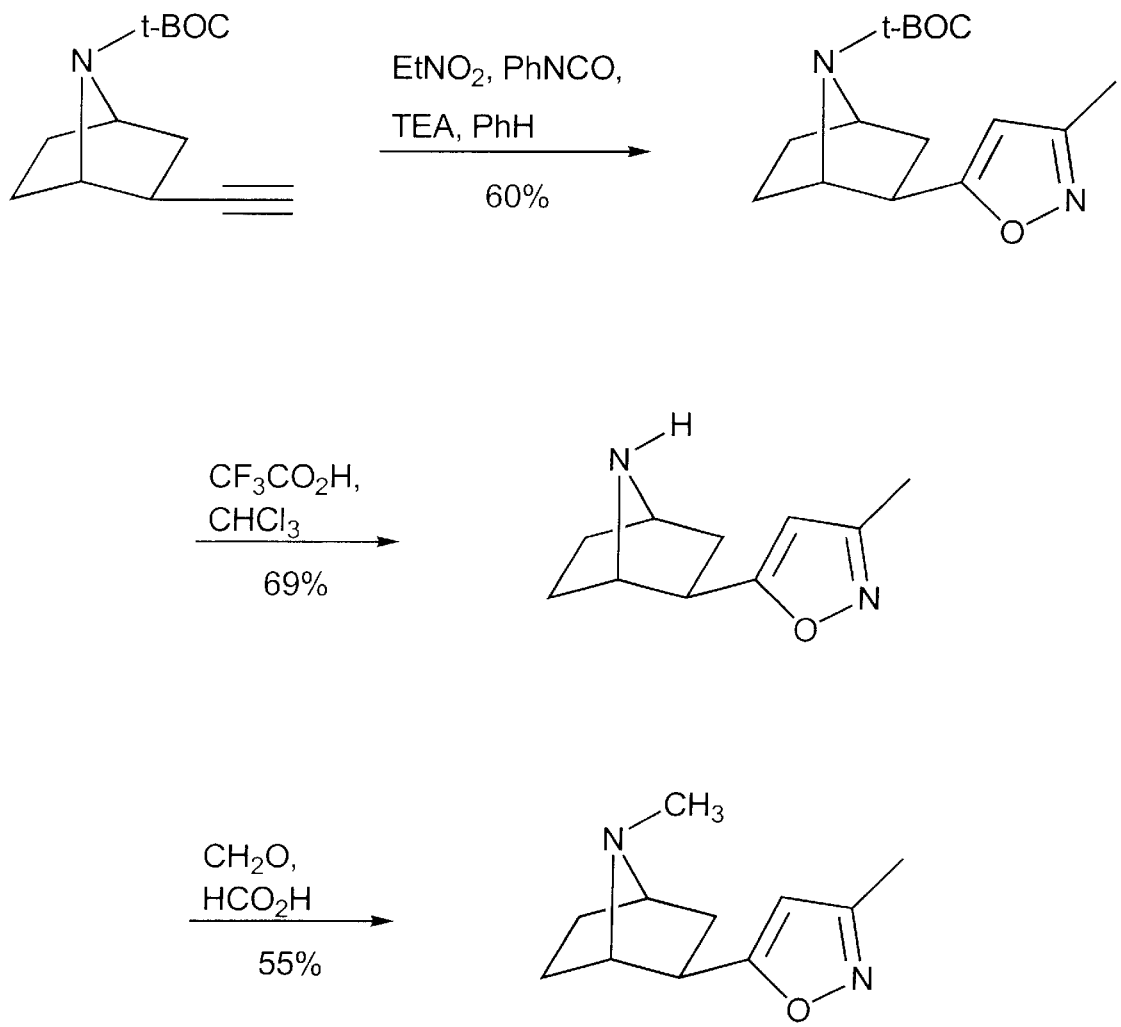

FIG. 6 provides examples of a synthetic route for production of 7-aza-2-isoxazole-bicyclo[2.2.1]heptane. This procedure is set forth in detail below in Examples 74 through 82.

EXAMPLE 74

Preparation of (+/−)-(exo)-7-(1,1-dimethylethoxycarbonyl)-7-azabicyclo[2.2.1]heptan-2-one (83)

A procedure similar to that set forth in Dess et al. J. Org. Chem. 1983, 48, 4156 was used prepare compound 83. The Dess-Martin periodinane (2.0 g, 4.70 mmol) was added to a stirred solution of 2-hydroxy-7-(1,1-dimethylethoxycarbonyl)-7-azabicyclo[2.2.1]heptane 82 (1.0 g. 4.72 mmol). After 12 hours the mixture was diluted with $Et_2O$ and poured into saturated aqueous $NaHCO_3$ containing a sevenfold excess of $Na_2SO_3$. The organic layer was washed with saturated aqueous $NaHCO_3$, and $H_2O$, dried over $MgSO_4$, filtered and concentrated. The resulting residue was purified by chromatography (20% EtOAc/hexanes) to give compound 83 (0.83 g, 84%) as a clear oil that solidified on standing.

EXAMPLE 75

Preparation of (+/−)-7-(1,1-dimethylethoxycarbonyl)-7-azabicyclo[2.2.1]heptan-2-ylidene (84)

A procedure similar to that set forth in Fitjer, et al., Synthetic Communications 1985, 15 (10), 855 was used to prepare compound 84. Methyl triphenylphosphonium bromide (1.55 g, 4.34 mmol) was added to a stirred solution of potassium tert-butoxide (0.53 g, 4.34 mmol) in absolute benzene (8.0 mL). The mixture was refluxed for 15 minutes and most of the solvent was evaporated off. Ketone 83 (0.83 g, 3.93 mmol) was added to the remaining slurry at 90° C. The reaction mixture was stirred at 90° C. for 2 hours, cooled, and partitioned between $H_2O$ (25 mL) and $Et_2O$ (80 mL). The aqueous layer was extracted with $Et_2O$ (3×80 mL). The combined organic layers were dried over $MgSO_4$, filtered and concentrated. The resulting residue was purified by chromatography (10% EtOAc/hexanes) to give compound 84 (0.52 g, 63%) as a clear oil. $R_f$ 0.72 (10% EtOAc/hexanes). $^1$H-NMR ($CDCl_3$, 300 MHz) δ 4.93 (s, 1 H), 4.73 (s, 1 H), 4.50–4.36 (m, 1 H), 4.34–4.20 (m, 1 H), 2.53–1.54 (m, 5 H) 1.43 (s, 9 H).

EXAMPLE 76

Preparation of (+/−)-(exo)-7-(1,1-dimethylethoxycarbonyl)-2-hydroxymethyl-7-azabicyclo[2.2.1]heptane 85

$BH_3°$ $(CH_3)_2S$ (1.75 mL, 2.0 M in THF) was added to a stirred, cooled (0° C.) solution of 84 (0.52 g, 2.49 mmol) in hexanes (6.0 mL). The cooling bath was removed. After 3 hours, ethanol (2 mL) was added followed by a mixture of NaOH (3 mL, 3 M), and $H_2O_2$ (30%, 3 mL). The mixture was heated at 40° C. for 2 hours, cooled and partitioned between brine and $Et_2O$. The aqueous layer was extracted with $Et_2O$ (3×25 mL). The combined organic layers were dried over $MgSO_4$, filtered, and concentrated to give compound 85 as a clear oil. $R_f$ 0.54 (50% EtOAc/hexanes). $^1$H-NMR ($CDCl_3$, 300 MHz) δ 4.34–4.00 (m, 2 H), 3.82–3.26 (m, 2 H), 3.00 (s, 1 H), 2.51–2.28 (m, 1 H), 2.08–0.68 (m, 15 H).

EXAMPLE 77

Preparation of (+/−)-(exo)-7-(1,1-dimethylethoxycarbonyl)-2-formyl-7-azabicyclo[2.2.1]heptane (86)

A procedure similar to that set forth in Danishefsky et al. *J. Org. Chem.* 1991, 56, 2535 was used to prepare compound 86. The Dess-Martin periodinane (0.89 g, 2.09 mmol) was added to a stirred solution of 85 (0.49 g, 2.17 mmol) and pyridine (0.62 g, 7.80 mmol). After 2 hours, the mixture was diluted with $Et_2O$ and poured into saturated aqueous $NaHCO_3$ containing a sevenfold excess of $Na_2S_2O_3$. The organic layer was washed with saturated aqueous $NaHCO_3$, with $H_2O$, dried over $MgSO_4$, filtered and concentrated. The resulting residue was purified by chromatography (40% EtOAc/hexanes) to give the title compound 86 (0.22 g, 45%) as a clear oil and a mixture of isomeric aldehydes (0.8 g). $R_f$ 0.86 (40% EtOAc/hexanes). $^1$H NMR ($CDCl_3$, 300 MHz) δ 9.79 (s, 1 H), 4.68–4.45 (m, 1 H), 4.41–3.83 (m, 1 H), 3.17–2.94 (m, 1 H), 2.11–1.05 (m, 15 H).

EXAMPLE 78

Preparation of (+/−)-(exo)-2-[1'-(2',2'-dibromo-1'-ethenyl)]-7-(1,1-dimethylethoxycarbonyl)-7-azabicyclo[2.2.1]heptane (87)

A procedure similar to that set forth in Corey, et al., *Tetrahedron Lett.* 1972, 3769 was used to prepare compound 87. Aldehyde 86 (0.22 g, 0.98 mmol) dissolved in $CH_2Cl_2$ was added to a stirred, cooled (0° C.) solution of CBr4 (0.72 g, 2.17 mmol) and triphenylphosphine (1.05 g, 4.0 mmol) in $CH_2Cl_2$ (5.0 mL). The reaction mixture was stirred 10 minutes, diluted with pentane and filtered through a Celite pad. The filter cake was washed with $Et_2O$ and the filtrate concentrated. The resulting residue was purified by chromatography (a linear gradient of 0–10% $Et_2O$/pentane) to give compound 87 as a clear oil that solidified on standing. $R_f$ 0.75 (10% $Et_2O$/pentane). $^1$H-NMR ($CDCl_3$, 300 MHz) δ 6.35 (d, J=8.7 Hz, 1 H), 4.40–4.00 (m, 2 H), 3.05–2.80 (m, 1 H), 2.32–2.05 (m, 1 H), 1.90–1.32 (m, 12 H).

EXAMPLE 79

Prepared of (+/−)-(exo)-2-(1'-ethynyl)-7-(1,1-dimethylethoxycarbonyl)-7-azabicyclo[2.2.1]heptane (88)

A procedure similar to that set forth in Corey, et al., *Tetrahedron Lett.* 1972, 3769 was used to prepare compound 88. n-BuLi (0.56 mL, 2.69 M in hexanes) was added to a stirred cooled (−78° C.) solution of the dibromide 87 (0.26 g, 0.68 mmol) in THF (7.0 mL). The reaction mixture was stirred at −78° C. for 1 hour, warmed to room temperature, and stirred 1 hour more. The reaction was quenched by the addition of $H_2O$ and partitioned with $Et_2O$. The aqueous layer was extracted with $Et_2O$. The combined organic layers were dried over $MgSO_4$, filtered and concentrated. The resulting residue was purified by chromatography (10% EtOAc/hexanes) to give compound 88 (0.16 g, 60%) as a clear yellow oil. $R_f$ 0.75 (10% EtOA/hexanes). $^1$H-NMR ($CDCl_3$, 300 MHz) δ 4.35–4.05 (m, 2 H), 2.94–2.73 (m, 1 H), 2.28–1.97 (m, 2 H), 1.89–1.24 (m, 13 H).

EXAMPLE 80

Preparation of (+/−)-7-(dimethylethoxycarbonyl)-2-[5'-(3'-methyl)isoxazolyl]-7-azabicyclo[2.2.1]heptane (89)

A procedure similar to that set forth in Kozikowski et al. *J. Org. Chem.* 1985, 50, 778 was used to prepare compound 89. A stirred solution of the alkyne 88 (0.16 g, 0.73 mmol), phenylisocyanate (0.69 g, 5.79 mmol), triethylamine (3 drops), and nitroethane (0.11 g, 1.45 mmol) in benzene was heated at 75–85° C. for 16 hours. The reaction mixture was cooled, and filtered. The filtrate was partitioned between $H_2O$ and hexanes. The organic layer was washed with saturated aqueous $NaHCO_3$, and with $H_2O$, dried over $MgSO_4$, filtered and concentrated. The resulting residue was purified by chromatography (linear gradient of 10–20% EtOAc/hexanes) to give compound 89 (0.12 g, 60%) as a light yellow semisolid. $R_f$ 0.33 (10% EtOAc/hexanes). $^1$H-NMR ($CDCl_3$, 300 MHz) δ 5.89 (s, 1 H), 4.50–4.37 (m, 1 H), 4.34–4.24 (m, 1 H), 3.50–3.37 (m, 1 H), 2.45–1.16 (m, 18H) ppm.

EXAMPLE 81

Preparation of 2-[5'-(3'-methyl)isoxazolyl]-7-azabicyclo[2.2.1]heptane, (90)

Trifluoroacetic acid (1.49 g, 13.0 mmol) was added to a stirred, cooled (0° C.) solution of the isoxazole 89 (56.4 mg, 0.212 mmol) in $CHCl_3$ (2 mL). After stirring for 18 hours, the volatile components were evaporated and the remaining residue partitioned between saturated aqueous $K_2CO_3$ and $CHCl_3$. The aqueous layer was extracted with $CHCl_3$. The combined organic layers were dried over $Na_2SO_4$, filtered, and concentrated to give compound 90 (41.2 mg, 69%) as a clear oil that formed a wax-like solid upon standing. The product could be further purified by chromatography (10% $CH_3OH/CHCl_3$). $R_f$ 0.33 (10% $CH_3OH/CH_2Cl_2$). $^1$H-NMR (CDCl$_3$, 300 MHz) δ 5.92 (s, 1 H), 4.10–3.87 (m, 2 H), 3.63–3.13 (m, 2 H), 2.42–2.11 (m, 4H), 1.89–1.32 (m, 5 H).

EXAMPLE 82

Preparation of 2-[5'-(3'-methyl)isoxazolyl]-7-methyl-7-azabicyclo[2.2.1]heptane (91)

A procedure similar to that set forth in Garvey et al. *J. Med Chem.* 1994, 37, 1055 was used to prepare compound 91. A stirred solution of the isoxazole 90 (19.3 mg, 0.18 mmol), formalin (0.32 mL, 37% in H$_2$O), and formic acid (0.22 mL, 88% in H$_2$O) was heated at 85–90° C. for 20 hours. The mixture was cooled to room temperature, treated with HCl (6M) and extracted with Et$_2$O. The aqueous layer was basified with saturated aqueous K$_2$CO$_3$ and extracted with CHCl$_3$. The combined organic layers were dried over MgSO$_4$, filtered, and concentrated. The resulting residue was purified by chromatography (10% CH$_3$OH/CH$_2$Cl$_2$) to give compound 91 (11.5 mg, 55%) as an oil. R$_f$ 0.52 (10% CH$_3$OH/CH$_2$Cl$_2$). $^1$H-NMR (CDCl$_3$, 300 MHz) δ 5.89 (s, 1 H), 3.63–3.24 (m, 3 H), 2.58–2.08 (m, 7 H), 1.97–1.13 (m, 5H).

EXAMPLE 83

Preparation of (+/−)-(exo)-7-(methoxycarbonyl)-2-(2'-quinolyl)-7-azabicyclo[2.2.1]heptane (92)

A procedure similar to that set forth in Regen, et al., *Tetrahedron Lett.* 1993, 7493 was used to prepare compound 92. N-Methoxycarbonyl-7-azabicyclo[2.2.1]heptene was added to a stirred solution of palladium acetate (5.6 mg, 0.0249 mmol), triphenylphosphine (12 mg, 0.046 mmol), piperidine (90 mg, 0.11 mmol), formic acid (38 mg, 0.83 mmol), and 2-iodoquinoline (21.8 mg, 0.86 mmol) in DMF (0.3 mL. The mixture was heated at 75° C. for 7 hours cooled, and partitioned between EtOAc (30 mL) and H$_2$O (10 ml). The organic layer was washed with H$_2$O (3×10 mL). The organic layer was dried over MgSO$_4$, filtered, and concentrated. The resulting residue was purified by chromatography (linear gradient of 20–40% EtOAc/hexanes) to give compound 92 (45.4 mg, 49%) as an oil. R$_f$ 0.33 (40% EtOAc/hexanes). $^1$H-NMR (CDCl$_3$, 300 MHz) δ 9.00–7.45 (m, 6H), 4.84–4.05 (m, 2H), 3.64 (s, 3H), 3.29–2.95 (m, 1H), 2.34–1.42 (m, 6H).

EXAMPLE 84

Preparation of (+/−)-(exo)-2-(2'-quinolyl)-7-azabicyclo[2.1.1]heptane (93)

A solution of 92 (45.4 mg, 0.168 mmol) in 33% HBr [(con.) in HOAc (con 9.0 ML)] was stirred for 30 hours. The solvent was evaporated and the resulting solid residue was dissolved in H$_2$O. The aqueous solution was basified with NaOH (2 N) and extracted with CH$_2$Cl$_2$ (4×10 mL). The combined organic layers were dried over MgSO$_4$, filtered and concentrated. The resulting residue was purified by chromatography (5% CH$_3$OH saturated with NH$_3$/CH$_2$Cl$_2$) to give compound 93 (21.5 mg, 60%) as an oil. R$_f$ 0.28 (5% CH$_3$OH saturated with NH$_3$/CH$_2$Cl$_2$). $^1$H-NMR (CDCl$_3$, 300 MHz) δ 9.03–7.37 (m, 6H), 4.00–3.57 (m, 2H), 3.10–2.87 (m, 1H), 2.32–1.13 (m, 7H).

EXAMPLE 85

Preparation of (+/−)-(exo)-7-methyl-2-(2'-quinolyl)-7-azabicyclo[2.2.1]heptane (94)

A procedure similar to that set forth in Garvey et al. *J. Med. Chem.* 1994, 37, 1055 was used to prepare compound 94. A stirred solution of the quinoline 93 (12.5 mg, 0.059 mmol), formalin (0.32 mL, 37% in H$_2$O), and formic acid (0.22 mL, 88% in H$_2$O) was heated at 85–90° C. for 20 hours. The mixture was cooled to room temperature, treated with HCl (6M) and extracted with Et$_2$O. The aqueous layer was basified with saturated aqueous K$_2$CO$_3$ and extracted with CHCl$_3$. The combined organic layers were dried over MgSO$_4$, filtered, and concentrated. The resulting residue was purified by chromatography (10% CH$_3$OH/CH$_2$Cl$_2$) to give compound 94 (9.3 mg, 70%) as an oil. R$_f$ 0.32 (10% CH$_3$OH/CH$_2$Cl$_2$). $^1$H-NMR (CDCl$_3$, 300 MHz) δ 8.97–7.89 (m, 6H, 3.63–3.39 (m, 2H), 3.11–2.92 (m, 1H), 2.45 (s, 3H), 2.29–1.00 (m, 6H).

EXAMPLE 86

Preparation of 2-(5'-oxazole)-7-methyl-7-azanorbornane (95)

2-Carbomethoxy-7-methyl-7-azanorbornane is obtained as set forth in Example 15. The compound is chromatographed on a silica gel column to separate the exo- and endo-isomers.

Figure 3:
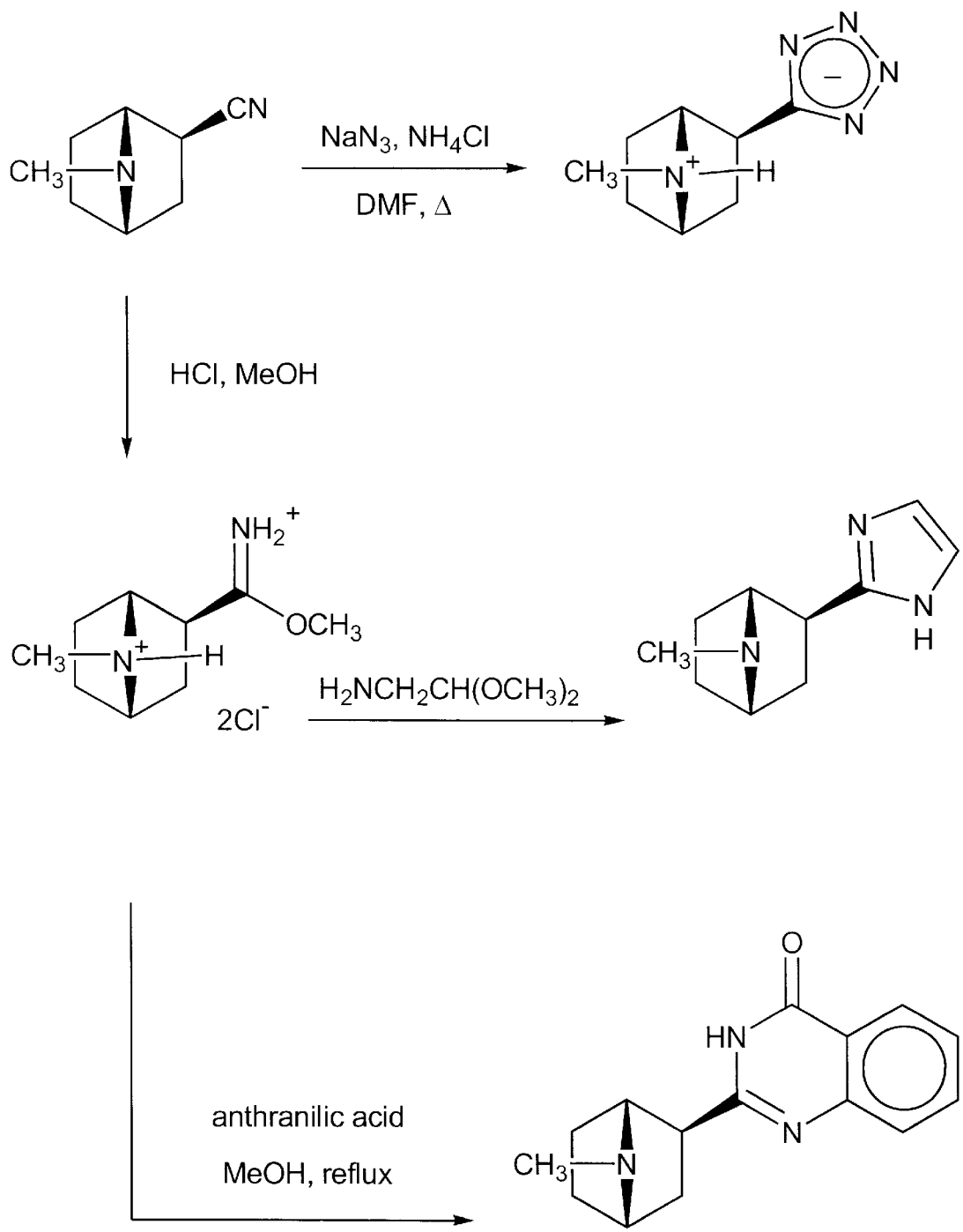
FIG. 3 is a schematic illustration of the synthesis of 7-aza-2-[oxazole and oxadiazole]-bicyclo[2.2.1]heptane from exo-2-carbomethoxy-7-methyl-7-azanorbornane.

Exo-2-carbomethoxy-7-methyl-7-azanorbornane is reacted with lithiomethyl isocyanide (the Schollkopf Reaction), as disclosed by Jacobi, P. A. et al., *J. Org. Chem.* 1981, 46, 2065, to produce 2-(5'-oxazole)-7-methyl-7-azanorbornane 95. This process is set forth in FIG. 3.

EXAMPLE 87

Preparation of 2-(1',3',4'-oxadiazole)-7-methyl-7-azanorbornane (96)

2-Carbomethoxy-7-methyl-7-azanorbornane is obtained as set forth in Example 15. The compound is chromatographed on a silica gel column to separate the exo- and endo-isomers.

Exo-2-carbomethoxy-7-methyl-7-azanorbornane is reacted using the procedure disclosed by Ainsworth, C. et al., *J. Org. Chem.* 1966, 31, 3442 to form the 2-(1',3',4'-oxadiazole)-7-methyl-7-azanorbornane. This reaction occurs by cyclizing an ethoxymethylene hydrazide intermediate with triethyl orthoformate, to produce the 2-(1',3',4'-oxzdiazole)-7-methyl-7-azanorbornane 96.

EXAMPLE 88

Preparation of 2-(tetrazole)-7-methyl-7-azanorbornane (97)

2-Cyano-7-methyl-7-azanorbornane is obtained as set forth in Example 16. The compound is chromatographed on a silica gel column to separate the exo- and endo- isomers.

Figure 4:
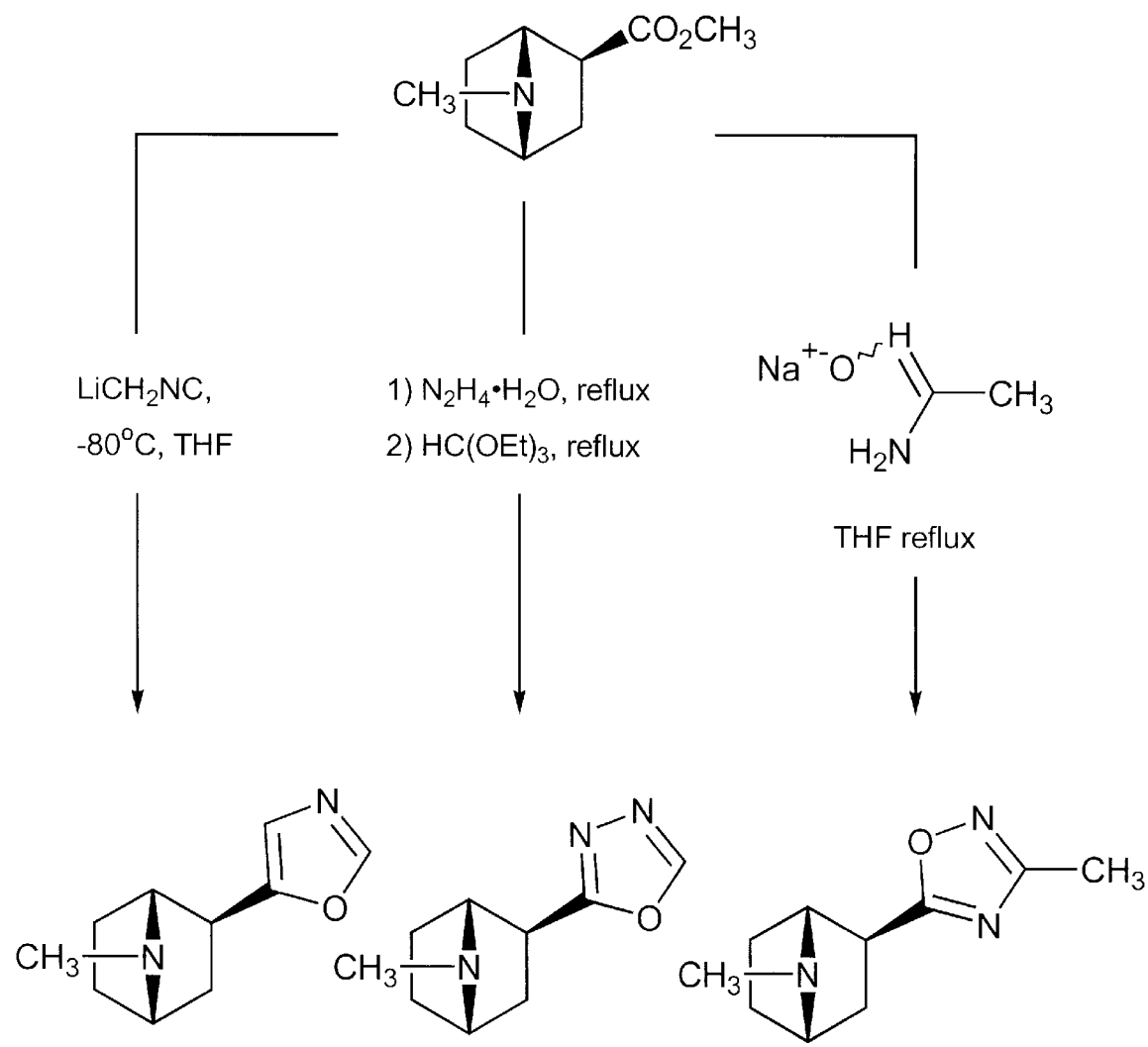
FIG. 4 is a schematic illustration of the synthesis of 7-aza-2-[heterocycles]-bicyclo[2.2.1]heptane from exo-2-cyano-7-methyl-7 -azanorbornane.

Exo-2-cyano-7-azanorbornane is converted in one step to the tetrazole 97, as shown in FIG. 4, using the procedure described by Kadaba, P. K. *Synthesis* 1973, 71.

EXAMPLE 89

Preparation of 2-(imidazole)-7-methyl-7-azanorbornane (98)

2-Cyano-7-methyl-7-azanorbornane is obtained as set forth in Example 16. The compound is chromatographed on a silica gel column to separate the exo- and endo- isomers.

Exo-2-cyano-7-methyl-7-azanorbornane is converted to the imidate ester intermediate 99, as shown in FIG. 4, using the Pinner reaction, as described by Patai, S., ed. *The Chemistry of Amidines and Imidates*, Wiley, 1975.

The imidate ester intermediate 99, is then converted to the 2-substituted imidazole 98, as shown in FIG. 4, using the reaction disclosed by Lawson, A., *J. Chem. Soc.* 1957, 4225.

EXAMPLE 90

Preparation of 2-(benzopyrimidinone)-7-methyl-7-azanorbornane (100)

2-Cyano-7-methyl-7azanorbornane is obtained as set forth in Example 16. The compound is chromatographed on a silica gel column to separate the exo- and endo- isomers.

Exo-2-cyano-7-methyl-7-azanorbornane is converted to the imidate ester intermediate 99, as shown in FIG. 4, using the Pinner reaction, as described by Patai, S., ed, *The Chemistry of Amidines and Imidates*, Wiley, 1975.

The imidate ester intermediate 99, is then converted to the 2-substituted benzopyrimidinone 100 using the reaction disclosed by Ried, W. et al., *Chem. Ber.* 1962, 95, 3042, as shown in FIG. 4.

EXAMPLE 91

Figure 5:
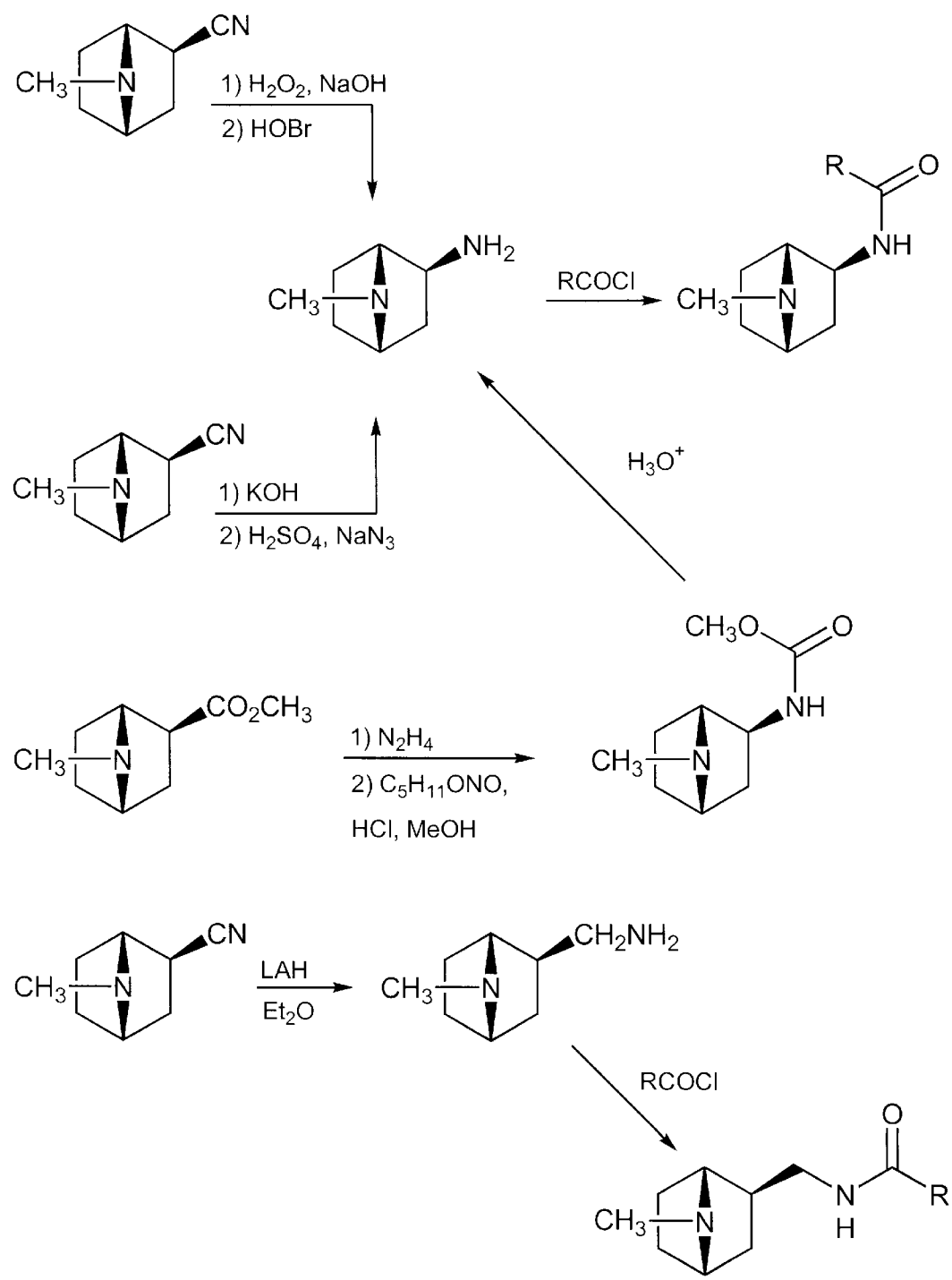
FIG. 5 is a schematic illustration of the conversion of exo-2-carbomethoxy-7-methyl-7-azanorbornane and exo-2-cyano-7-methyl-7-azanorbornane to 7-methyl-7-aza-2-[methylamino and methylacetamido]-bicyclo[2.2.1]heptane.

Preparation of 2-(acylamino)-7-methyl-7-azanorbornane and 2-(acylaminomethyl)-7-methyl-7-azanorbornane Either exo-2-cyano-7-methyl-7-azanorbornane or the exo-2-carbomethoxy-7-methyl-7-azanorbornane is converted to the exo-2-amino intermediate 101, as shown in FIG. 5. The exo-2-amino compound 101 may either be reacted to form heterocyclic rings, or may be acylated to provide open chain analogs, such as 102 and 103, as shown in FIG. 5. For example, the Hoffman rearrangement, using the method of Wallis, E. S. et al., *Org. Reactions* 1946, 3, 267, of the amide obtained by mild alkaline hydrolysis of the nitrile, or the Schmidt reaction of the corresponding acid, using the method of Wolff, H. *Organic Reactions* 1946, 3, 307, yields the exo-2-amine 101. Alternatively, hydrazinolysis of the exo-2-carbomethoxy compound, followed by a modified Curtius rearrangement may be used to prepare the carbamate 104, as shown in FIG. 5.

Alternatively, the 2-cyano moiety is reduced with lithium aluminum hydride to yield exo-2-aminomethyl compound 105, which may be acylated to give amide or carbamate open chain compounds 106.

IV. Pharmaceutical Compositions

Humans, equine, canine, bovine and other animals, and in particular, mammals, suffering from disorders characterized by increased or decreased cholinergic function, as described in more detail herein, can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, maphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated for any of the disorders described herein. A preferred dose of the active compound for all of the herein-mentioned conditions is in the range from about 0.0001 to 20 mg/kg, preferably 0.001 to 2 mg/kg per day, more generally 0.05 to about 0.5 mg per kilogram body weight of the recipient per day. A typical topical dosage will range from 0.001% to 0.5% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 0.001 to 1000 mg, preferably 0.01 to 500 mg of active ingredient per unit dosage form. A oral dosage of 0.1 to 200 mg is usually convenient.

The active ingredient can be administered by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose. The parental preparation can be enclosed in ampoules, disposable syringes or multiple dose vials made of glass or plastic. If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

V. Analgesic Activity of 7-Azabicyclo[2.2.1]-heptanes and -heptenes

A wide variety of biological assays have been used to evaluate the ability of a compound to act as an analgesic. Any of these known assays can be used to evaluate the analgesic ability of the compounds disclosed herein. The Straub-tail reaction, which is characteristic of opiate alkaloids, has been used as an assay for opiate agonists and antagonists. The assay is described in detail in *Br. J. of Pharmacol.* 1969, 36, 225. Another accepted assay for analgesic activity is the hot plate analgesia assay, described in *J. of Pharmacol. Exp. Therap.* 1953, 107, 385. An assay for the evaluation of the ability of a compound to bind to an opiate receptor is described in *Mol. Pharmacol.* 1974, 10, 868.

In addition to their potent central analgesic effects, some of the substituted 7-aza-bicyclo[2.2.1]-heptanes and -heptenes described herein also possess varying degrees of peripheral anti-inflammatory and analgesic effects which are useful for therapeutic applications. The following assays for the evaluation peripheral anti-inflammatory activities are described in Barber, A. and Gottschlich, R., Opioid Agonists nd Antagonists: An Evaluation of Their Peripheral Actions in Inflammation, Medicinal Research Review, Vol. 12, No. 5, 525–562 (September, 1992): paw hyperalgesia in rat that has been induced by prostaglandin E2 or carrageenan; inflamed knee joint in cat that has been induced by carrageenan, bradykinin or $PGE_2$; formalin test in mouse or rat that has been induced by formalin; neurogenic inflammation in rat, cat or guinea pig that has been induced by antidromic stimulation of sensory nerves; and the writhing test in mouse that is induced by acetic acid, phenylbenzoquinone, prostaglandin or bradykinin; and adjuvant arthritis in rat that is induced by Freund's adjuvant.

EXAMPLE 86

Evaluation of Analgesic Activity

Table 5 provides the analgesic activity measured as $ED_{50}$ ($\mu g/Kg$) for selected compounds disclosed herein, as determined using the Straub-Tail assay, as describe by J. Daily et al. *J. Am. Chem. Soc.,* 1980, 102, 830; T. F. Spande, et al. *J. Am. Chem. Soc.* 1992, 114, 3475; T. Li, et al. *Bioorganic and Medicinal Chemistry Letters* 1993, 3, 2759.

TABLE 5

| Structural formula | $ED_{50}$ $\mu g/Kg$ | Comments |
| --- | --- | --- |
|  | 9 ($\mu g/Kg$) | 1-epibatidine |
|  | 7.5 >100 | d-epibatidine |
|  | <10 |  |
|  | 10000 | Mixture of endo and exo isomers (1.3:1) |
|  | 750 |  |

TABLE 5-continued

| Structural formula | ED$_{50}$ µg/Kg | Comments |
|---|---|---|
| (N-CH₂-cyclopropyl azabicyclic, 6-chloropyridyl) | 100% @ 1000 (µg/Kg) | |
| (N-CH₂CH₂C₆H₅ azabicyclic, 6-chloropyridyl) | <1000 | |
| (NH azabicyclic, 3-pyridyl) | 250 | |
| (NH azabicyclic, 6-chloropyridyl, ene) | <1000 | |
| (N⁺(CH₃)₂ I⁻ azabicyclic, 6-chloropyridyl) | 100–200 | |
| (NH azabicyclic, 6-fluoropyridyl) | ca. 50 | |
| (NCH₂CH₂Cl azabicyclic, 6-chloropyridyl) | ca. 100 | |
| (NH azabicyclic, 6-fluoropyridyl, alternate) | ca. 10 | |

TABLE 5-continued

| Structural formula | ED$_{50}$ µg/Kg | Comments |
|---|---|---|
| (NH azabicyclic, 6-chloropyridyl) | 10 | racemic |
| (N-CH=NH·HCl azabicyclic, 6-chloropyridyl) | 99% @ 100 | |
| (NH azabicyclic, 6-OC(CH₃)₃-pyridyl) | ca. 1000 | |

EXAMPLE 87

Evaluation of Nicotinic Receptor Binding Activity

7-Aza-bicyclo[2.2.1]-heptanes and -heptenes were evaluated for their ability to bind to the acetylcholine nicotinic receptor using a standard binding assay, e.g. X. Zhang and A. Nordberg, *Arch. Pharmacol.*, 348, 28 (1993); R. E. Middleton and J. B. Cohen, *Biochemistry*, 30, 6987 (1991), with nicotine sulfate as the reference compound, rat cortex as the tissue substrate, and a [$^3$H]-NMCI radioligand. The results are provided in Table 6.

TABLE 6

| Structural Formula | Testing Level | Inhibition % |
|---|---|---|
| (NH azabicyclic, 6-chloropyridyl) | $10^{-7}$ M | 106 |
|  | $10^{-9}$ | 72 |
|  | $10^{-11}$ | 13 |
| (N-CH₃ azabicyclic, 6-chloropyridyl) | $10^{-7}$ | 102 |
|  | $10^{-9}$ | 77 |
|  | $10^{-11}$ | 10 |
|  | $10^{-7}$ | 102 |
|  | $10^{-9}$ | 22 |
|  | $10^{-11}$ | 5 |
| (NH azabicyclic, 3-pyridyl) | $10^{-5}$ | 104 |
|  | $10^{-7}$ | 103 |
|  | $10^{-9}$ | 103 |

TABLE 6-continued

| Structural Formula | Testing Level | Inhibition % |
|---|---|---|
| (CH₃)₂I⁻ N-bicyclic-pyridine-Cl | $10^{-5}$ M $10^{-7}$ $10^{-9}$ | 104 100 49 |
| CH=NH •2 HCl N-bicyclic-pyridine-Cl | $10^{-7}$ $10^{-9}$ $10^{-11}$ | 104 49 22 |
| CH=NH N-bicyclic-pyridine | $10^{-7}$ M $10^{-8}$ $10^{-9}$ | 103.9 71.3 5 |
| R-N-bicyclic-pyridine-Cl, R = H, R = CH₃ | $10^{-5}$ M $10^{-7}$ $10^{-5}$ | 103 24 81 |

EXAMPLE 88

Competition with Cytisine for Binding to Rat Cortex (Brain) Receptors

[$^3$-H](−)-Cytisine is a nicotinic cholinergic receptor ligand that binds with high affinity to the a4b2 subtype receptor, the major subtype in rodent brain accounting for >90% of (−)-nicotine binding sites (Flores, et al., 1992; Whiting, et al., 1992). This nicotinic receptor subtype is most sensitive to (−)-nicotine compared to other receptor subtypes (Connolly, et al., (1992). Compounds that compete with cytisine for the nicotinic cholineric receptor are considered nicotine receptor agonists.

A membrane fraction from rat brain cortex (Harlan Laboratories) was prepared using an adaptation of an established method (Pabreza, et al., 1991). Compound and [$^3$H]-(−)-cytisine (New England Nuclear, 42 Ci/mmol) were mixed before addition of membrane (0.5 mg protein) and incubated in glass tubes for 75 minutes on ice; total assay volume was 0.24 ml. Parallel assays to determine nonspecific binding were incubated in the presence of 10 uM (−)-nicotine (Sigma). Bound radioactivity was isolated by vacuum filtration onto glass microfiber filters (Whatman, GF-B) using millipore tubs, followed by 3×4 ml buffer wash. Filters were prerinsed with 0.5% polyethyleneimine prior to sample filtration to reduce nonspecific binding. Bound radioactivity was quantitated by scintillation counting.

Tables 7 and 8 provide the nicotine receptor IC$_{50}$ in nanomolar concentration for selected compounds.

TABLE 7

| Structure | Nicotine Receptor Cytisine IC$_{50}$ (nM) | Tail-Flick Assay ED$_{50}$ % Effect After 5 and 60 min. (mg/kg) | |
|---|---|---|---|
| CH₃-N-bicyclic-oxadiazole-CH₃ | 32,000 | −2.9 | −3.6 |
| CH₃-N-bicyclic-oxadiazole-CH₃ | 150 | 6.7 | 24.6 |

TABLE 8

| Structure | Nicotine Receptor IC$_{50}$ (nM) | Tail-Flick Assay ED$_{50}$ (mg/kg) |
|---|---|---|
| CH₃-N-bicyclic-oxadiazole-CH₃ | 100 | 0.230 |
| H-N-bicyclic-isoxazole-CH₃ | 630 | >2,000 |
| CH₃-N-bicyclic-isoxazole-CH₃ | 24 | ~1,000 |
| CH₃-N-bicyclic-quinoline | 77 | — |
| H-N-bicyclic-quinoline | 7 | >2,000 |

EXAMPLE 89

Tail-Flick Assay in Mice and Rats

Female CD-1 mice (20–25 g, Charles River Labs) and male CD rats (300–400 g, Charles River Labs) were housed in groups of two and five, respectively. Animals were given food and water ad libitum. Most studies were performed using groups of 5 animals per treatment unless otherwise noted.

Antinociceptive effects (i.e., analgesia) of test compounds in mice and rats were measured by the tail-flick test using a tail-flick analgesia meter (EMDIE Instrument Co.). A maximum latency of 10 sec was imposed if no response occurred within that time. Antinociceptive activity, measured as % MPE, was calculated as [(test−control)/(10−control)×100)].

Duration of compound and (−)-nicotine-induced antinociception was assessed in mice by measuring antinociception at 2, 5, 10, 20 min after compound (20 µg/kg, s.c.) or nicotine (5 mg/kg, s.c.).

Mice (7/group) or rats were pretreated i.v. (0.9% saline or antagonist, mecamylamine, hexamethonium, atropine, naloxone or yohimbine) 10 minutes before administration of compound or nicotine at different doses. A control response (1.5–4 sec) was determined for each animal before treatment and test latencies were assessed at 5 minutes after compound administration (5 ml/kg, s.c.) or 2 min after nicotine (5 ml/kg, s.c.).

Tables 7, 8 and 9 provide the tail-flick data for selected compounds.

IV. Identification and Use of Nicotinic and Muscarinic Agonists and Antagonists Methods for the determination of the specific cholinergic receptor activity profile for a selected compound is easily determined using known assays. For example, to determine which type or types of acetylcholinergic receptors a compound is interacting with, in vitro competitive binding assays can be performed using specific radioligands. A compound's ability to compete with a specific radioligand for receptor binding indicates an affinity for that receptor type. Radiolabelled nicotine (or cytisine) and quinuclidinyl benzilate are commonly used for nicotine and muscarinic receptor types, respectively. However, whether or not the compound is an agonist or antagonist is typically not determined by these assays.

To differentiate between agonists or antagonists, cell, tissue or animal-based in vitro or in vivo assays are typically employed. For nicotinic receptor ligands, one assay involves treating an animal with compound, then measuring a pharmacological activity associated with nicotinic receptor agonism, such tail-flick analgesia. If compound treatment resulted in analgesic activity, the compound is considered a nocitinic agonist. The compound's agonist activity should also be blocked by known nicotinic receptor antagonists. A similar protocol can be utilized if a cell-based assay, such as release of dopamine from striatal synaptosomes, is used.

If there is no nicotinic agonist activity, e.g. analgesia, in this example, after compound treatment, an effective dose of a known nicotinic agonist (such as nicotine) is subsequently given to the compound-treated animal. If the compound is an antagonist with the ability to block the effects of a known agonist, then the resulting analgesic activity would be less than that expected for the given dose of agonist.

Muscarinic agonists/antagonists can be characterized using appropriate muscarinic receptor-mediated in vitro and in vivo assays. Pharmacologic approaches can include, for example, include receptor-mediated mobilization of $Ca^{+2}$ in cultured cells, depolarization of the rate superior cervical ganglion, or contraction of the longitudinal muscle myenteric-plexus preparation of the guinea pig.

Compounds which act as nicotinic receptor agonists are useful in the treatment of cognitive neurological and mental disorders, including Parkinson's disease, Tourette's Syndrome, Alzheimer's disease, attention deficit disorder, dementia, multi-infart dementia, vascular dementia, cognitive impairment due to organic brain disease including due to alcoholism and brain diseases, general problems with information processing, deficient regional cerebral blood flow and cerebral glucose utilization, psychiatric disorders (e.g., schizophrenia and depression), as well as other conditions such as analgesia, ulcerative colitis, aphthous ulcer, cessation of smoking, body weight loss and treatment of the symptoms of anxiety and frustration associated with withdrawal from other addictive substances, such as, cocaine, diazepam or alcohol. Nicotinic receptor agonists can also be used for veterinary purposes, including as respiratory stimulants, ectoparasiticides, and anthelmitics.

Compounds which act as nicotinic receptor antagonists are useful as ganglion-blocking agents, in the control of blood pressure in hypertension, in autonomic hyperreflexia regulation, in the control of hypotension during surgery and in the reduction of bleeding during operations. These compounds can also be used as stabilizing neuromuscular blocking agents which are extensively used as adjuvants in anesthesia for the relaxation of skeletal muscles, treatment for severe muscle spasms and ventilatory failure from various causes such as obstructive airway disorders. In addition, nicotinic receptor antagonists are useful as depolarizing neuromuscular blocking agents, for example, as skeletal muscle relaxants in endotracheal intubation or psychiatric electroshock therapy to prevent muscle and bone damage. Nicotine antagonists are also useful in blocking both the secretagogue and mitogenic effects of nicotine on cancer cells such as human small cell lung carcinoma. Finally, nicotine antagonists can be used as antidotes for curare/nicotine poisoning.

Muscarinic receptor agonists are widely used for opthalmic purposes, for example, in the treatment of glaucoma to reduce intraocular pressure, applied alone or in combination with β-adrenergic blocking drugs or sympathomimetic agents, or for the treatment of accomodative esotropia. These agonists are also useful for one or more of the following indications: breaking adhesions between the iris and the lens; for the treatment of various disorders involving the depression of smooth muscle activity without obstruction (postoperative atony, congenital megacolon); in stimulating smooth muscle activity in the urinary and gastrointestinal tract; in reflux esophagitis, in the treatment of postoperative atonia of the stomach or bowel; for gastric retention following bilateral vagotomy; for congenital megacolon and combating esophageal reflux; in the treatment of urinary retention and inadequate emptying of the bladder postoperatively or post partum; and in the treatment of memory disorders and cognitive functions of Alzheimer's patients. The efficacy and side-effects of muscarinic receptors may be improved by optimizing their differential activity on various muscarinic receptor subtypes, e.g., M1 vs. M2/M3 receptors, as described by Showell, G. A., et al., *Medicinal Chemical Research,* 1993, 3:171–177.

Muscarinic receptor antagonists (antimuscarinic agents) are widely used in ophthalmology to produce mydriasis and/or cycloplegia. Selective M1 receptor antagonists are effective in treating peptic ulcer disease, and in the inhibition of gastric acid secretion. Antimuscarinic agents are also useful in treating increased tone or motility of the gastrointestinal tract, such as diarrheas, and in combating biliary and renal colics frequently in combination with an analgesic drug. Antimuscarinic agents, including quaternary ammonium compounds, are useful in treating obstructive pulmonary diseases such as chronic bronchitis or bronchial asthma. Cardioselective antimuscarinic agents are useful in treating symptomatic sinus bradycardia, e.g., in acute myocardial infarction, higher degree heart block and certain types of ventricular arrhythimas. Muscarinic receptor antagonists are also used in preoperative medication to counteract the vegal effects, to reduce excessive bronchial secretion, and to produce some sedation and amnesia. Centrally acting antimuscarinic agents are useful in the treatment of Parkinson's disease, by restoring the normal balance of cholinergic and dopaminergic neurotransmission in the basal ganglia, in the prevention of motion sickness, as a sedative, to relieve the symptoms of myasthenia gravis, in the antagonism of skeletal muscle relaxant effects of neuromuscular blocking agents, and in the treatment of poisoning by cholinesterase inhibitors such as those used in insecticides and chemical warfare. Such compounds are also useful to counteract anaesthesia effects, and in mushroom poisoning.

The clinical efficacy and safety of muscarinic receptor antagonists can be optimized by adjusting tissue selectivity, receptor subtype specificity and a balance of antagonism and agonism vs. different receptor subtypes, as well as by selective local (topical, aerosol, eye drop) or systemic administration of the drug.

Modifications and variations of the present invention will be obvious to those skilled in the art from the foregoing detailed description of the invention. Such modifications and variations are intended to come within the scope of the appended claims.

Optical Resolution of (±)-exo-2-(3-methyl-1,2,4-oxadiazol-5-yl)-7-methyl-7-azabicyclo[2.2.1]heptane The title compound (356 mg, 1.85 mmol) was treated with a solution of O,O-dibenzoyl-(L)-tartaric acid (661 mg, 1.85 mmol) in anhydrous ethanol (20 mL). The solution was evaporated, leaving a semi-solid residue. This residue was dissolved in boiling isopropanol (20 mL), diluted with water (5 mL, and allowed to crystallize overnight at −20° C. The crystals were filtered, washed with 4:1 isopropanol-water (5 mL), and dried in vacuo, affording a white solid (456 mg); mp 132–134° C. To this solid was added 2:1 methanol/isopropanol (30 mL), and the resulting slurry concentrated to a volume of approx 10 mL on a hotplate. After cooling for 2 h at −20° C., the crystals were filtered, washed with isopropanol (3 mL), and dried in vacuo, affording the levo salt (374 mg); mp 150° C., [α]D −63.6° (c 0.22, MeOH). This solid was stirred with a mixture of 10% aqueous $Na_2CO_3$ (20 mL), and methylene chloride (20 mL). The organic phase was dried over $Na_2SO_4$, concentrated to a small volume, and filtered through a plug of basic alumina in a pipette to remove suspended solids. Careful evaporation of the solution afforded the dextro free base as a colorless oil (149 mg, 0.77 mmol); [α]D+3.2° (c 7.45, $CH_2Cl_2$).

The mother liquors from the crystallization of the levo salt were evaporated, and the residue partitioned between aqueous $Na_2CO_3$ and $CH_2Cl_2$ as described above, affording a slightly yellow oil (204 mg, 1.06 mmol). This was dissolved in isopropanol (20 mL), and treated with O,O-dibenzoyl-(D)-tartaric acid (379 mg, 1.06 mmol). As the acid dissolved, a precipitate of the salt began to form.[1] The slurry was treated with methanol (10 mL), and boiled for 10 min, then placed in the freezer (−20° C.) overnight. The crystals were filtered, washed with isopropanol (5 mL), and dried in vacuo, affording the dextro salt as a white solid (386 mg); mp 149–150° C.; [α]D+59.1° (c 0.22, MeOH). this solid was converted to the free base as described above, affording the levo base as a colorless oil (146 mg, 0.756 mmol); [α]D−3.4° (c 3.23, $CH_2Cl_2$).

[1] For those trying to reproduce this preparation, I would recommend dissolving the tartaric acid in isopropanol prior to mixing with a solution of the free base. In the above procedure, the tartaric acid goes into solution slowly, but the tartarate salt crystallizes quickly, affording a solid mixture. The digestion with methanol as described above was intended to achieve full mixing of the reactants prior to completion of the crystallization.

The combined yield of both enantiomers was 295 mg (83%).

TABLE 9

| Compound | rat brain, $^3$H-cytisine binding $IC_{50}$ (nM) | tail-flick $ED_{50}$ (mg/kg, s.c.) | | additional visible pharmacol. effects | |
| --- | --- | --- | --- | --- | --- |
| | | rat | mouse | rat | mouse |
| racemic A/B | 100 | 2.2 | 0.2 | nic.* | musc.** |
| A | 1400 | | <0.1 | | musc.** |
| B | 18 | | >1.0 | | musc.** | nic.* nicotinic agonist-like effects including sedation, tremors and cardiovascular effects
musc.** muscarinic agonist-like effects including sedation and salivation

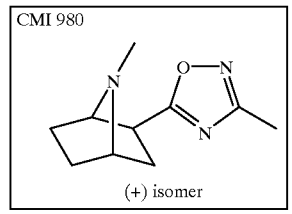

A

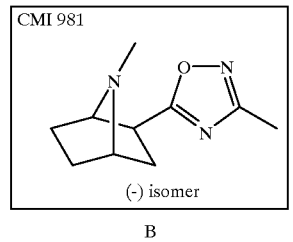

B

We claim:
1. A 7-azabicyclo[2.2.1]heptane compound of the formula:

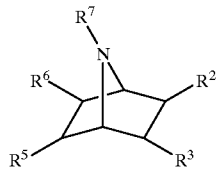

wherein
  $R^3$ and $R^5$ are independently hydrogen; alkyl; hydroxy; hydroxyalkyl; alkyloxyalkyl; alkylthioalkyl; aminoalkyl; alkylaminoalkyl; dialkylaminoalkyl; alkyloxy; alkylthio; halo; haloalkyl; —$NH_2$; alkylamino; dialkylamino; cyclic dialkylamino; amidine, cyclic amidine and their N-alkyl derivatives; —CO$_2$H; —CO$_2$alkyl; —CN; —C(O)NH$_2$; —C(O)CH$_3$; —C(O)NH(alkyl); —C(O)N(alkyl)$_2$; allyl; —SO$_2$(alkyl); —SO$_2$alkyl; —S(O)aryl; or —NHC(O)alkyl;

R$^6$ is hydrogen;

R$^2$ is endo- or exo-

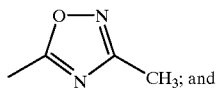

R$^7$ is hydrogen or methyl.

2. The compound according to claim 1, wherein R$^3$, R$^5$, and R$^6$ are hydrogen.

3. The compound according to claim 1 that is at least 95% free of the (+) enantiomer.

4. The compound according to claim 1 that is at least 95% free of the (−) enantiomer.

5. The compound according to claim 2 that is at least 95% free of the (+) enantiomer.

6. The compound according to claim 2 that is at least 95% free of the (−) enantiomer.

7. A method for treating a disorder in a mammal characterized by an increase or decrease in cholinergic function, the method comprising administering an effective amount of the compound of claim 1.

8. A method for treating a disorder in a mammal characterized by an increase or decrease in cholinergic function, the method comprising administering an effective amount of the compound of claim 2.

9. A method for treating a disorder in a mammal characterized by an increase or decrease in cholinergic function, the method comprising administering an effective amount of the compound of claim 3.

10. A method for treating a disorder in a mammal characterized by an increase or decrease in cholinergic function, the method comprising administering an effective amount of the compound of claim 4.

11. A method for treating a disorder in a mammal characterized by an increase or decrease in cholinergic function, the method comprising administering an effective amount of the compound of claim 5.

12. A method for treating a disorder in a mammal characterized by an increase or decrease in cholinergic function, the method comprising administering an effective amount of the compound of claim 6.

13. A pharmaceutical composition comprising a pharmaceutically acceptable carrier or diluent and the compound according to claim 1 or its pharmaceutically acceptable salt, wherein the compound is present in the composition in an amount effective to treat a disease in a mammal characterized by an increase or decrease in cholinergic activity.

14. A pharmaceutical composition comprising a pharmaceutically acceptable carrier or diluent and the compound according to claim 2 or its pharmaceutically acceptable salt, wherein the compound is present in the composition in an amount effective to treat a disease in a mammal characterized by an increase or decrease in cholinergic activity.

15. A pharmaceutical composition comprising a pharmaceutically acceptable carrier or diluent and the compound according to claim 3 or its pharmaceutically acceptable salt, wherein the compound is present in the composition in an amount effective to treat a disease in a mammal characterized by an increase or decrease in cholinergic activity.

16. A pharmaceutical composition comprising a pharmaceutically acceptable carrier or diluent and the compound according to claim 4 or its pharmaceutically acceptable salt, wherein the compound is present in the composition in an amount effective to treat a disease in a mammal characterized by an increase or decrease in cholinergic activity.

17. A pharmaceutical composition comprising a pharmaceutically acceptable carrier or diluent and the compound according to claim 5 or its pharmaceutically acceptable salt, wherein the compound is present in the composition in an amount effective to treat a disease in a mammal characterized by an increase or decrease in cholinergic activity.

18. A pharmaceutical composition comprising a pharmaceutically acceptable carrier or diluent and the compound of claim 6 or its pharmaceutically acceptable salt, wherein the compound is present in the composition in an amount effective to treat a disease in a mammal characterized by an increase or decrease in cholinergic activity.

19. The method of claim 7, wherein said disorder involves inhibition or stimulation of the muscarinic cholinergic receptor.

20. The method of claim 8, wherein said disorder involves inhibition or stimulation of the muscarinic cholinergic receptor.

21. The method of claim 9, wherein said disorder involves inhibition or stimulation of the muscarinic cholinergic receptor.

22. The method of claim 10, wherein said disorder involves inhibition or stimulation of the muscarinic cholinergic receptor.

23. The method of claim 11, wherein said disorder involves inhibition or stimulation of the muscarinic cholinergic receptor.

24. The method of claim 15, wherein said disorder involves inhibition or stimulation of the muscarinic cholinergic receptor.

25. The method of claim 7, wherein said disorder involves inhibition or stimulation of the nicotinic cholinergic receptor.

26. The method of claim 8, wherein said disorder involves inhibition or stimulation of the nicotinic cholinergic receptor.

27. The method of claim 9, wherein said disorder involves inhibition or stimulation of the nicotinic cholinergic receptor.

28. The method of claim 10, wherein said disorder involves inhibition or stimulation of the nicotinic cholinergic receptor.

29. The method of claim 11, wherein said disorder involves inhibition or stimulation of the nicotinic cholinergic receptor.

30. The method of claim 12, wherein said disorder involves inhibition or stimulation of the nicotinic cholinergic receptor.

31. The method of claim 7, wherein the compound is administered to a human in an amount ranging between 0.002 and 10 mg/kg per day.

32. The method of claim 8, wherein the compound is administered to a human in an amount ranging between 0.002 and 10 mg/kg per day.

33. The method of claim 9, wherein the compound is administered to a human in an amount ranging between 0.002 and 10 mg/kg per day.

34. The method of claim 10, wherein the compound is administered to a human in an amount ranging between 0.002 and 10 mg/kg per day.

35. The method of claim 11, wherein the compound is administered to a human in an amount ranging between 0.002 and 10 mg/kg per day.

36. The method of claim 12, wherein the compound is administered to a human in an amount ranging between 0.002 and 10 mg/kg per day.

37. A method for imparting analgesia in a mammal, comprising administering to a mammal an effective amount of the compound of claim 1.

38. A method for imparting analgesia in a mammal, comprising administering to a mammal an effective amount of the compound of claim 2.

39. A method for imparting analgesia in a mammal, comprising administering to a mammal an effective amount of the compound of claim 3.

40. A method for imparting analgesia in a mammal, comprising administering to a mammal an effective amount of the compound of claim 4.

41. A method for imparting analgesia in a mammal, comprising administering to a mammal an effective amount of the compound of claim 5.

42. A method for imparting analgesia in a mammal, comprising administering to a mammal an effective amount of the compound of claim 6.

* * * * *